United States Patent [19]
Jacobs et al.

[11] Patent Number: 5,994,137
[45] Date of Patent: Nov. 30, 1999

[54] L5 SHUTTLE PHASMIDS

[75] Inventors: William R. Jacobs, City Island, N.Y.;
Graham F. Hatfull, Pittsburgh, Pa.;
Stoyan Bardarov, Bronx, N.Y.; Ruth McAdam, Essendon, United Kingdom

[73] Assignees: Albert Einstein College of Medicine of Yeshiva University, Bronx, N.Y.; University of Pittsburgh, Pittsburgh, Pa.

[21] Appl. No.: 09/075,904

[22] Filed: May 11, 1998

Related U.S. Application Data

[63] Continuation of application No. 08/247,901, May 23, 1994, Pat. No. 5,750,384, which is a continuation-in-part of application No. 08/057,531, Apr. 29, 1993, abandoned, which is a continuation-in-part of application No. 07/833,431, Feb. 7, 1992, abandoned.

[51] Int. Cl.$^6$ .............................. C12N 15/63; C12N 15/74
[52] U.S. Cl. ........................... 435/473; 435/474; 435/476
[58] Field of Search .................................. 424/93.2, 93.4, 424/200.1, 248.1; 435/172.1, 172.3, 252.3, 253.1, 473, 474, 476

[56] References Cited

U.S. PATENT DOCUMENTS 5,504,005  4/1996  Bloom et al. ......................... 435/253.1

OTHER PUBLICATIONS

Kalpana et al. (1991) Insertional mutagenesis and illegitimate recombination in mycobacteria. Proc. Natl. Acad. Sci USA 8:5433–5437, Jun., 1991.

*Primary Examiner*—Nancy Degen
*Assistant Examiner*—Robert Schwartzman
*Attorney, Agent, or Firm*—Amster, Rothstein & Ebenstein

[57] ABSTRACT

This invention is directed to L5 shuttle phasmids capable of delivering foreign DNA into mycobacteria and to methods of producing L5 shuttle phasmids. In addition, this invention is directed to a method of generating mycobacterial mutations and to a method of producing mycobacterial vaccines.

9 Claims, 18 Drawing Sheets

L5 SHUTTLE PHASMIDS

CROSS REFERENCE TO RELATED APPLICATIONS

This application is a continuation of U.S. patent application Ser. No. 08/247,901 filed May 23, 1994, now U.S. Pat. No. 5,750,384, issued May 12, 1998; which is a continuation-in-part of U.S. patent application Ser. No. 08/057,531, filed Apr. 29, 1993, now abandoned; which is a continuation-in-part of U.S. patent application Ser. No. 07/833,431, filed Feb. 7, 1992, now abandoned, the contents of each of which are hereby incorporated by reference in their entirety.

STATEMENT OF GOVERNMENT INTEREST

This invention was made with government support under Grant Numbers A127235, A126170, A128927 and A123545. As such, the government has certain rights in the invention.

FIELD OF THE INVENTION

This invention relates to L5 shuttle phasmids which are capable of delivering foreign DNA into mycobacteria. The L5 shuttle phasmids of the invention are used to generate mycobacterial mutations, which can be used to produce mycobacterial vaccines.

BACKGROUND OF THE INVENTION

Tuberculosis (which includes infection caused by M. tuberculosis, M. bovis, BCG and M. africanum) remains the largest cause of human death in the world from a single infectious disease, and is responsible for one in four voidable adult deaths in developing countries. In addition, in 1990, there was a 10% increase in the incidence of tuberculosis in the United States.

In the past, infection with drug-sensitive strains of the M. tuberculosis complex had been cured with certain antibiotics, including isoniazid, rifampicin, ethionamide and pyrazinamide. However, resistance to isoniazid and other antibiotic drugs has developed in many strains of M. tuberculosis. This has resulted in the search for an effective vaccine against M. tuberculosis. Further, this has enhanced the need to develop new drugs which are effective against drug-resistant strains of M. tuberculosis. It is therefore desirable to develop molecular and genetic tools which can be utilized to understand the pathways involved in invasion, survival and persistance of M. tuberculosis and in the development of vaccines and new drugs.

The creation of mutants in M. tuberculosis and BCG is of essential importance in the analysis of M. tuberculosis and BCG gene function. Auxotrophic mutants have been isolated in M. smegmatis by both shuttle mutagenesis and N-methylN'-nitroso-N-nitrosoguanidine treatment followed by isoniazid enrichment. These methods, however, are less effective in the M. tuberculosis complex (M. tuberculosis, M. bovis, M. miroti and M. africanum) due to current difficulties in performing homologous recombination, which is required by the shuttle mutagenesis procedure. Also, the tendency of mycobacteria to clump limits the use of traditional mutagens and makes positive selection advantageous.

Because the creation of mutants in M. tuberculosis and BCG is of essential importance in the analysis of gene function, it is desirable to develop effective means and methods for delivering foreign DNA into M. tuberculosis and BCG. The insertion of foreign DNA into M. tuberculosis and BCG mycobacteria would provide the necessary tools for understanding the mechanisms by which these mycobacteria survive and replicate. In addition, it would provide valuable tools for the development of vaccines and new drugs effective in the treatment of infection caused by M. tuberculosis and BCG.

It is therefore and object of this invention to provide shuttle phasmids capable of delivering foreign DNA into mycobacteria.

It is another object of this invention to provide a method of producing shuttle phasmids capable of delivering foreign DNA into mycobacteria.

It is a further object of this invention to provide a method of generating mycobacterial mutations.

It is another object of this invention to provide mycobacterial mutants.

It is a still further object of this invention to provide a method of producing a mycobacterial vaccine.

SUMMARY OF THE INVENTION

This invention is directed to L5 shuttle phasmids capable of delivering foreign DNA into mycobacteria, which shuttle phasmids comprise an L5 mycobacteriophage containing an E. coli bacteriophage lambda cosmid inserted into a non-essential region of the L5 mycobacteriophage genome.

This invention is further directed to a method of generating mycobacterial mutations comprising producing a mycobacteriophage L5 shuttle phasmid containing a cosmid and a transposon therein, propagating the L5 shuttle phasmid, and infecting mycobacteria with the propagated L5 shuttle phasmids so as to cause delivery of the transposons from the L5 shuttle phasmids to the chromosomes of the mycobacteria, thereby causing mutations in the genes of the mycobacteria to occur. Once mycobacterial mutations have occurred, a marker gene present in the transposons is selected for in order to identify mycobacterial mutants in which the transposons have been delivered, and the mutants can be screened to identify a mutant of interest, such as an avirulent mutant. Certain mutants, including avirulent mutants can be used as mycobacterial vaccines.

In addition, this invention is directed to a method of determining whether an L5 gene is essential for L5 propagation. In order to perform this, a mutation of an L5 gene is generated utilizing a cosmid form of an L5 shuttle phasmid and recombinant DNA methodology so as to obtain an L5 shuttle phasmid mutant. The L5 shuttle phasmid mutant is propagated and then transfected in M. smegmatis in order to determine whether plaques have formed, the presence of plaques indicating that the L5 gene is not essential for L5 propagation.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 11A depicts the restriction fragments of those clones transformed with Tn5367-containing plasmid pYUB285. FIG. 11B depicts the restriction fragments of those clones transformed with Tn5368-containing plasmid pYUB297. The clones were digested with KpnI (black bars) or BamHI (hatched bars) and hybridized with pYUB285. They have been arranged in descending order according to the KpnI fragment size to show the randomness of transposition and allow comparison of clones having similar KpnI fragments but different restriction patterns with BamHI;

DETAILED DESCRIPTION OF THE INVENTION

Figure 1:
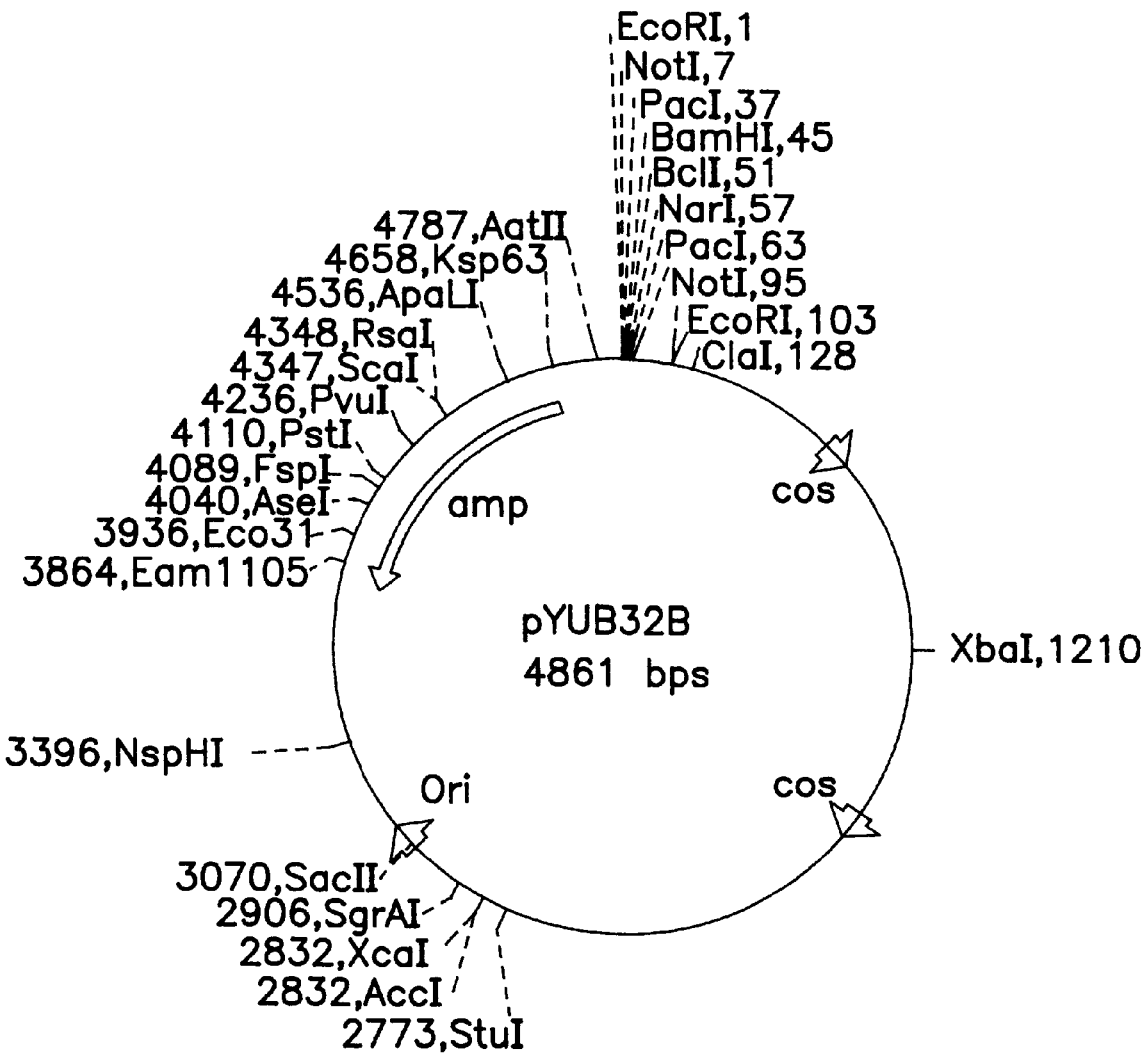
FIG. 1 represents the double-cos vector pYUB328 derived from super cos vector. pYUB328 incorporates pak I sites blanking the BAMHI and NorI sites into which random fragments can be cloned. Since mycobacterial genomes do not have pacI sites in their chromosomes, the pYUB328 vector allows for the release of the cloned fragment. pYUB328 contains an E. coli origin in an ampicillin-resistant gene and bacteriophage lambda cos sequences.

This invention is directed to L5 shuttle phasmids capable of delivering foreign DNA into mycobacteria. The L5 shuttle phasmids are produced by inserting a cosmid into a non-essential region of an L5 mycobacteriophage genome. In addition, other foreign DNA can be inserted into the L5 shuttle phasmid, including reporter genes (such as a luciferase gene), a transposon (such as IS1096), and a gene which encodes a mycobacterial inhibitor (such as anti-sense RNA which has a target of a mycobacterial gene necessary for mycobacterial survival). Further, a DNA-modifying enzyme, and RNA-modifying enzyme or a protein-modifying enzyme can be inserted into the L5 shuttle phasmids of the invention for subsequent insertion into mycobacteria, including $M.$ $tuberculosis,$ $M.$ $smeqmatis,$ BCG and $M.$ $bovis.$ Once L5 shuttle phasmids are obtained, they can be utilized to generate mycobacterial mutations. These mutations can be used to study the mechanisms of mycobacteria as well as to develop vaccines and drugs effective in the treatment of mycobacteria.

In order to generate mycobacterial mutations, L5 shuttle phasmids are produced by inserting a cosmid, such as an $E.$ $coli$ bacteriophage lambda cosmid, and a transposon, such as IS1096, into the genome of an L5 mycobacteriophage. Once the cosmid and transposon are inserted into the L5 mycobacteriophage, an L5 shuttle phasmid is created and is then propagated in a conditional host. The propagated L5 shuttle phasmids are infected into mycobacteria so as to cause delivery of the transposons from the L5 shuttle phasmids to the chromosomes of the mycobacteria, thereby causing mutations in the genes of the mycobacteria to occur. A mycobacterial mutation library is thereby obtained.

In order to produce mycobacterial vaccines, the mycobacterial mutation library is utilized. The presence of a marker gene in the transposons is selected for. This identifies mycobacterial mutants in which the transposons have been delivered into the mycobacteria. Screening is then performed in order to identify a mutation of interest. For example, screening can be performed for an avirulent mutant. Avirulent mutants and other mutants can then be used as mycobacteiral vaccines. Examples of marker genes which can be selected for are kanamycin resistance genes, hydromycin resistance genes and L5 immunity genes. An example of an avirulent mutant which can be screened for is a leucine auxotroph.

Further, this invention is directed to a method of determining whether an L5 mycobacteriophage gene is essential for L5 propagation. In order to perform this, a mutation of an L5 gene is generated utilizing a cosmid form of an L5 shuttle phasmid and recombinant DNA technology so as to obtain an L5 shuttle phasmid mutant. The mutant is then propagated and transfected into $M.$ $smegmatis$ in order to determine whether plaques have formed. If plaques have formed, this indicates that the L5 gene is not essential for L5 propagation. If no plaques have formed, this indicates that the L5 gene is essential for L5 propagation. The construction of several L5 shuttle phasmids of the invention is described below.

EXAMPLE 1

Construction of L5 Shuttle Phasmids

Figure 2:
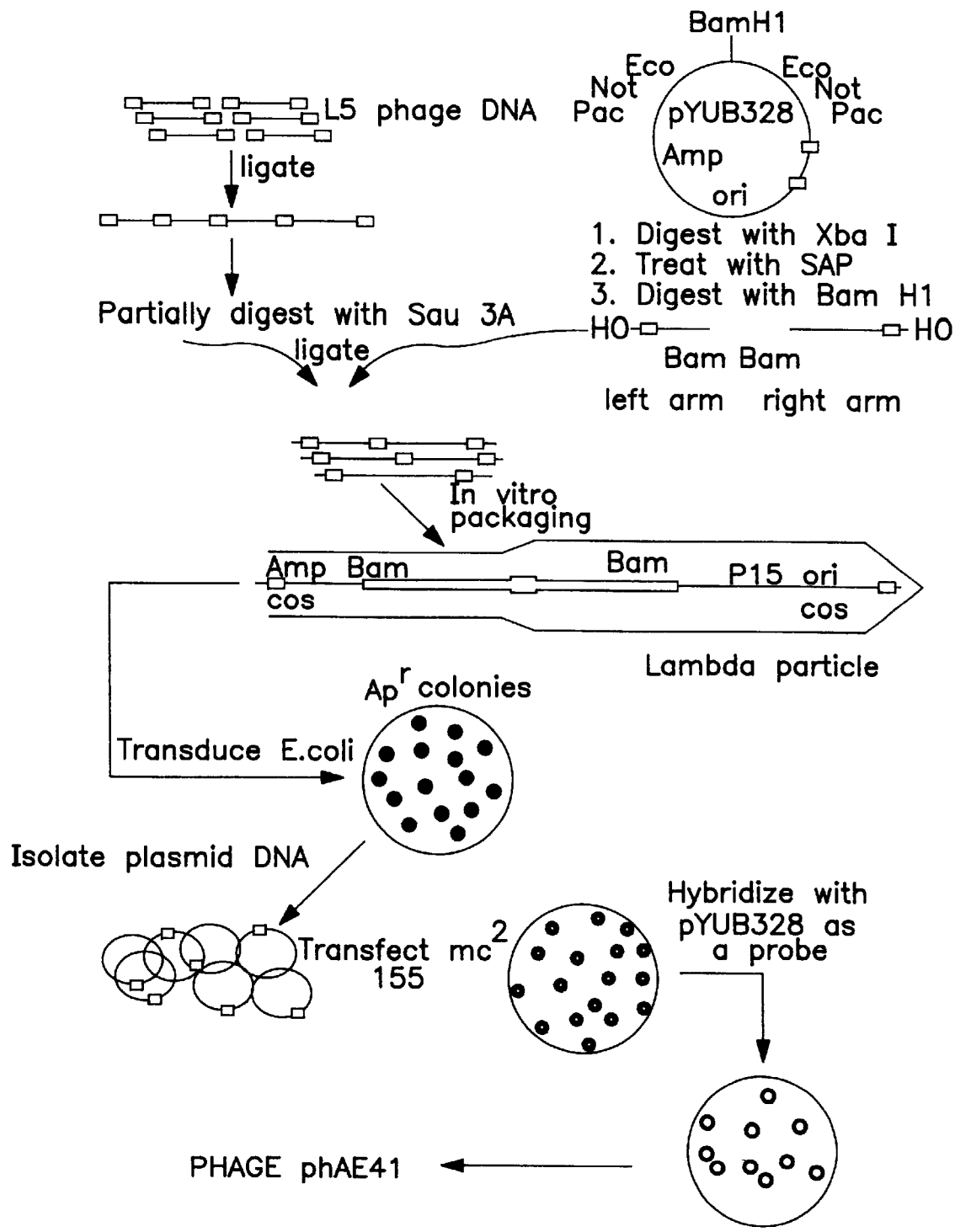
FIG. 2 represents a schematic diagram of L5 shuttle phasmid construction.

In order to construct an L5 shuttle phasmid, an *E. coli* cosmid pYUB328 (see FIG. 1) was inserted into a non-essential region of the L5 mycobacteriophage genome (see FIG. 3) by the method described by. Jacobs, et al., *Nature*, Vol. 327, pp.532–536 (1987). Cosmid pYUB328 was deposited with the American Type Culture Collection, Rockville, Md., on May 20, 1994 and catalogued as ATCC No. 69631. FIG. 2 represents a schematic diagram of L5 shuttle phasmid construction in accordance with the present invention. This generated a cosmid library of partially-digested mycobacteriophage genomes which replicated in *E. coli* as recombinant plasmids. Individual mycobacteriophage-cosmid clones were analyzed and it was determined that construction of the library had generated a set of cosmid-insertions at random sites around the L5 mycobacteriophage genome, which is typically accompanied by the generation of a small deletion of the mycobacteriophage genome at the site of insertion. This library was transfected into *M. smegmatis* cells and resulted in the identification of recombinant mycobacteriophages which have the *E. coli* cosmid inserted at non-essential regions of the L5 mycobacteriophage.

Previously constructed shuttle phasmids, for example the L1 shuttle phasmid constructed by Snapper et al., *Proc. Natl. Acad. Sci. USA*, Vol. 85, pp. 6987–6991 (1988), have not been as useful for insertion of foreign DNA into mycobacteria as they have contained deletions of the cosmid. The inventors concluded that these deletions likely indicate that mycobacteriophage L5 has rigorous packaging constraints, and therefore used a smaller, double-cos, cosmid, pYUB328, which as constructed by Balasubramanian, et al., (1994). This yielded a 3.8 kb cosmid following in vitro packaging into lambda heads.

A library of over 5000 Ap$^r$ (ampicillin-resistant) pYUB328::L5 recombinant clones was generated. Cosmid DNA isolated from *E. coli* was transfected into *M. smegmatis* in order to propagate it. Transfection of plasmid DNA of the library isolated from *E. coli* into *M. smegmatis* cells yielded 34 plaques. Eleven of these plagues were found to hybridize to pYUB328. DNA was prepared from mycobacteriophage particles and analyzed by restriction analysis. Five different classes of pYUB328 insertions into L5 were generated, which represented different size deletions of the genome. All of the L5 shuttle phasmids contained pYUB328 inserted near the immunity gene of mycobacteriophage L5. One of the shuttle phasmids was designated phAE41 by the inventors (see FIG. 4). L5 shuttle phasmid phAE41 was deposited with the American Type Culture Collection, Rockville, Md. on May 20, 1994, and catalogued as ATCC No. 69624.

EXAMPLE 2

Molecular Characterization of L5 Shuttle Phasmid phAE41

Figure 4:
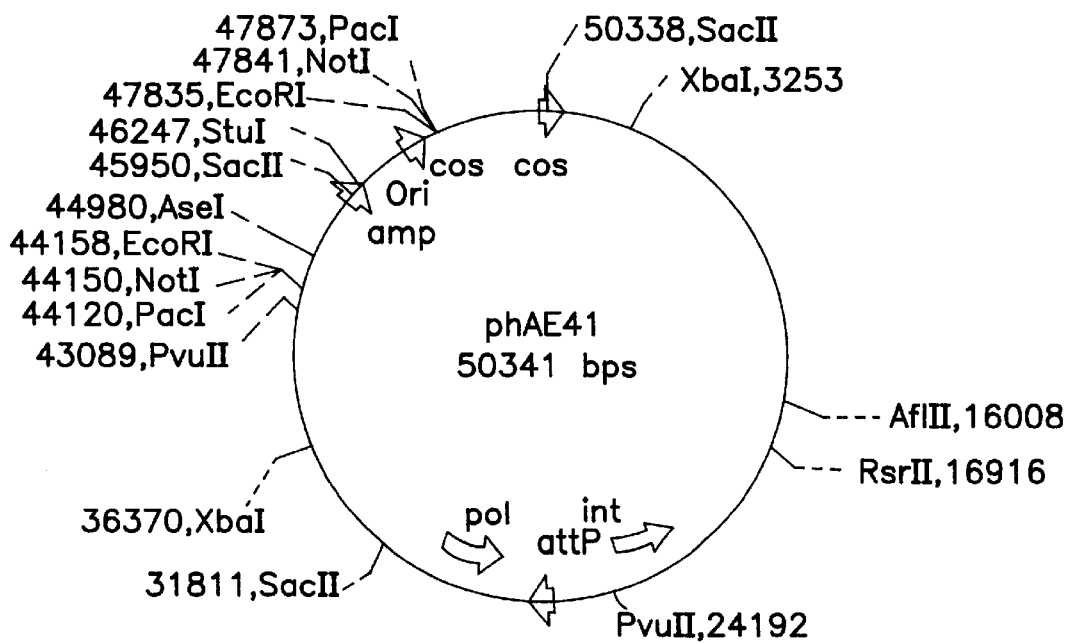
FIG. 4 represents a schematic diagram of the L5 shuttle phasmid phAE41 in which the cosmid pYUB328 was inserted into the immunity region of mycobacteriophage L5.

Experiments were performed to confirm that phAE41 was a shuttle phasmid constructed from mycobacteriophage L5. DNA isolated from mycobacteriophage particles of phAE41 was ligated together to yield long concatamers and then packaged in vitro into bacteriophage lambda heads. The resulting bacteriophage-packaged particles were capable of transducing ampicillin-resistance at high frequencies. This was determined by mixing the in vitro packaged lysate with a-sensitive *E. coli* cells and then plating on agar containing 5 µg/ml ampicillin. The phAE41 yielded $10^4$ ampicillin-resistant colonies. Comparisons of restriction analyses of plasmids isolated from *E. coli* and phage-digested molecules demonstrated identical patterns except for the unligated cohesive ends of the linear phage molecules. These results demonstrated that the phAE41 molecules were stable in both mycobacteria and *E. coli*. However, unlike the phAE15 shuttle phasmid derived from L1 (Snapper, et al., 1987), the entire cosmid in the L5 shuttle phasmid was stably maintained in shuttle phasmid phAE41. In addition, the *E. coli* cosmid portion of the shuttle phasmid could be completely removed from the phAE41 with any of three enzymes, PacI, NotI or EcoR1. Restriction analyses was used to determine the site of insertion of the pYUB328 cosmid, and thus the complete sequence of the phAE41 was deduced. The map of phAE41 is shown in FIG. 4. The sequence for phAE41 is shown below:

```
                                  SEQ ID NO: 1

1 GGCGCTCTCG CATCGCATCG AGTGTTTGCT GTGTCTCTCA TCGTCGCAGG TCAGAAGGGG

61 TAGGGGGGTT CCCCCTAGGG GTCGGTCCTT GACCGGTCGG TTAGGTCGGT TATGCGGCCG

121 AGCCATCCTG TACGGGTTTC CAAGTCGATC AGAGGTAGGG GCCGGCACAG AAACCACTCA

181 CATCAGGGCT GTGCGCCTCC AGGGCGCGTG AACTCCCACA CCCCGGTGTA GTTACATCCC

241 GGAATTGTCT CAGCGCCTCT CAGGGCGCTT CTCATAAACA GTGATCTACG CCACTCCTGA

301 CGGGTGGCTG TCAAGGATAC TCACCTTCCC TACTAATGAG GGGCTAAGAG CCCCTCTCTA

361 TAGAGCGCCG CACAGGCGGC GCGATAAGAG CGCCACCAGG CGCTCATCTA AAGACCGGCC

421 TTGAAGGGCC GGTCATAGAG ATCTATTCGA TCCGGCAACC GCCGGATCTC AAGGCCGCGC

481 CAGTGCGCGG CCCTATAGAG GGGTGACTCA ACTGTGCATG GCACTCGCTC GAGTGCCCAC

541 TGGAGCACTC AACCGGGGAA GTTCGACGTT CTCAACCTGC GAATGACGTT TGAATCGTCA

601 TCCGCGTACG AAATCCCCGA TCTGCGGCCG ACCGACTTCG TGCCGGCCTA TCTCGCGGCC

661 TGGAATATGC CGCGTCACCG CGATTACGCC GCCAAGAACG GCGGCGCGCT GCACTTCTTC

721 CTTGACGATT ACCGGTTTGA GACCGCGTGG TCGTCCCCCG AGCGCCTTCT CGACCGCGTA
```

SEQ ID NO: 1-continued

```
 781 AAGCAGGTCG GCGCTGCACT CACGCCGGAT TTCAGCCTCT GGACGAACAT GCCGAAGGCG
 841 GCGCAGCTAT GGAACGTCTA CCGCTCCCGC TGGTGTGGCG CGTATTGGCA GTCGGAAGGA
 901 ATCGAGGTGA TTCCGACGGC GTGTTGGGCG ACTCCCGACA CGTTCGATTT CTGTTTCGAC
 961 GGGATCCCGA TGGGATCGAC CGTCGCAATT TCTTCGATGG GCATTCGCTC TTCAAAAGTC
1021 GACCAGGAGC TTTTCCGGTA CGGACTACGC GAACTCATCG ATCGCACTCA ACCGCAACTG
1081 CTTTTGGCAT ATGGCCAGCT TCGGCATTGC GACGACATGG ATTTACCAGA GGTCCGCGAA
1141 TACCCGACCT ACTGGGACAG ACGACGAAAG TGGGTAACTG CCGATGGGAG GCCGGGGAAG
1201 TAAAGGCGGC CCCGGTCCCG GAACCGGAGC ACGCAACCGC AGAGGCGCTG GAGCCCCCGG
1261 ATCGGGCGGC GTAGGCGGCG TCGGAGGCGG GGGTGGAGCT GCAGGGAGCA GCGGAGGCGG
1321 CAAGGGAACG GCAGCGCCGG TACCGGAGGC GTCACCGGTG GCGGCGGAAG TGGAGCCGGC
1381 GGCGGTGGCA GCAGCCCCAA CACCCCGGTG CCCCCCACCG AGCTGGAGAA GAAGCGCGGC
1441 GAATACAACC AGATCGCCAT CGACGCCCAG AAACAGCACG CGCCCACCGA TGAGAAGCGC
1501 GAGGCCAAGC GCAAGCAACT GATGGATCGA GTCGGAGGAG ACTGGCAGGC TTTTGGACCCG
1561 GATCACCACG ACGCCATCAA GGTGGCGATG GATGACGCCA TGCGGAAGAT CCTCTCCGAG
1621 GAGGAGATCG TCCACCGCAC CAAGCACTTC GGCGACCTAC TCGACCATAC TCGACTCAAG
1681 TCGCTGTTCG AGGTCGGCTT CTCAGCCGGT GGCGACACCC CGACCGAACG CGCCCTCCTC
1741 GAGGACGCCT GGTTCGGCGC AGGCAAGGTT CCCCCGATCT ACTCGGCAAT CGAGTTCAAC
1801 GGCGCTCCGA CAGCCGGCCT CGGCATGTAC GGCGGCACCA AGCTCTACAT GAAGGACTCG
1861 GTCAAGGACC GCGTCACCGT GACCATCGGC GACTCGCTGA TGTCGAGCTG GGACGTATTC
1921 CCCGGCCGTC CTGGCGACGG CGTGGGGCTG TGGGCCAGCC TGTCGAAGAT CGAGGGGCTG
1981 GTCGATCCGA GCAAGACCCG CGAAGAGAAC ATGCAGGCGG TGTACGACTC GTTCAAGAAG
2041 TACGGCACCC TGGACGGCTT CATCGAGGCG CAGATCCACG GCGGCGTCCT GGTCGAGGAC
2101 ATCAAGAAGG TCGTGTTCAC GCAGCCGCCG AGCCCGATCT TCACCGATAA ACTGGACGAA
2161 CTTGGAATCC CGTGGGAGGT GCAGTAATGG CGCAGATGCA GGCGACACAC ACAATCGAGG
2221 GGTTCCTGGC TGTCGAGGTG GCCCCTCGGG CGTTCGTCGC AGAGAACGGC CACGTACTGA
2281 CCCGGCTGTC GGCCACGAAG TGGGGCGGTG GCGAGGGTCT CGAGATCCTC AACTACGAGG
2341 GTCCAGGGAC CGTCGAGGTC TCCGACGAGA AGCTCGCCGA AGCCCAGCGG GCCAGCGAGG
2401 TCGAGGCTGA ACTTCGCCGC GAGGTCGGCA AGGAGTGAGC TGGGCCGGCT CAGGCCGGCG
2461 ACAGGAACTA CCAGAGGACT GGGAGCTGAA TTACCGGCTC CCGGTCCTTT CTGCTGCCAA
2521 CTGGCTTTGC CAGATCAACG GTCCCGGATG CGTAAGGGCC GCAACCGATG TCGACCACAT
2581 CAAGCGCGGG AACGACCACA GCCGGTCCAA TCTGCAGGCA GCCTGCCATG TCTGTCACGG
2641 CAAGAAATCA GCCGCCGAGG GCGTAGCCCG ACGGCGGGAA CTTAGAGCCC GGAGGAAGCG
2701 ACCACCCGAA CGCCATCCTG GGCGTCGATA AGCGGGCCAG GTGCCCGCTC ACCCAGGAG
2761 GTGAACAGTG GCACGCGAG GCCCAATCGG AAAACGAGAT GAAGAGCGGG TTCGTCGGAA
2821 CACCCCGGAC AGTCCAACCG ACACGATCCA GATGCCCGGT CTGGTGACGA TCCCCGAGAT
2881 GGGCGATCTA AGCCACGACG GCCGCACGCA CCAGCTCGTC AAGGACATGT ACGAGTCGAT
2941 CAAGCAGTCG GCAGCCGTGA AGTACTACGA GCCGACCGAC TGGCAGATGG CCCGACTCGC
3001 CCTCTACACA CTTAACCAGG AACTCATCGC AGCCGAGAAC AACGGCAAGC CCGTGGGCGC
3061 GATGAAGCTC ACTGCCATCA ACCAGATGCT CTCCGCGCTG CTGCTGACCG AAGGTGACCG
3121 ACGCCGCGTC CGACTCGAAG TCGAACGAGC ACCCGCTGAC CCGACAGGCG GGAAGGTCGT
```

SEQ ID NO: 1-continued

```
3181 TGACGTGACC GACGTGCTCA AGCAGCGCCT CGCCAAGGCG AGCGGCGGGA GCTGATGGTC
3241 CCCCGAGGGG TTTCTAGAGC CGCTGCCGCT ACCAGCCGCT CCCCCTCGGG GTAGACATCG
3301 AAAGGAACCA CATGGCCGAC CTCGGCAACC CACTCGACCT CGAGATGCTC TGCCTGGTCA
3361 CAGGCCGGGA CTTCCGCTGG ACCATCGATT ACCCGTGGGG TCCGGGAGAG CTGTTCCTCG
3421 AACTCGAGAC CGGCGGCGAA CACAACGCGC TGCATCAGGT CTATGTCACC GGGGCGACCG
3461 GAGGCACGTA CACGCTGAAC GTCAACGGCA CCAACACCCC GGCCATCGAC TACAACGACG
3541 TGTCGGAGAA TCCGCAGGGG CTGGCAGGCG ACATCCAAGA CGCTCTGGAC GCAGCCGTCG
3601 GAGCCGGAAA CGCTGTCGTG CATCCGGTCT CGCTGTTCCC TGCGTGGACA CTGAACTTCA
3661 ACCTCAACGC CAGCAAGCCG CTCACCGAGC AGTTGGTCAA CACGATCAAC AAGGCCGCGA
3721 ACGACTTCTT CGACACGTTC GACCAACTAC TTGGGGTCGA CGTGGAGATG ACGGTCACCG
3781 ACACCCTGAA CTTCAAGCTC AAGGTGACCT CGCGGCGCTC GTTCGATGAG GTCGGTGTCG
3841 TCACGTTCGC GGTCGACGTG ACCAGCCAGG CAGTCATCAA CTTCTTCAAC TCCGTCGCCG
3901 AACTCACCGG AGCGGTGAAC ACCGTCAACG TCGACTTCTA CTGGAACCGG ACGTATGACA
3961 TCGAGTTCAC CGGATCCCTT GGGCTGCAGC CGATTCCGGC TACTACAGCC GACATCACCA
4021 ACCTGGCGGG TACCAGCAAG GCCGTCTCAG TCACGGTGGT CGAGCCAGGA AGAAGAGGC
4081 TGACCATCTG GCCGTTCACG GTCAACGGTG AAACCGCAAC CATCAAGGTC GAGTCCGAAG
4141 AGGCCGACAA GATCCCCAAC CGCTGCCGCT GGCAGTTGGT TCACATGCCG ACCGGCGAGG
4201 CAGCCGGCGG CGATGCAAAG CAGCTCGGCC GCGTTTACCG ACAGCCGAGG TAACACCGCA
4261 CCCATCAGAG ATGGTGGGCC AGACGGCCTT CGGGCCGTCC CCTGACGTGT AGCTCAATGG
4321 CAGAGCGCCC GACTGTTAAT CGGGTGGTTG AAGGTTCGAG TCCTTCCATG TCAGCGAGGG
4381 CTGAACCGGA CCCGTGTCCG GTGTAGGCAC TTTCCGCAGG CGGTTCCCCA GAGCGTGGGG
4441 AGCCCCTGCC CTGTACACGT AGCTCAATTG GTAGAGCAGC GGTCTCCAAA GCCGCCGGTT
4501 CCAGGTTCGA CTCCTGGCGT GTATGCACAC ACCCCTGACT CCTGCTAGCG GAGTGTTCGC
4561 CTTTCGGGCC TGGGGTCTTT TTCCCCGTTC GTCTAATCGG TAAGACACCC GGCTCTGGAC
4621 CGGGCAATTG AGGTTCGAGT CCTTGGCGGG GAGCCAACTT GACATCCACC CGAAAGGAAC
4681 AACATGACCT TCACAGTCAC CCGCGAGAGA GCGCAGTGGG TCCACGACAT GGCCCGCGCT
4741 CGCGACGGTC TCCCCTACGC GTACGGCGGG GCGTTCACCA ACAACCCGAG GGTGTCGACT
4801 GACTGCTCTG GCCTGGTGCT GCAGACCGGG GCTTGGTATG GAGGTCGCAC CGACTGGGTC
4861 GGAAACCGTT ACGGCTCAAC CGAATCGTTC CGGCTCGACC ACAAGATCGT CTACGACCTA
4921 GGGTTCAAGC GGATGCCCCG AGGCGGGCCA GCGGCCTTGC CGATCAAGCC GGTGATGCTC
4981 GTCGGGCTCC AGCACGGAGG CGGCGGGGTC TACTCGCACA CCGCTTGCAC GTTGATGACG
5041 ATGGACCACC CCGGTGGCCC GGTCAAGATG TCCGACCGAG GCGTCGACTG GGAGTCCCAC
5101 GGCAACCGCA ACGGCGTAGG CGTCGAACTT TACGAGGGCG CACGGGCATG GAACGACCCT
5161 CTGTTCCATG ACTTTTGGTA CCTGGACGCA GTCCTCGAAG ACGAAGGAGA CGATGACGAA
5221 TTGGCTGACC CAGTTCTAGG GAAGATGATC CGCGAGATCC ACGCGTGCCT GTTCAATCAG
5281 ACCGCGTCGA CCAGCGATCT GGCGACCCCT GGTGAAGGCG CTATCTGGCA GCTACACCAG
5341 AAGATCCACT CGATTGACGG CATGCTCCAC CCGATCCACG CTGAGCGGCG CGCTCGCGCA
5401 GGCGATCTCG GTGAGCTGCA CCGAATCGTG TTGGCCGCGA AGGGCTTGGG CGTGAAGCGC
5461 GACGAGGTGA CCAAGCGGGT CTACCAGAGC ATCCTCGCCG ACATCGAGCG GGACAACCCC
```

SEQ ID NO: 1-continued

```
5521 GAAGTACTTC AGCGATACAT CGCAGAAAGA GGTGGCCTAT GAGCCCCAAG ATCCGACAGA
5581 CCATCTACCT GCTCGGCACC GCCGCCCCGG CACTGCTGGG CATCGTCCTG ATCTGGGGCG
5641 GGCTCGACGC TGAGTCGGCG GCTGACCTCG GTGACATCAT TGCGGGCGTC GTGTCGATAC
5701 TAGTCTCCGG TGCGCCGGCC GTAGCGGCAG GCACCGTACG CAGCCAGCGC AAGGACGGCA
5761 CGTTGTCCAC CAGCCCGGTG GATCAGGTCA CCAAGGGCGT CGAGCAGGTG CTCGCGGCCA
5821 GGCAGAGTGC CGAGGCTGAA GTCGCGAAGG TCAAGCAGGC GCTGGAGACC GCCGTCAGCG
5881 GTTCTCTCCC CCAGCTCGGC CCGCTGGCCA CGCAGATCCT CAACGTGGCT GACGACACCG
5941 TCTGGCGTCC ATGAGCAAGC CCTGGCTGTT CACCGTCCAC GGCACAGGCC AGCCCGACCC
6001 GCTCGGGCCT GGTCTGCCTG CCGATACCGC ACGGGACGTA CTTGACATCT ACCGGTGGCA
6061 GCCCATCGGC AACTACCCGG CAGCGGCGTT CCCGATGTGG CCGTCGGTCG AAAAGGGTGT
6121 CGCTGAGCTG ATCCTGCAGA TCGAGCTGAA GCTGGACGCA GATCCGTACG CGGACTTCGC
6181 GCTGGCCGGC TACTCGCAGG GAGCCATCGT GGTGGGCCAG GTGCTCAAGC ACCACATCAT
6241 CAACCCGAGA GGTCGACTGC ACCGGTTCCT GCACCGGCTC AGGAAGGTCA TCTTCTGGGG
6301 TAATCCGATG CGGCAGAAGG GCTTTGCCCA CACCGACGAG TGGATTCACC AGGTCGCTGC
6361 CTCGGACACG ATGGGCATCC TCGAGGACCG ACTGGAGAAC CTCGAGCAGT ACGGCTTTGA
6421 GGTCCGCGAC TACGCGCACG ACGGCGACAT GTACGCCTCC ATCAAGGAGG ACGACATGCA
6481 CGAGTACGAG GTGGCCATTG GCCGAATCGT GATGAGCGCT AGGCGATTCA TCGGAGGTAA
6541 GGACTCCGTC ATCGCCCAGC TCATCGAGCT TGGACAGCGT CCGATCTGGG AGGGAATCGC
6601 GATGGCCAGA GCCATCATCG ACGCCCTCAC GTTCTTCGCC AAGTCGACCC AAGGCCCGAG
6661 CTGGCCGCAT TTGTACAACC GCTTCCCGGC GGTCGAGTTC CTACGACGAA TCTGAGAAAG
6721 GAGGCGGGGT GAGCCTCAAC AACCACCACC CGGAGCTTGC CCCGTCTCCC CCTCACATCA
6781 TCGGCCCGTC CTGGCAGAAG ACGGTCGATG GTGAGTGGTA TCTGCCTGAG AAGACCCTCG
6841 GCTGGGGAGT CCTGAAGTGG CTCTCCGAGT ACGTGAATAC CCCGGGCGGG CATGACGATC
6901 CGAACCGTCT GGCGACGTTG ATCGCGCTCT CCGAGGCAGG TCTTCTCGAC AACGAGAACA
6961 TGTTCATCCC CACCGACGAG CAGGTACGCC TGGTCCTCTG GTGGTACGCA GTAGATGACC
7021 AGGGCCAGTA CATCTACCGC GAGGGCGTGA TCCGCCGGCT CAAGGGCTGG GGCAAGGATC
7081 CGTTCACCGC CGCGCTCTGC TTGGCGGAAC TCTGTGGCCC CGTAGCCTTT TCACACTTCG
7141 ACGCCGACGG TAACCCGGTC GGCAAGCCGC GTTCAGCCGC GTGGATCACC GTCGCGGCCG
7201 TCAGCCAGGA CCAGACGAAG AACACGTTCT CGCTGTTCCC GGTGATGATC AGCAAGAAGC
7261 TGAAGGCCGA GTACGGCCTG GACGTGAACC GCTTCATCAT CTACTCCGCA GCCGGTGGCC
7321 GTATTGAGGC AGCGACCTCG AGCCCCGCGT CGATGGAGGG TAACCGCCCG ACGTTCGTCG
7381 TCCAGAACGA GACGCAGTGG TGGGGCCAAG GCCCCGACGG CAAGGTCAAT GAAGGCCACG
7441 CGATGGCAGA GGTCATCGAA GGCAACATGA CCAAGGTCGA GGGCTCCCGC ACCCTGTCGA
7501 TCTGCAACGC CCACATCCCC GGCACCGAGA CGGTCGCCGA GAAGGCATGG GACGAGTACC
7561 AGAAGGTCCA GGCAGGCGAC TCTGTCGACA CCGGGATGAT GTACGACGCG CTGGAAGCGC
7621 CGGCCGACAC CCCGGTCTCC GAGATCCCCC CGCAGAAGGA GGATCCCGAG GGATTCGAGA
7681 AGGGCATCGA GAAGCTCCGC GAGGGCCTGC TCATCGCCCG AGGCGACTCC ACCTGGCTGC
7741 CGATAGACGA CATCATCAAG TCGATTCTGT CGACCAAGAA CCCGATCACC GAGTCGCGGC
7801 GCAAGTTCCT GAATCAGGTA AACGCCGCTG AGGACTCGTG GCTCTCACCG CAGGAATGGA
7861 ACCGGTGCCA GGTCGACCTG GCCAAGTACC TGGATAAGCA CGGCAGGGAG TTCGCTCCGC
```

SEQ ID NO: 1-continued

```
7921 TGCAGCGCGG TGACCGGATC ACCCTCGGGT TCGACGGGTC GAAGTCCAAC GACTGGACCG
7981 CGCTCGTCGG CTGCCGTGTC AGCGACGGCC TGCTGTTCGT CATCGACATC TGGGATCCCC
8041 AGAAGTACGG CGGGGAGGTT CCCCGCGAAG ACGTTGACGC CAAGGTCCAT TCGGCGTTCG
8101 CCCACTACGA CGTGGTGGCG TTCCGCGCCG ACGTGAAGGA GTTCGAGGCC TACGTCGACC
8161 AGTGGGGCCG GACCTACAAG AAGAAGCTCA AGGTCAACGC CAGCCCGAAC AACCCGGTGG
8221 CGTTCGACAT GCGCGGACAG CAGAAGAGGT TCGCGTTCGA CTGCGAGCGA CTCGAGGACG
8281 CGGTCCTTGA GGGCGAGGTC TGGCACGACG GCAATCCCGT TCTGCGCCAA CACGTTCTGA
8341 ACGCCAAACG ACACCCAACG AACTACGACG CCATCGCGAT TCGCAAGGTC ACGAAGGACT
8401 CCAGCAAGAA AATCGACGCT GCAGTCTGCG CTGTCCTCGC GTTCGGGGCG AGACAGGACT
8461 ACCTCATGAG CAAGAAGGCC CGTAGCGGCC GGGTGGTGAT GGTTCGATGA CAGCACCGCT
8521 CCCCGGTATG GAGGAGATCG AAGACCCCGC AGTCGTACGA GAAGAGATGA TCTCGGCCTT
8581 CGAGGATGCT TCCAAGGATC TCGCCAGCAA CACCAGCTAC TACGACGCTG AGCGCCGGCC
8641 AGAGGCCATC GGCGTCACCG TCCCGAGAGA GATGCAGCAA CTGCTGGCTC ACGTCGGATA
8701 CCCCAGGCTC TACGTCGACT CAGTCGCCGA GCGCCAGGCC GTCGAGGGTT TCCGCCTCGG
8761 CGATGCCGAC GAGGCTGACG AAGAGCTGTG GCAGTGGTGG CAGGCCAACA ACCTCGACAT
8821 CGAGGCACCA CTGGGCTACA CCGACGCTTA CGTTCACGGC CGGTCGTTCA TCACGATCAG
8881 CAAGCCAGAC CCGCAGCTCG ACCTGGGTTG GGATCAGAAC GTCCCGATCA TCCGCGTCGA
8941 GCCGCCCACC CGAATGCACG CCGAGATCGA CCCCCGGATC AACCGGGTGT CCAAGGCCAT
9001 CCGAGTCGCA TATGACAAGG AGGGCAACGA GATTCAGGCT GCCACGCTGT ACACGCCGAT
9061 GGAGACCATC GGCTGGTTCC GCGCTGACGG TGAGTGGGCT GAGTGGTTCA ACGTCCCGCA
9121 CGGTCTGGGC GTCGTTCCCG TTGTGCCGCT TCCGAACCGG ACCCGGTCT CGGACCTGTA
9181 CGGCACCAGT GAGATCACGC CCGAGCTTCG GTCGATGACC GACGCGGCGG CGCGCATCCT
9241 CATGTTGATG CAGGCGACCG CCGAGCTGAT GGGTGTCCCC CAGCGCCTGA TCTTCGGCAT
9301 CAAGCCCGAA GAGATCGGCG TCGACTCCGA GACCGGCCAG ACGCTGTTCG ATGCGTACCT
9361 GGCCCGGATC CTGGCGTTCG AGGACGCTGA GGGCAAGATC CAGCAGTTCT CTGCAGCCGA
9421 GCTGGCCAAC TTCACCAACG CGCTCGATCA GATCGCCAAA CAGGTCGCTG CGTACACGGG
9481 ATTGCCTCCC CAGTACCTGA GTACCGCCGC AGACAATCCG GCCTCCGCTG AGGCGATCAG
9541 GGCCGCTGAG AGCCGACTCA TCAAGAAGGT CGAGCGGAAG AACCTGATGT TCGGCGGCGC
9601 ATGGGAAGAG GCCATGCGGA TCGCCTACCG GATCATGAAG GCGGCGACG TTCCCCCGGA
9661 CATGCTCCGC ATGGAGACCG TCTGGCGAGA CCCGAGCACT CCCACCTACG CGGCCAAGGC
9721 CGACGCAGCC ACGAAGCTGT ACGGCAACGG CCAGGGTGTC ATCCCGCGTG AACGTGCTCG
9781 CATCGACATG GGCTACTCCG TCAAGGAGCG CGAAGAGATG CGCCGATGGG ACGAGGAAGA
9841 GGCCGCAATG GGTCTCGGCC TGTTGGGCAC GATGGTCGAC GCCGACCCGA CGGTCCCAGG
9901 CTCCCCGAGC CCCACGGCAC CGCCGAAGCC ACAGCGGGCC ATCGAGTCGT CTGGTGGTGA
9961 TGCGTGACCG CAGAGGAGTA CGCGGCGGCT CAAGCCGCGA TCACTGCGGG TCTTGCCACA
10021 TACGTCCAGA GGTTCGCTTC GCTCTTCGTC GGTCCAGCTC TCGCTGTAGG TGAGTGGCTG
10081 CGACTGCTGC AGGTGCTGTT CCCCGAAATC CAACGGCGGT ATGCAGATGC TGCCGCCTTG
10141 GGCAGGGACT TCTACGACTC CCAACGCGCA CTACACCACC CAGAGCTGCC CCGGAACGAG
10201 AGGTTCCGGG GAGAGCTTCG GTGGGAGTGG TTCGTCCAGA ACATGGAGCC CGCTCGAAAA
```

SEQ ID NO: 1-continued

```
10261 GAGATGTCGC AGGCCGACTC TCCGCCGAGT GCGACCTCTA AGTTGGCTCT GGCCGCAGTT
10321 CGCGAAGTGG AGATGGCAGC ACGCCGACAG ATCATCGGCG CTGTCAAGAA CGATCCGGCC
10381 CCGCAGATCG TGCAGGGCTG GGCGAGGGTC GCCACCGGGC GCGAAACATG CGCCTGGTGT
10441 CTGATGCTCA TCTCACGGGG TGCCGAGCTG AATCACAAGG CAACTTCGC CTACAGCTCA
10501 GCGGAAGCCG CAGGGCTCAA CCTCGATGAC GAGACCGTGA TCGACCTCTG GAACGAGTCC
10561 GGTCACGACC TTGAGAAGTT CCGCGAGGAG ACCAGAGAGG ACTTCGAGAA GTGGCACGCA
10621 GGGTGCGACT GTCTGGTGGT CCCGGTCTTC GATGTGCAGA ACTGCCCGG AAGAGACGCT
10681 GCCCTACGGG CGCAGCAACT TTGGATCGAA GCCAGCGACG AAGCTGACGA CCTCATTGCG
10741 TCAGGCAAGG CCCGCTCCAA GAACAAGAAC ACGGAGACGC TCAACGCGCT CCGACGCCGC
10801 CTAGCACGCG GCGAAATCAC CATGTCCAAC TACGCCCTCG CTGCGTAGTC CCTCGAACCC
10861 CAGGTGGGTT CTCTCAACAT GCCCAGGAGG CGAAAACACA TGTCCGACAA CCCCACTCCC
10921 GAGAGCACCC CAGAGGCCGA GACCCCGGAG GTCGAGAAGC CGATGGAACC GCAGGGCAAG
10981 GTCTTCGATG AAGCGTACGT TCAGTCGCTT CGCCAGGAGG CTGCAGCCGC TCGGGTGGCG
11041 AAGAAGGACG CCGTAGAAGC GGCAGAGGCT CGAGTGAAGG CCGAGTACGA GGCCAAGCTC
11101 GCTGAGCGCG ACACCGCTTA CACCGAACTG CAGAACCAGT TGGGACAGGG GTGGATTGAG
11161 CTGGAGAAGG TCTACCTCTC TCTCGACGCC AAGGTGCCCA ACGACAAGGT TCGGGCGTTT
11221 GTCGAGATCC TCGAAGGCAA CGACAGGGAC AGCATCGCTG AGTCAGTGAA GTCCCGTCTG
11281 GAGCTGGTCG GCGGATTCGG CAACAAGACC CCGAGTCCTG CGTTCGACCC GTCTCAGGGT
11341 CGCGGCGGTA AGCCGCCGAT CCCGCTGAAC GGTGACCCGA TCCTCGAGGC CATCAAGGCC
11401 GCTGTCGGGA TCAAGAAGTA ACCCACCCAA CAGATCTCAA GGAGAGATAA ACAATGGCAG
11461 TCAACCCTGA CCGCACCACG CCGTTCCTCG GCGTGAACGA CCCCAAGGTC GCGCAGACCG
11521 GCGACTCGAT GTTCGAGGGC TACCTCGAGC CCGAGCAGGC CCAGGACTAC TTCGCCGAAG
11581 CGGAGAAGAT CTCCATCGTC CAGCAGTTCG CCCAGAAGAT CCCGATGGGC ACGACCGGCC
11641 AGAAGATCCC GCACTGGACC GGCGACGTGA GTGCGTCGTG GATCGGTGAA GGCGACATGA
11701 AGCCCATCAC CAAGGGCAAC ATGACCTCGC AGACCATCGC CCCCCACAAG ATCGCGACGA
11761 TCTTCGTGGC CTCGGCGGAA ACCGTCCGTG CGAACCCGGC CAACTACCTG GCACCATGC
11821 GGACCAAGGT CGCGACCGCC TTCGCGATGG CGTTCGACAA CGCCGCGATC AACGGCACCG
11881 ACAGCCCGTT CCCGACCTTC CTAGCGCAGA CCACCAAGGA GGTCTCGCTG GTGGACCCGG
11941 ACGGCACCGG CTCCAACGCC GACCTCACCG TCTACGACGC GGTCGCCGTC AACGCCCTGT
12001 CGCTGTTGGT CAATGCCGGC AAGAAGTGGA CCCACACTCT GCTGGACGAC ATCACCGAGC
12061 CGATCCTCAA CGGCGCGAAG GACAAGAGCG GTCGCCCGCT GTTCATCGAG TCGACCTACA
12121 CCGAGGAGAA CAGCCCGTTC CGCCTCGGTC GGATTGTGGC CCGTCCGACC ATCCTGAGCG
12181 ACCACGTCGC CTCGGGCACG GTCGTCGGCT ACCAGGGTGA CTTCCGCCAG CTCGTCTGGG
12241 GCCAGGTCGG CGGCCTGTCC TTCGACGTGA CGGATCAGGC GACTCTGAAC CTGGGCACCC
12301 CCCAGGCTCC GAACTTCGTC TCGCTGTGGC AGCACAACCT CGTCGCAGTC CGAGTCGAGG
12361 CCGAGTACGC CTTCCACTGC AACGACAAGG ACGCGTTCGT CAAGCTCACG AACGTGGACG
12421 CCACCGAAGC CTGATCCAGG CTTGACATCC ACCGGGAGGG GGCTCCTTCG GGAGCCCTCT
12481 CCTGATGTGG AGCAGGAAGG ACCACATGCG AATCCAGTCC ACCCTCAACG GCGGTTTCGC
12541 CGAGGTTTCC GAGGAGTTCG CCAAGCAGTT GATCGCCACT GGCGGCTGGA AGGTGCCCCG
12601 GAAACCGCGC AACACCAAGA CCAAGACCGC TCCTGAGGAG CCCAAGAACG AGGAGTAACC
```

SEQ ID NO: 1-continued

```
12661  CGTGGCCTAC GCGACCGCCG AAGACGTTGT GACGTTGTGG GCCAAGGAGC CTGAGCCCGA
12721  AGTGATGGCG CTGATCGAGC GCCGGCTCCA GCAGATCGAG CGCATGATCA AGCGCCGGAT
12781  CCCCGACCTG GACGTGAAAG CCGCTGCGTC GGCGACGTTC CGGGCCGATC TGATCGACAT
12841  CGAAGCTGAT GCTGTTCTGC GCCTCGTGCG TAACCCGGAG GGCTACCTCT CGGAGACCGA
12901  CGGTGCGTAC ACCTATCAGC TCCAGGCCGA CCTGTCGCAA GGCAAGCTCA CCATCCTCGA
12961  TGAGGAGTGG GAGATCCTCG GGGTCAACTC CCAGAAGCGC ATGGCGGTCA TCGTCCCGAA
13021  CGTGGTGATG CCGACGTGAG CGCGAGCGAC CGACACCGCG CCCCGATTGT CTATCCGCCT
13081  GGCACTCAGG CGGTTACGCC GGATCGGGTC AACGCGTTTG ACTGCGATCA CGAAGCTGAT
13141  CCTCCGGTGT GCCGGTGCGT CCACGACTGG CGCATCGAGT GGGGAAACGT CAAGAAGGCC
13201  ACCGCCAGAT CACGGTCGGC GGTGCTCTGA TGAGCCTCCT CGACACCGGT GCCCGGTACC
13261  AGACCTGCAT CGTCTACCCC GAAGAGATGG TCATCGACTC CGATGGCAAC AAGCGGACCA
13321  GGCCGTCGAA TACCGGCATC CCGGCCATCG CACGGTTCCA GGTAGCCAAC CAGTCTGGTA
13381  CGTCGGCACG ACGTGCTGAG CAGGACAACG AGGGGTTCGA GACCGAGAAG GTCTACCGGA
13441  TGCGGTTTCC CCGCTCGTTC ACCAAGGAGC ACGGCATCCT CGGGGCCCAG TCCCAGATCG
13501  AGTGGCGAGA CCAGCGGTGG GCGCTCTTCG GAGACGCCAC CGTCTACGAC TCATCCCCTG
13561  CGTTGGCGCG GGTCGACTAC ACGATCAAGA GGTACTGATG CCAAGGTCT ACGCGAACGC
13621  GAACAAGGTC GCGGCCCGGT ACGTCGAGAC GAGGGACGCC GTCCGAGACG AGCGGAACAA
13681  GGTCACCCGT CGAGCCAAAG CCAATCTGGC GCGGCAGAAC TCGACCACCC GCATCACCGA
13741  CGAGGGCTAC TTCCCGGCCA CCATCACCGA GCAAGACGGC GATGTCGACT TCCACACGAT
13801  CCTCAACGCG CCCAACGCGT TGGCGCTTGA GTTCGGCCAC GCGCCGTCTG GCTTCTTCGC
13861  TGGCACCGAC ACGAAACCAC CGGAGGCCAC TTACATCCTC ACCCGAGCCG CCATCGGCGG
13921  CACCGTCTCA TAAGGAGGTC ACATGGCGCG AATGCCTCGC GTCCAGGCAG TAGCGGCCCC
13981  GATCCTCCGG TCAGACCCCC GACTGGAGGG AGTGACGGTC ACGACATGGG TTCCAGACGT
14041  GGACTTCCGA GAGTTCCCGA TGATCAACCT CCGCCGCATA GGCGGGACGA GGAACCCCAA
14101  CGCACCGACG CTGCACACGC TGCCGGTGGT CGAAATGACC GCCTACACCA GAGACGGTCT
14161  CATCGAGACT GAGGAGCTGT ACGAGACCGC GCTAGAGGTT CTCTACGACG CGGTGGAGAA
14221  CGGAACACAA ACTCCCGCAG GGTATTTGAC CTCCATCTTC GAGACGATGG CGCCACTCA
14281  GTTCAGCTCC CTCTACCAGG ACTCCTGGCG CATCCAGGGT CTGATCAGGC TCGGCGTCCG
14341  CAGACCGAGA ACCACCCTCT AACCGAAAGG TAAAGCCACA TGGCTGAAAA CGACGACGCA
14401  GTGTTGACTG CGGCGGTCGG CTACGTGTAC GTCGGTGCTG CAGGCACCGC TGCTCCTACG
14461  CCGGCCTTGC TCAAGACCAT CGACCTCAGC AAGCCCGAGA CCTGGACCGG TGCTACCGGT
14521  TGGACGAGCG TCGGCCACAC CAGCCGAGGC ACGCTCCCTG AGTTCGGCTT CGAAGGCGGC
14581  GAGTCCGAGG TCAAGGGCTC CTGGCAGAAG AAGAAGCTCC GCGAGATCAC CACCGAGGAT
14641  CCCATCGACT ACGTCACGGT CCTACTGCAC CAGTTCGATG AGCAGTCGCT GGGTCTGTAC
14701  TACGGCCCCA ACGCCTCTGA GACTCCTGGT GTGTTCGGTG TGAAGACCGG CCAGACCAAC
14761  GAGAAGGCCG TGCTGGTCGT GATCGAAGAC GGCGACATGC GCCTGGGGCA TCACGCCCAC
14821  AAGGCTGGAG TTCGCCGCGA CGACGCGATT GAGCTGCCCA TCGATGACCT GGCTGCGCTG
14881  CCCGTCCGGT TCACCTACCT GGACCACGAA GACGAGCTGC CGTTCTCCTG GATCAACGAA
14941  GACCTCTTCA ACGTGCCCGA GGTTCCCGAG GGCTGATCCC AACTTGACAG CCACCCGGCT
```

SEQ ID NO: 1-continued

```
15001 GTCTACCCCG GAGGGGGAGG TTTCCTTGGC GGGCCTGGCC TCCCCCTCCT CCCGCCACTC
15061 ACAGACCCGC CGACACTGAA AGGTTCGCCA TGACAAACGT ATTCACCATC GACGCATTCC
15121 GCGAAGAGGT CAAGAAGAAG TACGCTCCGG TCCTCATCGG CCTGTCCGAC GATGTGACCG
15181 TCGAGCTGAA GCCGCTGCTG AAGCTGGGCC AGAAGGCCCG CGAAGCGGTG GTCGAGGTGT
15241 TCAAGGAGTT CGCGGACATC CCCGACCTCG AAGAGGACGA CGACGACGAG TTGGTCGATG
15301 AGTACTCGCT CCAGGTCTGC GACATCATCG CCAAGGCGTT CCGGCTGATC GCCACGAAGC
15361 CCAAGAAGCT GATCGCCGCC TTGGACGAGG AGCCGGATCC CCGTATCCGC GCAGAGCTGT
15421 ATGCAGCGGT ACTCAACACC TGGAAGCGAG AGACGCAACT GGGGGAAGCC GCGCCCTCGC
15481 CGAGCTGATC GACAAGTTCG GCGGGGCGAT CCTCGCAGAC CTGCTCCAGT ACTACCGGGT
15541 AGACCTGCGC GACCTGTTCC GCGACGAGGA TCCGCTTTCG CCGAGATTCG TTCTGTCCCT
15601 GGTGCTCTGC CTTCCCAAAG ACGGCGCGTT CTACGCAGAA CGTCGTGGTG GGCAGCAGTA
15661 CCGGGGCTGG ACCGAGGACC GCTACGCGCT CGCGGACATC TACGACGCCA TCCAGGCGGG
15721 CAACCACATC CTGCTGCTGG CGAATCGTGA TCCGAAGAAG CCAAAGCCCA AGGCACCCAA
15781 GTCATACCCG CGTCCCGACG ACCTAGAGAA GACCACACCG AAGCCGGGTT CGTTCGCCGC
15841 AATGGTCGTG CGAGCGAAGA AGGCGGCTCG AGAGAGAAGG GAAAGGGAGG AGGAGAGTGC
15901 CGAATAGTGC TGGCGTAGAA GTCGCCCGGA TCTCGGTCAA GGTCAGCCCG AACACCAAGG
15961 AGTTCCGCCG GGAACTCAAG ACCGAACTCG AGAAGATCGA GCGGGAGCTT AAGGGCGATG
16021 TCGAGATCAA CGGTCATCTC GATGCGGCCC AGGCCAAGGC CGACTTCAAG CGCATGATGA
16081 TGCAGCTCAA GACCGAAGCT GCCAAGGGCG TTCACGTCCC GGTCGACGTA ACCGTCGACA
16141 AGAAGAGCAA GAAGGGAGGT CTCCTCGGAG GTCTCCTCGG CGGCAGCCGG GGGCTCGGAG
16201 ATCTAGGCGA TGACGCCGAG AAGGCGTCGT CTCAAGTACA ACACCTTGGC AAGTCGTTCC
16261 TGGGCCTCAC ACGAGCCGCC TGGATAGGCG TAGGCATCGT CGCCGTAGCA GCTCCGCTGG
16321 TCGGCATCGT GGCCGGTCTG CTGGCCGGTC TGCCGTCGCT GCTGTCTGCG TTCGGAGCCG
16381 GCGCTGGCGT AGTCGCGCTC GGCATGGACG GCATCAAGGC AGCCGCCTCG ACGCTGGCCC
16441 CGACGCTGGA GACGGTCAAG GCCGCTGTCT CCTCGACGTT CCAGCAGGGA CTCACCCCGG
16501 TGTTCCAGCA GCTCGGCCCG ATGCTGACCG CGATCACCCC CAACCTGCAG AACGTGGCCT
16561 CGGGCCTCGT GAACATGGCC GGGTCGATCA CCGACGTGAT CACCCAGGCT CCTGGTCTGC
16621 AGCAGATCCA GAACATCCTC ACCAAGACCG GAGAGTTCTT CACGGGCCTC GGCCCTGTGC
16681 TCGCTACCGG CACGCAGGCG TTCCTGACGC TGTCCAACGC CGGCGCGAAC TCGTTCGGCA
16741 CGCTCCTGGC TCCCCTGCAG GAGTTCACCA ACGGCTTCAA CGACATGGTC AACCGAGTCA
16801 CGTCCAACGG CGTGTTCGAG GGTGCCATGC AAGGGCTTTC GCAGACGCTG GGCAGCGTCC
16861 TCAACCTGTT CAACCGGCTC ATGGAGTCCG GTCTGCAGGC GATGGGACAG CTCGGCGGTC
16921 CGCTGTCGAC GTTCATCAAC GGGTTCGGAG ATCTCTTCGT CTCGCTGATG CCGGCGCTGA
16981 CTTCGGTCTC TGGTCTGATC GGCAACGTCC TCGGGACGCT GGGCACACAG CTCGCTCCCA
17041 TCGTCACGGC GCTCACGCCG GCCTTCCAGA CGCTGGCGAG CACGCTCGGC ACGATGCTCA
17101 CCGGAGCCCT CCAAGCTCTG GGTCCGATCC TGACTCAGGT CGCTACGTTA TCGGCACGA
17161 CGCTGAACAC GGCGCTGCAG GCTCTCCAGC CGATGCTGCC GTCGCTCATG CAGAGCTTCC
17221 AGCAGATCTC CGACGTACTG GTGACCAGTC TGGCCCCGCA CATCCCGGCC CTGGCGACGG
17281 CCCTCGGCCA GGTCGCAGGC GCGGTGCTGC AGCTCGCTCC GACGATCATC TCGACGTTGG
17341 TTCCGGCGTT CGTTCAGTTG GTCCCAAAGG TCGCTGAGCT AGTTCCGACC ATCGTCAACC
```

SEQ ID NO: 1-continued

```
17401 TGGTCCAGTC GTTCGCCAAC CTGATGCCGG TGGTTCTGCC CCTGGCGCAG GCTCTGGTCA
17461 GCGTTGCTGG CGCGGTGATT TCTCCATCGG CAGGTGGGTG CGGCGCGCTC ATCGGCGCGC
17521 TGGCGAACCT CACGGAGATC ATCTCCAACG TCATCAAGAA GGTGTCCGAG TGGGTCAGCA
17581 GCTTCTCCAG CGGAGCCCAG CAGATCGCTG CGAAGGGCAG GGAACTGCCG GGGATGATCC
17641 AGTCGGCTCT CGCCAACCTG ATGGCCATCG GCCTGCAGGC CGGTAAGGAT CTCGTCCAGG
17701 GCCTGATCAA CGGCATCGGC GGGATGGTCA GCGCAGCGGT CAACAAGGCC AAGGAGCTGG
17761 CGTCCAGCGT GGCGGGTGCA GTGAAGGGCT TCCTGGGCAT CGAGTCCCCG TCGAAGTTGT
17821 TCACCGAGTA CGGCCAGTTC ACCGCCGAGG GATTCGGCAA CGGCATGGAG GCAGGGTTCA
17881 AGCCCGTCAT CGAACGGGCC AAGGATCTCG CGGCTGAGCT GTCCAGGGCG ATGGAGTCGG
17941 GCACCGACCC CTCCGGGATT CTCGCGGGGC TGGATCAGAA TGAGCTGAAG CAGATGCTGG
18001 CGGCTCTCGA AGAGGAGCGC AAGCGACTCA AGGTCGAGAA GAACGGTATC CCCAAGGGAG
18061 ACAAGGCAGG CCGAGAGGCG CTGCAGAACC AGCTCGACCA GATCCAGGCG CAGAAGGACA
18121 TCCTGTCCTA CCAGCGTGAC CGCATCAAGA ACGAGTCTGA GTACGGCGAC ATGGCCGGCG
18181 AAGACCCGTT GGTGAAGGCA GCCTCCGGGC TGATGAGCGC ACCGGTCGAC TTCGCGAAAG
18241 CGACTGGCAA GCAGTTCCTT TCGGACATCG GCATCAGCGG AGATGGGTTC ATCTCGAAGG
18301 CCATCACCGA GGGCATCCAG TACATCTTCC AGATCGGCTC TGTCGATGAG GCGCTGTCGA
18361 TCAAGGACCG CGAGGAGTCG AAGAACGCGC TGTCCGTCGT TGGCCGCTGA CTTGACATCC
18421 ACCAGGAGGT AAGCATTGAT CACCGACACC ATCGTTGAAC TCGAGGGTGT CAATGGTGAG
18481 CGTTTCAACT TGACGACCGG TGACCAGGGT GTGTACCTGG CCACAGACGT GGAGGGTTGT
18541 TTCTACGACC CTCCCGTCAA GGTCGTTGTT GAAGAGCCGG GGAACTACCC CGGCGCTCGC
18601 TACTTGTCCC ACCGAGCCCT GAAGCGAGAC ATCGTCTTTG GGTCGTCAT CCTCAACGAC
18661 GCGAAGCAGG GGCCGCGCTC CTGGCTGTCG CGAGACTCCG AGTGGCGCAA GGCGTGGGCG
18721 TTCAACCGCA CCTGCAAGCT CTACGTCACC ACCCCGGACT CCGGTACCCG CTACCTGAAG
18781 CTGGCGCTGT TCGAGTCCCC CACCGTCAAG ATGGACACCG ACCCAAGAGG TAAACCCCTT
18841 GAGGTCACGG TGATGTCGTG CATCGCGTAC GACCCGTTCT GGTACGAGGA CGACAAGGTC
18901 TTCTCGGCCA AGACCAAGAC CGACACCCGG TTCGACCCGT CGTTCTGGAC GCCGCCGTGG
18961 CCGTGGGAGG AACTGCCCAA GGAGACGCTG CGGATCAAGG TCGGCCGCGA GCAGGGTGGG
19021 CTAAACCCCA CCGACCAGTA CATCTTCCCG AAGTGGACCG TTCCCGGCTC CACCGAGAAG
19081 GTGCCGAACT TCCCCTGGCC GTTCCCCCCG AACGTCCCGA TCCCGTGGGA GACAGCACCG
19141 TTCACTCAGT TCGTCATCCC GGACTACTCG TTCGAGGATG AGGAGTTCCG CAACCGCCGG
19201 CTCAAGACGC CGGGGTTGAT CTACGGCGAG AACTGCGTCA TCGACACCGA CCGGCGCGAG
19261 GAGCAGATCG CTTCCGAGTC GGGCTCCCCG GTGTGGGCTC GGATGAACGG TGTCCGGTTC
19321 CGCAACTCGA TCCCGCCCTA CACCGAAGAG GCTGAGTTCG TCATAGACGC ATCGGGATGC
19381 GCTCCGGGAC AGGTAGTTAC CCTCCGGCTC ACGAGGCCGT GGTCGCGCTG CTGGGGGCTA
19441 GAGTGAGTGG TCTGACGAGC GTTCGTGAGG CCGAAGATCT CTGGCAGAAG ATCCAATTGC
19501 GGCGCTGCAA GCGCGAGCAG GAACGGCTCA AGCATCCCGA CGTAGAGCTG CGCGATGGCG
19561 ACTTCCGCCT GCGCGGCCTG GTCGCTGGCG AGCGGGTGCT CGAGTGGGAG TTCATCGAGA
19621 ACGAGACTGG CACCTGCACC TTGCAGCTCT CACTGAGCCA TTACCTGGCG AAGTGGGTGA
19681 TGGACCACCG GGGTCGAGCA AAGCGCAACG TCATCATCAA CATCGAGAAG CAAGGCGCTC
```

SEQ ID NO: 1-continued

```
19741 GATGGACCGG GATGATGGAC CACTACCGGG TCATCAAGAC CGACGCAGGG GACGCCTACA
19801 TCGAGATCGT GTTTTTGCAC GACTTCGAGC AGACCAAGCA TATCCGGGTA TGGTGCAACC
19861 CGTTCCTACG CCCCGAGCTG CAGTTCCCCA AGGTGTGGAT CATCTTCGGG CCGGCCAAGT
19921 GGTGTTTGCT GGTGACACTG TTCGTCAACC TGCTCAGGCT CGAGACGAGC TTGTGGACGC
19981 TGCCTGATGA CCCCACGGAC ATCAACGAGT GGATGGGTCC GAGCTTCAAC CCAGCAAATT
20041 GGCGGAACAT CGTCAAGCCG TTCCCGTTCC TGGCCGACAA CTCACCGGTC ACGATGGTGT
20101 TCAGCCGGTT CGGGACGTTC TACGACACCG CCAAGAAGAT CCTCGAAGAC CATCAGCTCA
20161 CGCTGACGTG TCGTCGGTAC ATCAAGGACC GCGACCCGCA TCCGTTCGAA GATCTCAAGG
20221 GGCTCTGGGG AATTGATCCT GTCAAGACC TGCTGCAGAA GATCCCGCTC CGGGACGGCT
20281 GCGTGGTCTG GGACATCGAG GACAACTCAG GTTGGGGCAC TCAGACCGCG TTCGGCGGTT
20341 CGTGGCTGAC CGGGTTCGTC CGAGGGATGG TCCAACTGGC CGGCGACGGC CAGGTCGAGG
20401 GCGTCGATGT GTTCACCGGG GACTACACGT TCCCAGGCGA GTACTACTCC CCCTGGTTCA
20461 TGGGCACCAG CCCGATAGCA CCCCACGTCG TGTTCGAAGA AGGACCGCTG ACCGGGATCA
20521 AGTCGTCGGA GTTCTCGTAC TACGAGGCCA CCGACACCAG CTTCCTGGCT GGTGGACAGA
20581 GCGCACCTGG CATCAACGAG GGCATCTCGG CCCTGGTGAA CATCGGTGGC GACCTGCTGA
20641 CCTCGTTCAT CAACAGCCAG CTCGCCGCGC TCGGCGCGGT CGGTGGAGCG ATTGACCTCC
20701 CGCCTCTGGG CGGTCTGCTC GATGCGGTGT TGCAGCCTCT GTACTCCGAT GTGTTCGGCG
20761 CGTTCATGGA AGTTCCGACT CTGCGTGCGA TGGGCATCTC GCTCCCGATC TCCGGGCTCG
20821 AGGACATCGT CACCGGACTG GGCGACTTCC ACTACTTCGA GAACATGGCC GACGGGGCGA
20881 TGAAGGCGTT CACGCTGTCA GCGTTCGCAG CCATCGCATC GCAGATCCAC AAGACGAGGG
20941 CTCGAACGAC CCACACCCTC AAGGTGTCTG ACGCCGCTCC GTACATCTTC GCGCCAAAGC
21001 CCTACGGGCA CTGCTGGATC GGAGATCGCG TCGGCACGTC GGTCCTCGGC TACCCGGTCG
21061 AGCACCAGTT GTTCGTGGAG CGCATCCGCA AGGTGAAGTA CCGCATCGAC AAAGACGGCA
21121 TGAAGCCGTT GGAGATCGAG ATCGGTTACC GCGAACCGAA GAACCCAGCA CTACACATCC
21181 TCGAAGAGAT CAAGCGCGTC AACGGCGCTC TTGGCACTGC GGGGATTCTC TAAACCGAAA
21241 GGCACGCCGC ATGATTCCCT CACAAGAGTC TCACAATCCG AACGACCCGC GACAGCACGT
21301 CATGTGGGCG CTACGCAATC TCCCGATGAT TGCTGGCGTC GGGGCGATCA CGCATCCGGG
21361 TTACCTGGCG GATTGGTCAG AGCACTTGTG GAAGTGCGGC TTTCGGCACG TCGACTGGCT
21421 CCGGGAGCTG GCTGATGAGG ACGGCAACAT CCACGTCAGT CAGCTTCCTG ACCAGGAGAT
21481 CAAGTTTCAG CAGCCCTTCC GGGGCCAGCG AAGCGACTAC AACAACGCAG CTCGATGGGT
21541 CGGCAAAGAC GATCCTGACC CAGAGCCCGT GCGTATTCCA GACATTCGCA AGCTCACAGA
21601 CCAGGAGAAC AGAGCGATGA TCGCGCAGTA CGAACGAGAC GGTTGGATCA AGGATGGATC
21661 CCCCGGCCCA GCGATAGCCG AGGTCGTGGA GTGACCCCGT TCAACCCAGA CTCCATAGGC
21721 GACTACGTGA CACTGCTCGG CGTTGCGTTC CTGACCTTCT CGGTTCCCGC ATGGTTCACC
21781 GGACGAGCAC GCAAGCACAG CAGTGACATC GGCGAAATCA AGGAACAGGT ATGTAACACC
21841 CACGACACGA ACCTGCGCGA TGACCTCGAC AGCGTCAAGG CAGACATCAG CGACTTGAAA
21901 GAGATTGTGT TGCAAGGGTT CCACCAGGTG AACGAGTCGA TCAACCTCGA GCGCCGTGAG
21961 CGGATCGAAG GAGACCGCCG AAAGGAGGTT GCGTGACCTA CCCCACCAAC CCACTAGAGG
22021 CCATCGGCGC TGACGGCGCA TTCGAGATCG GTGGGGGCGA CTGGAGCTTC GGCCAGGACT
22081 ACACCGAACA GGCCATCCGG GCTCTGTTCA CGATGCCAGC GGTCACGATG GAGAACGCTC
```

SEQ ID NO: 1-continued

```
22141  TCGGCCTGCT CGAAGAGCAC CTGCTGAAGC TGCCTCTGGA GGCGCTGCAG GGCTTCAAAG
22201  ACATGATCCC GGACTGGGTC GAAGGAGCAT TCGACACGGT CACCGGCGCT GTGCAGGCGA
22261  TCATGAACGC GCTCCAAGAC GGCCCGCTGT TCCTGAAGTT CGCCGAGTTC CAGCTCTTCC
22321  TGCAGCGTCT GCTGAACAAC CCGGCCGAGG TCATCGGCGA GATCCCCCAG ACGTTGATCG
22381  ACGGCCTACA GGACGCGCTC AACACCGTCA ACAACACCAT CCAGACCATC GTGGACATGC
22441  TCCTGCAGGC GCTGGGCATC ACCCCGGAGG GGGAGCTGAT CGACCGGATC TTCGACCTGA
22501  GCGATGAGAT GGAGTGGCTG CAGACCGCAG CCTCGAATGC AGCTACCGGC ATCCAGGACA
22561  CCTGGAACAA GTTCTGGGGA GCCCTCACCG GGCGCGTCCC AGACCAGGAC CAGACCGTCG
22621  CTGAGCCCGC CGAGCGTATC GGCGAGCTGG CCGGCACCAC GTCTGCTAAC TCGTCTGCCA
22681  TCGCGGAGCT GCAGCGTCGA CTGGACAACC AGCAGAACGC TGGCGGCGTG GCCGGCGGTG
22741  ACGACTTCGA GCGACTGAAC ATATCCGGTT GGGACATCAG GTATTCCAAC GGATCCAGCG
22801  GCCGAGGGTA CTACCGTGCC GACGGCCACC AACTGGTCTG GATGGACGAA GGCAACCAGC
22861  AGAACACCGC GACGTTCGTC CGCACCAACC CCGCAGACGA GAAGACAGCC ACCGACTACC
22921  AGAAGATGAC GTTGGTCGTC GGGACTATCT CCGGTGAGGT ACAGACCGTG TTCCCGCCGC
22981  AGGGAGGTTC GCACACCCGG CTATGGGTCC GCGTCAACGA CAACGCTCCG ACCGTCGGCA
23041  TCACCGACGG CGTGTTCGTA GAGATCGGCG GCGTATCGAA GGCCCAGATC GGCTACCGCC
23101  GCAACGGCAA TGACACGTTC GTCGGATCTA TGGTCGACTG CACCTGGGGT GCTGGATCGA
23161  TCTTCGCTCT GACCGCCGGC ACGGCCAACG GTGCTGAGAA GTTCGAGGTC TCGAAGAACG
23221  GCCCCGTGCT GGCCACATGG TCGGACGACG GCGTCGTCTC CGCGATGGGT GCGAACTACC
23281  GCCGCTGGGG CTGGGAAGGC CAGGCTCGTA ACCGCAACCT CGGCCAGGGC ACTCCGAACT
23341  CGGTCACCCG AGTGACGATC ACCGACAACG ATCCTACCGG CGCAGGCGGT GGAGCTGTCA
23401  ACGTCGGAGG AGATGTCGTA GGTGTACTCC CCATAGAGAA CGGAGGCACC GGAGCTTCGA
23461  CAGCTTCGGC AGCCCGTACC GCTCTCGGAA TCGATGACCT GGTCGAAGAT ATGTCCGACG
23521  TAGTTCGTGG ATCCGTCGAA GGACTCCCGT TGATACCGAA GATCTGGGTA GGAACAGAAG
23581  CTCAGTACAC GGCTCTCGCC ACCAAGGATC AGTCCACGCT ATACTTCAGG ACCGCTTAAT
23641  GACTGGTATC TCGTTGGGTG TCAACGACAT CCGCAACCTC TCGATATTCT TAGGCGTCAG
23701  CAACAAGATA TTGAAGGTCA GTCTAGGCAC AGAAAAGGTC TGGCCTGCGT TCACCCCGGT
23761  GCTGACCACG TTCGCCACGG TCGGCACGTA CACCTACAAC ATCCCCGACG GGGCCAAGTT
23821  CATCGACGTC ATCCTCCTCG GAGGAGGCGG CGGGGGTAAA GGCATGGCCC TGGCTGACGG
23881  CTGGGGCAGA GGTGGAGACG CCGGAAGCTG GGCTATCGTC ACTCTCGAAC GCGGGGTACA
23941  CATCCCGTTG TCGACCAAGA CGATCACCGG GCTCGTCGGA GCTGGAGGCG CAGCGGGAGC
24001  TGGCTCTGTA TTCTCAGGCA AGGCCGGAGG CCCTGGAGGA AACACCACGG CGTCCGCTGT
24061  CGGATGGTCA GGTTTGACCG CAACCGGCGG TCCCGGAGGC TCTGTGATCG ACATCCTCAG
24121  CGTCGCCGGA AAGTCGCCTG GAGATCGGAC CTACAACGAC CAGCTCTACA TAGGCGGCGC
24181  ACAACAGAAC TCAGCTGGCG GGAACGGCAA TGCTCCTGGC GGCGGCGGGG CTGGTGCCCA
24241  GGTCTCCGCA CAGAGCGGCG GTGCTGGCGC TCGCGGCCAG GCGTGGTTCT TCGCGTACTG
24301  ACAAGAAACC CCCCTCTTTA GGACTCAGTG TCCTTGGGAG GGGGCTTTT TGCGTTTCAG
24361  GAGGTCTTGG CCAGCTTGGA CATCGCCTCA GCGATAGCCT CGTCGCGGGC CTCAGACGCC
24421  ATCTGGTACT TCATCGCCAT CCTAGGAGTC GTGTGACCGA GACGGGCCAT CAGCTCCTTG
```

SEQ ID NO: 1-continued

```
24481 GTCGTCGCAC CTGCCTGAGC GGCGAACGTA GCGCCGACAG CGCGGAGGTC GTGGATGCGG
24541 AGTTCCGGCC GACCGATCTT GGCGTAGCCA CGCTTCAGCG ACTGGGTGAA CGCGGACTTC
24601 GACAGCCGGT TGCCCTGCGT CGTGGTCACC AGGAATGCCT CGGGGCCCTT GTTCATCTTC
24661 GTACGGTCCT TCATGTGCGC TCGGATCATC TCCGCGACGT GAGGCGGAAC CGTCACAGGA
24721 CGCTTCGACC GGACGGTCTT GGCGTTGCCA ACGACGATCT TGTTCCCCAC GCGGGAAGCG
24781 CCACGGCGCA CCCGGAGCTT CATCGTCATG CCGTCGTCCA CGATGTCCTI GCGGCGAAGC
24841 TCGATCAGCT CTCCGAACCG GAGGCTCGTC CACGCCAGGA TGTATGCCGC GATCCGGTAG
24901 TGCTCGAAGA TCTCAGCGGC GACGATGTCC AGCTCCTCAG GCGTCAGCGC CTCTACGTCG
24961 CGCTCATCGG CTGCCTTCTG CTCGATCCGG CACGGGTTCT CTGCGATCAG CTTGTCCTCG
25021 ACCGCTGTGT TCATCACCGC CCGGAGGACG TTGTAGGCAT GCCGGCGGGC AGTCGGGTGC
25081 TTCCTACCCA TCCCGGCCCA CCACGCACGC ACCAGAGCTG GCGTCATCTC TGTGACCGCC
25141 ACTTCACCTA GCACCGGGTA GATGCGGCGC TCCGCGTGCC CGCTGTACAG ATCCCGGGTG
25201 CCGTCTGCGA GGTCGCGCTC CACGAGCCAC TTCCGGGTGT ACTCCTCCAG CGTGATGGCG
25261 CTGGCGGCTG CCTTCTTCGC CCGGTCCTGT GGAGGGGTCC AGGTCTCCAT CTCGATGAGC
25321 CGCTTCTCGC CCGCGAGCCA GGCTTCGGCG TCCATCTTGT TGTCGTAGGT CTGCAGCGCG
25381 TAGTACCTCA CACCGTCCTG CGGGTTGACG TATGAGGCTT GGATCCTCCC GCTGCGCTGA
25441 GTCTTCAGCG ATCCCCATCC GCGACGTGCC AACTAGGTCT CCTCTCGTCG TGAACAAGGC
25501 TACCGGGTTG CAACTCCTGT GCAACTCTCA GGCTTCAACG CGCTTCTACG ACCTGCAATT
25561 TCTTTCCACT TAGAGGATGC AGCCGAGAGG GGGTAAAAAC CTATCTTGAC CGGCCCATAT
25621 GTGGTCGGCA GACACCCATT CTTCCAAACT AGCTACGCGG GTTCGATTCC CGTCGCCCGC
25681 TCCGCTGGTC AGAGGGTGTT TTCGCCCTCT GGCCATTTTT CTTTCCAGGG GTCTGCAACT
25741 CTTGTGCGAC TCTTCTGACC TGGGCATACG CGGTTGCAAC GCATCCCTGA TCTGGCTACT
25801 TTCGATGCTG ACAAACGAAT AGAGCCCCCC GCCTGCGCGA ACAGACGAGG GGCATTCACA
25861 CCAGATTGGA GCTGGTGCAG TGAAGAGAAT AGACCGGGAC AAGGTTGCAC CGGGAGTTGC
25921 AGCGGTCGGA ACCCTCGCCG TCGGCGGGCT GGCGTTCGCC CTGTCGTTCA CGGCTCTCAG
25981 CGAGCTGGCT GCGGCCAACG GGGTGGCCCA AGCAGAGATG GTGCCCTTGG TGGTCGACGG
26041 CCTGACGCTC GTCGCCACGG TCGCCACAGT GGCCCTCAAG CAGAACAGTT GGTACGCGTG
26101 GTCGCTGCTG ATCCTGTCCA CCGTCGTATC GGTGGCCGGC AACGTGGCAC ACGCCTACCC
26161 CCACGGCATC ATCGCGATGG TGATCGCTGC GATCCCTCCG CTCTGGCTAC TGGCGTCGAC
26221 CCACCTAACC GTGATGCTGG CGAAGCAGCA CTCGGAGCAC GCCGAAGTAC CTGTCTCGCG
26281 GCCAGAACCC GCGCCTCGGG GCCTGGAGCC CGCTGCCGCT TGACTGCGCC CGACCGGGAC
26341 AGAAATACAT AGAGAACCTA TGGATGTAGG AGGCACAAAA AAATACCCCC CGAGCCAGCC
26401 CGAAGGCCAG CCCAGGGGGC ATGGTTCTGC TTCAGTAGAC CTTGCGAGTC CGACCCGAGT
26461 TGATCATCGC CATGATGACC CAGACGGGCA ACCACATTCC GCAGGTGATG AGCGAAAGCA
26521 ACAGGTGCAT CGCGTGGTTC GTCCTGACAG GCATGACAGT GGGCTGCGGC ATCGGAGGAG
26581 GCGCGACCGG GTACGGCGAG CCCGCGTACC ACTGAGGTCG ATCTTGTTGG GGCGGATACT
26641 GATTGGTCAT CCCGACAGCC TACTTGCCGA TGGGTCGCAT CAGCTCCTCG ACCGACTCGC
26701 GCTCCACGCG GATCAGCCGG GGACCGAGCC GAACGGCCTT GAGCCGGCCG TCGGCGATGT
26761 AGTTGCGGAC GGTCTTGGTG CTGACACCGA GGTAGTCAGC GGTCTCCTGG ATGGATGCTC
26821 TCGGGGCAT CAGCGCGGTC CTCCGTGCTT CATCGGTTGT CTCCCGAACC CTGGATCACG
```

SEQ ID NO: 1-continued

```
26881  CCACGATCCT TGCGGCTCTG GAGCTTGTTG AGGTTCCTCT GGGTGACGGT GCTCAACCAG
26941  ACATCGAGCT GGTTGGCTAG CTGGGCGACG TACCACATCA CGTCTCCGAG TTCCGCCTGG
27001  AGGTCGTCTC GGTTCTCCTG GGTGATGACA CCGTCTTTAT CCCGGAGGAT TTTCTTGACC
27061  TTGTTGGCGA TCTCGCCGGC TTCGCCTACG AGACCCATCG TCACGTAGGA GAGACCCTCG
27121  ATGCTGTCGC AGTCGCCTGC ACCGGGGTAG ATCGCTGTGT CGCTCGCGGC GATCTGGTAG
27181  ATGTCGACGT GCATCAGATC ATCACCGGGA ACAACTGGCC ACCGGGCATC TGGATGAACA
27241  CCGGGACGCT GGGGGTGTAG TCCGACGAAC CCGTGCCGCC CTCACAGGCG GACAGGCTCA
27301  GGGTGGCGGC AAGGCCGATG ATGGCTGCTG CGATGGTCTT CTTCATCTGT TGCTCCAGTA
27361  GCTAAGTTCG GACTCCAGTT CGCGGATACG CTCCTGTAGC CCTTGGTTTT CCAGGTACGC
27421  CTCGGCGAGG TTGGCCTCGG CGCGGTCACG GGCCTCGTCC TTCGACGTGG CCTCATCGAT
27481  TGCCTCGTGT AGCCGGCGGA TCAGATCTGG GATGGCACCG TGCAGACCGC ATATGAAGTC
27541  GGCGTCTGCC TCGGAGAGGT GGGACGCCAC CAGATCCTTG TCCTGGGTCT CCTGGTTGAC
27601  CGCCCAGATG ACGTGATCCT CTAGCCCGTG GTCGGTCTCG CAGATAGAAG GCGGTTCTAC
27661  CTCCTCTGGC ATCCAGTAAG TCTTCTCAGC CCCGGTGGAC TTCGCCCACT GCTGGTAGAG
27721  GATGTCGAAG AACTCGTGGT CCTGTTCGTC GGCGGTAATC ACAGATCGTC CTCTTCATCC
27781  CATTCGTCGT AGTAACACGT ACAGCCGCAG CAGGTGCAGC AGCCGCACTC GTAGGTGCCG
27841  TAGTCGTAGT CATCCCAGTC GTCTTCGTCC ATCTAGCTGT ACTCCTTCAT GATTCGGTCG
27901  AACGCACGCG TCTGCACGCG CATCTCCAGG TCGACCGTTC GCTTCAACCA CGCCCATTCG
27961  CCGTCGTGGT TGATCTCCCA CTGGCTCTTG AATGTCGCTG TCTCAACGAG GAACTCGACA
28021  GTCAACGTGT GCAGTCCGTT GTTGCTGGGC TGGAATCCGA TACCGTCCTC AGCGATGTAC
28081  CAGGGCAACT CCTGGCCGTC GAAGTAGACG GCCTTGTCGG TCACCAGTAC TTCAGGGAAG
28141  GTGTGCTCGG TCAACGGCGT CCCAGGTATG GGATGACGCT GGCCCGGAAC TCAAGGAACA
28201  CCATGTTGTC CGGGCAGTCC TCGGGGACGT TGTCGGGCG TTCGGCGGTG TAGACGCCGA
28261  TCTCGTTGCC CTCCAGGGTT CCAAGCTCGT TGAGCTTGTA GATCGCCAGA CCCATCAGCT
28321  CTTCATCGAG ACCGTTCGGT GCTGGCAGTA CAACTTTGGC TTGTGGCATT AGCCCTCCCT
28381  CGGAATTACG TATGCGCTGA ACTCGACGGC CGTAATGCCG TCTGGCAGTT GGAATCCGAA
28441  CCGCTCTTCG AACTCCTCGT TGGTGATGGG GCCGTACTCG AAGGTTCCGG GCACTACCTC
28501  GCCCTCCCCC TCGATCAGGA GGTACGCACC GGCGGCGTAC ACCTCCTCGT CGTTCGGCCA
28561  TCCGACTACG GTCCCGAGGA CCGTGAACTT CCTCGGCTCC ATCAGGGCAC GTCCACTTCG
28621  TTGATGAGGA ACCGCATCGG AGGTGGAGTG AGCATTGCCT CGGCTATGGC GATGAGGGCG
28681  TTCAACTGAC CCTTCAGCAG CTTCTCCTCG TCGCCTGCGG GAAGGTGGCG CACTCGGCGC
28741  TCCATCTCCT TGGCGCGTTC CAGATATTCG GTGGCTGTCA AGTTGTCCTC CTTAGTAATC
28801  AGCGCCGTAG AGCGAACCCC ACGAACGCTT TCCGACCTCG GGTCGGTGC CAACCAGCAC
28861  CGGACCCATC TGTTCTTGCA TCAGGTGGCC AATGTGTGCA GCGGCTCTCT CAGCCTCTGA
28921  GGCGGGCAGA GACGCGACGA TCTCGTCGTG GATAGGCAAC CGTAGGTACG GGGTGTATCC
28981  GGCCTCGTGG AGGCGAATCA GAGCCCGACA GGTCACGTCC CGCGACGACG ACTGGATCAT
29041  GTAGTTCAGC GCGGAGTATG TCCGCGAGCT GTCCACCGGC AGCCGCCGGC CCATCGCGTT
29101  GACGATGTAG CCGTTGCGGC CAGCTTCCAT CGCCAGCTTC TTGCTCAGCC GCTCCACACC
29161  GGGGTATGTC GCAGAGAACG CCTCATGAAC TCGCTTGGCC ACAGGGATCG AGATCCCCAC
```

SEQ ID NO: 1-continued

```
29221 TGCCTCAGCG AGAGCCTTCG CCCCACCGCC GTAGACCTTC TGAAAGTTGG CGGTCTTCCC
29281 AACCTTTCGC GGCACCTGGG CTGCGTCAGC GGTCATCTGG TGGAGGTCCG CACCGTTCTC
29341 GAATGCCTCG ATCATGTTGC GGTCGCCCGA CAGCGCCGCC AGGACGCGAA GCTCCTGCGC
29401 CTGGTAGTCG ACTGAGGCCA TCACATCGCC TGGCTCAGCG ATGAAGCATC GCCGCACGAT
29461 CCAGTCCGAC GACGGCAGCG TCTGCGCCGG GATGCCGGTG ATCGACATGC GCGAGGTCCG
29521 CGCCTGCAGT GGGTTGATGA ACGTGTGGCA GCGGTCCTCA GAGTCCCTGG TGTCGATGAA
29581 CTTCTGGACC CAGGTCTTCC GCCACTTCCC CAGCTTCTTA GCCTCCTGAG CGATGGCGGC
29641 AAGCTCGTTG CCATCTTCGA CCAGCTTGTC GAGCAGAGCC GCGTTGACCT GGCGCTTGCC
29701 AGTCTCGGTG CGACCGGTGA TCTTGACGCC CATCTCCTCA AGCCCCTCGG CCAGATCCTC
29761 GGTCGAGTTG ACCTTCTCCA CGCCGTACTC GGTGAAAGCG ATTGCCTCCC AGACCTCCTG
29821 ATCGGCCAAC CACTTCTCGG CGAGCGACCG CGAGTACTCC ACATCGAGCA GGAAGCCCTG
29881 CCTGTCGATG TAGCTGCAGA TCTCACTGAT CTTGTGCTCG TACGGCACCA GCGACCGACT
29941 CACGTCGGGC ACCAACGGTG TCAGGCTCTT GCAGACCCTC GCGGTGAAGA TCGTGTCCAT
30001 CCCGGCGTAC AGCAGGTACT CCGGGTGGAA CAGGTCGATG GTCGACCAGA TCTTGGCCTT
30061 GGTCGTCTTG TGCTCGGCGG CTAGCTTGGC CATGAGCTTC TTGACGTTCT CGGCCTGGTC
30121 CTCGGAGATG AACTTCGCGA TCAGCTCTTC GAGCGAGTGC CCGAACCCGC CGGCCTCGAA
30181 GGGCCGGGGG TCCACCAGCT TCGCCAGGAT CTGCGTGTCA AGCACGCGGG GCCACAGACC
30241 CTCCATCTCG ATCCCGAAGC ACTGGTCGAG CACCTGGAGG TCGAAGGAGG CGTTCTGGAG
30301 CACCATGCGC TTGAGAGCGC CGATGGCGAT CCGCACGTCC TCGATGAACA CGTCTCCCAG
30361 CTCCACCGGC ACCACCCAGG CTTCGTCCTG AGTACCGAAC TGGACGAGGC GGCACTCGAA
30421 GGTGTCGCTG TAGATGTCCA GCCCGGTGGT CTCAGTGTCG ACGGCGAGGC AGTTCAGGTG
30481 AGCCCGGATG AAGTTGCGGA AGCCTTCCAG ATCCTCTGGG GTTTCAACGA CGTTGACGGT
30541 GACGAGGTCT CCCTGAACCT CATGCCGCAG CTCGATCAAA ATGCTCTCCT ACTGGAAGTA
30601 CTGAGGCGGA ATCCAGGTGG CTGAGGCCAT CTCCTTGATG GCCTGCTGCA TGGCCGCTTC
30661 GAACGGACAG TCCGGGTCGA TGTCCGGCTT GTAATGGGTG ACGATGATCC GGCTGTTGCC
30721 GCCGAAGTCG TGGCTGACCA AGCCCTTTGG GGGCAGCTTC TTCAGCGCCT TGATCAGTTC
30781 CTCAACCGTG GTCCCGGTAG GGGCCTTGCC GTCAGGCAAT GCCTCCCCTC CGTACGGCAC
30841 GTCCAATGGG ATCGTGTACC GCTCAACGTC TTTGATCTTC ATCGAGCCTC TTCCTCTTCG
30901 ACTACCTCGT CTACCCGGCG GAATAACTCC GCTAGTTCTG CGGGTAGCAA TACTGGGTAC
30961 TTCTCTCGGG CTTCCTGCAT CGCTACCGCG ATCCCAATCA GGGCAGCGAG CAGTTCATTG
31021 ACGGAGTACG CCAACAGCTC TTCGCGGATC TCTTCTCGGG TCATTAGTGG TAGATCCCCC
31081 GGACGGTGCG CGAGATCGTG GCAGGGTTCA CGCCGTAGTT CTCGGCGAGA TCCTTCTGCT
31141 TCATACCGCC CAGGTACGCC TGGCGGATGT CCTTGACCTC GCGCTCGGTG AGCTTCTTGC
31201 GGTTCGGCCG GCTCGGGCCG GTCTCAGGCT TGACCTGAGC CAGCGCCTTG CCGAACAGCT
31261 CGTTCTGCGT CCGCTGCTTG ATCGCGTACC GACGGTTCGC TGCAAGCACC TCGTTGAGCC
31321 GCTGGGACAA CTTGACATTG GCCTCACGCA CTACCTCGAC CTCTCCGAGC AAGTTCGTGA
31381 TCCGGTAGTC CTTGTCCTGG TTCTCGATGG CCAACCGGTT GTTCTCCTCG GAAAGCATCG
31441 AGACCTTGTA TTGCGCCTCT CCCAGCGCAG CTTTCAGGTG CTTCTTCCTC ATTCAGCGCC
31501 CCTCTCTCGG CGGAACTGTT CGTACTCGTC TTCGGTCATG TAGTAGTAGT AGTCAACGAC
31561 CTTGTCCCAG TTGAAGGTTC GGGACGTGCC GTCATCGAAC GCGATGATCA GGACACCCTC
```

SEQ ID NO: 1-continued

```
31621  TTGGGTGTCT AGGATCGGCT CGCCAGCCAC GACGTGGAAG CGGTCCTCGA GGGTCACCGC
31681  AGTCGCTCTG CGTGCCATGT CAGTTCCTCT CAGTAGCTGT AGGGGACATC CGGGATGTCC
31741  TGGTAGGTGT TGGGTGCGAT CTGTCGGAGC TGCCGAAGCA ATTCCCCTGC CAGCTCACGG
31801  ATCTCGGCAT CCGCGGCCTC GTGCCAGCGG GCCTTGATGA CGTACCGCCA CGCCCGATGG
31861  TTGCCCGTGA CGACCATCGG TGAGTTCGTC ATGTTCGGCA GGACAGCTCG CGCTGCCTCG
31921  CGGGCCTGCT TGCGCGGCAA GCCCCGGTCA GCCAGCCGGT TGACGATGTG TTCGTAGACA
31981  GCGTCAATCT CAGAGCTGAC GGACTCCATG ATGTGGACGA GGTCGTCTCG GTCGTCGGGG
32041  TGGAGCTTGA ACAGAGCCGG GGGCAGATGG ATGCCAAGGT CGGTCGGATC CACATATCGC
32101  TGAGACACCA CCGAGAAGCT CAAGTGACGG TGACGCTCCA GCTCGGTCAG CACCGACCTG
32161  CTGGCCTCGA TGTAGAACGT CGCCGAGGCG TGCTCGAACA CGCTCTCGTG GCCCAGATCG
32221  ATGATGTGGT TGAGGTAGTC CTCGTTCTCG GCAGTTGCCG GGTTCGGTCG GTGGAACGAC
32281  CGGTAGCAGT TCCGGCCCGC GAACTCGGCC AGCTCGTCGG CATCGAAGTC GCCGAAGTAG
32341  GGATCTTCGT CCTTGGATTC TTCGAAGTCA TCGACCTCGA ATCCGATGTC CCGCAACGCA
32401  CCCGGATCGA TCTCGGTGGC AGCGATCAGT TTGGCTTTCA TACTCTCCGC TCAGAGTTGG
32461  TGGAACGAGG TCAGCCAGGG GGCAGCGAAG CCCTTCTACA GCTCCCCTTG GCTCGTTACC
32521  GGCTTCTCGA CCTCGGTGGA TGTCAAGTAG TCGAGATGAC TACTTCTTGT CGGGCCATTG
32581  CGCGTCACAC TGCTGATCGC GAGGTGCGGT GCAGGAGAAC AGCGCGTACG GCTTGCCCGT
32641  CTTCTTCGAG ACGCCCGACT TGTAGACCAT CTCGCCGTGC TGGCAGTACC GCTTCTCGCC
32701  ACCAGGCGCT TCCTGAGCTG CCTGCGGGGC GCGAGACTGC TGCTGGCCAC CGCCGCCGCC
32761  GTTGGCCGGC GCGGATCCAC CGGAGCCTGC GTAGTGGCCT GCGATCTGCT GGACCTTGTC
32821  CATCAGCGCC TTGAACTCGG CGGTGTTGAC CTTGGCCAGC ACGTCGGCCG GGTCCGCACC
32881  CTTCACGACC ACCCACGGGT CGCTGTACTG ACCGGCGAAC TTGAACGTGG CCGACACCCC
32941  ATCGGTGGAG TGCTGGACCG CCATCGAGTC GCGCACAGCA GCCGAGGCCG TCGTCACCGT
33001  CGCCGACGGC GCGGTCTCAG GCTCAGGAGC CGGGGCCGGC TCGGGCTGGG CAGGGGCGGT
33061  GCTCCACGGA TCGTCGTAGG ACAACTGGTT ACCTTTCACT TAATGGGCA TGCGCCGTTG
33121  GCGCACTCTT CATCGACACC GTCTTCGACG GCTTTGGCCG CAGCAGATTC GTACTGCTGC
33181  TTGGTGATTC GCTCGTACGG AGCCTGCGGG AAGCTGGACT CCGGGAAGAT CGTGGAGCCC
33241  TTGATGAGCC CCGCGAACCT CTTGAGATCG GCTGCGACAT CCTCGGCCTC GTAGGCGTCT
33301  GGATGGACGT TGGCGGTGAA CGACACCGCG TTGTCAGCCC AGCACATCTG GTAGAGCGCC
33361  TGGAACGCCA GGAGCTGGTG GAGGGTCAAC TCGTCGGCTG ACTCAACGAT CTCCTCGTCC
33421  CAACCGAGTT CCTCGACAGC CTGGACCAAC GTGTCCTTGG TCGGGATCGA AACCACCTCG
33481  GTGTTCGGAG CGAAGAGATC CTTCTCGATC TCGTAACCCT CGGCTGCCAA CCTCCGCAGC
33541  TCGGCCATGT CGCTGTTGAG GTTGAACCGC ACACGCCGGA TGAAGTACCG CGAGAAGATC
33601  GGGTGGATCC CCTCGGAGAC TCCTGGCATC TTCGCCACCG TGCCTGTGGG AGCGATGGTT
33661  CGCTTCTTCA CCGGGACAGG GATCCTCAGA TCATGGGCGA ACCGTTCGGC CTCTGAGTCG
33721  ACCTCAGCGG CCATCTCCCG CAAGAACTGG GTGAACCGCT TATCTCCGGG TGCCTCGGAG
33781  TACCTGCTAC CTGTGAGGGC CAAATAGGAG GCAACTCCGA GATGACCCAC GCCGATGCGA
33841  CGGTTTCGGT CCAGAACCTC CCGGCTCTTC GGGTCGGCCA CTTCCGAGAA CGTCGCCCGG
33901  ATCAGGAATC TCGTCATCAG ACGATGCGCC CGGATCAGGT CGAGGTAGTC GGTCTTGCCG
```

SEQ ID NO: 1-continued

```
33961 GCCGGCGTCA CGAACGCCGC CAGGTTGATG TGGCCGAGGT TGCACGGCTC CCACGGTTCG
34021 AGAGTGATCT CGCCGCATGG GTTGGTGCAG ACCACCCGGT TGGGCTCACC GACGTTGGAC
34081 AGTGACGAGT CCCACATCCC CGGCTCTCCG TTGCGTACGG CTCCCTCGGA GAGTGCCTTG
34141 AGCACTCGGT GGGCTCGCTT CTGCTTGGGC ATGTCCTCGC GGGCGACCGC GAAGCTGCCG
34201 TAGCCCTCCT TGGCCAGACG CCAGAACTCG TCGTCAACCT CGACCGAGAT GTTCGTCGTC
34261 CAGTGCTCGC CCGTGCTCGC CTTGATGTTG ATGAACTTGT CGATCTGGTA GTCGTCCCAG
34321 TGCATCATCG ACATCCGCGC CGACCGGCGC ACACCGCCGG CCACAACACA CTGAGCGATG
34381 GCGTGGTCGA CCTCCATCGC GGCGATGCCG TCGAGCGTGA TCCCTGCGTA CTCCGAGAAG
34441 ATGTTGGCGA CCTTCTGCAG CATCACAGCG AACGGCAGCG GGCCGCTGGC CACTCCACCG
34501 AACGTCTTGA GCTTGGCCCC TTGCGGCCGG ATGCGGCTCA CGTCGTACAC CCGCTGGTAG
34561 TGGACCGTGC CGGGTCGGTA GTGCGTGTCG ATCAGATCGA CCAGCGCAGC AGCCCAGCCC
34621 TCTCGTGAGT CCTCGATGGC GTAGGCACCG GCCCAGTCGT GGCTGTAGTG CTCCGACAGA
34681 ATGCCTACAT CCTTCATCGC CTGGTAGTCG ACATGCTCTG GATCACAGAC GATCTCGACC
34741 CGCAGGGGGT TTACGACCTC GGGGTAGCCT TCGAGGTAGT GGTTCGAGTA GTTCGCCCCG
34801 ACTCCCCCGC CCTCCATCAG GCGCATGAAC GTGAACTGGA AGTGGTCCGA GATCTTCTCG
34861 GGCCAGCCAG CTACCCAGCA GTTGAAGAGG TGCTGCGCGT TCTTGACCCC CGAGGCCCAC
34921 AGATGCCGAC CTGCCGGCAG CACCTTGAAC TTGGTCATCA GACGAACGAG ATCTTCTCGC
34981 TCTCCTTCCA ACATATGTCG CCGGTCGACA AGAGCAAGAT TGCCGTCCAC GACCCTCTCG
35041 ACCGTTTCCG GCCAGGTTTC CTTCGAGCCG TCAGGCTTGG TCCTGGCGTA GGTTCGGTTG
35101 TAAACGAGTT CACCGGTTGG TCCCCAAGGG ATTTCGTCAG TCAACTACTT CCTCTCAGTC
35161 AGTTCGTATC GCTTGAAATA GGCGTCGGCA GAGTCGCCGC CAGAGAACGA GACCCCGTAC
35221 TCGACCGGGC CTGCACCACG CACCTCGCAG GTAACGACGC CCTTCCTTCC CCGGAACATC
35281 GGCCAGGTTC CCTTGGAGGG GTGCTTGGTC TCGTCCCGCT GGACGATGAC CTTGGTGCCC
35341 TTCTTCATGC CGACTTCCGT TCTCCGTAGC CGGGAGTGAA GCAACCCCCG ACGTACAGCT
35401 CGAGATCTTC TTGCGACCAG TTCTCCAGTC GCATCGGCGG CTGGTGCGGG AACAGCTCCG
35461 GGAACACCTC GGCCCGGTAC AGCTCCGAAC CGGGCATCCC GTTGAACGTC GGATCAAGAA
35521 TGTTGTGCAT GGCACCTCCC TCCCAAGAAC TCGGAGATCG GCGGCTCGTA GAGGTAGCCA
35581 TCGCGCAGCT CGGGGTTCTC GATGAGCATG ATCGCGATGT TCGCTGTGGG GTCAGAGTGC
35641 CCATCCCCCT GCGACTTTCG GATGTCTGGG AAGATAGCGT GCTTGCTGCC CGGACCATCC
35701 TTGACGATGA CCTTGCCCTT GTCGTCCTTC TCCACGCCAG CCGTGATCGC GATGATGTTG
35761 ACGTGCTCGG TCAGCGACTT GTGAGCGCGG AACAACCGGT TCTGCCCGCT CTTATCCTTC
35821 GGGGAGATCC CGTCGGTGTA GCGGCTCCTG ATCGCCTCTG CATAGCCCCC GTTCTGAGCG
35881 TCCAGAGCCT TCATCGCCAG CGGGAGGATG TCGACCAGGT ACCGATTGGT CGACTCCCCC
35941 TGCAGAGCCT CTTTGACGTT CTCGGACGAG TAGTGGCTGC GCTCCTGGAA CAAGTCGCGG
36001 GCCTTGGCCG CTCCCGACAG GATGTTGCGA ACCTGATTGC GTACGTAGTG AACTGCCTCA
36061 CCACGGTGCA AGCTCTCCAG CGTCTTCTGG ATGTACGGGC TCTCGAGGTA CCAGACCCAC
36121 AGCTCTTGGA TGATCTCCTC GGCTGTCAGG TTGGTCTCCC AACCGATCAG CGCCTTCCGG
36181 GTGGCCCTGC TGAACAGCTT GCTGATGTCG TCGGTCAAGG CATCACCTTT CGTAGGTACT
36241 CCTCCCGGTC CAATCGGCGG TCGAGGTGTC GAGTGACCTC CTCCGCGAAG ACCTCGCGGA
36301 CTTCGCTGGA GGTGATCTGG CGCGAACGTG CGTTCTTGTG CAGGTACGGC AGCTTGGTGG
```

SEQ ID NO: 1-continued

```
36361 CTGTCAAGTT CTAGACCTCC CAGACTCGGC CGTCGACCGA GAACCGGCCT CCGACAATCG
36421 GAACAAGCTC AGGCTTGACG TGCTGGCCGT CGACCGTCAG CAGAGCAAAA CCACTCTGCC
36481 AGTTGGCTGT TGCACCCTTG AGGTACTGAG CTAGCTTCAT GTTCATCAGG TTGCCGACCT
36541 CCATCGACCA CAGCACCTTC TGGTTGCCGC CGTAGCCCAG CGTGTGTGGC TTGATGCCCT
36601 GGCGGTGGGT GTGTCCGATG ATCACCGACG TGCCGAACCG CATCATCGCG TTGTACGCGG
36661 TGTCAGCGGA CTTCTGCGTC ACCCGGACCC CACCACGGTG GCCGTGGGTG GAGATCCAGC
36721 CTGGAGCGAT CTTGTAGAAC TCAGGCAGCA CGTCAACACC GAACCCGTCG AAGTCCAGCA
36781 GGTTCTGGAA CTGGAACGAG CTGACGTACT CGACCAGCGC CGGGGCGAAC TGGTGCAGGT
36841 AGTCGACTGG CCGGCGGTCG TGGTTGCCCT CGTGGACACC AACCGGGCCG TCGTAGACCT
36901 GGCGCAGCGG CTCCAGGAAC CGCCGCTTGC ACTGCTCGGA GTCGGGCTTG ATCCGCTGAG
36961 CGAACTCTTC CTTGGTGCCC TTGGTCCACC GAGACGGGCT CGGGTAGTCC ATCAGGTCAC
37021 CGATGTGGAC GACCTCGTCA GGCTGGGTGT CCCCGATGTA GCCGATGACC GCCTTCAACT
37081 GCTTGCGATC ATCGAACGGA ATCGGGTGT CCGAGATGAC GACGATGCGC TTGCTCACTC
37141 AGCGACCTCG GTGAAGGGGC CCCGCATACG TTCCTCGTGG GAGCTGGCGT TGCCTCCTGA
37201 CCAGCGTCGC TTGCCCACCT TGGTGTGGTG CAACCCGTTG GGGTAGTAGA TCCACTTCAC
37261 TCCTGTGGCG TTGGTGACGG TCTTCACATC GGCAGGAACG TCCAGCAAGG TGTCCCACTG
37321 GCGAGGCCCC TTGGGATACC GCTCGTCCTC GGGGAGCTGC ATCTTCTCCA GAACGCCTGC
37381 GTAACCGGCG ATGTCGACCA CCGTGTCCTG GTGGTAGCCG TTCTCCATGA ACCGGGCGAT
37441 CTTCAGCAGG ATCATCATGA CGGCCACGTC CTCCGGGGTG AACTCGACGC CGCGCTTGTA
37501 CGCGCCCCAC AGGGTCGCGA TGCGTTCGTG GTTCTCCTTG GCGTCCCCGT AGTCCTGGGC
37561 TCGCTGTCCG TTGATGATCT CTTCGGCGGT GGTCAGAATG CTCACAGTCC AGTCTCCGAT
37621 GCGGTGTAGT AGTCGATCAG CTCATCGAGC TGGTCCGGTT GATAGCCGAG GATCGGCTTG
37681 TGGGTGTCAG TGACGACGAC GGGAACCGAC ATCGCGTTGA GCACCTTGGT GACGTAGTCG
37741 TACGCCTCCG AGTTGGCCGT GACATCGACT GCGTCGAAGT CGATCCCGGC AGCCGTCAGC
37801 TTGTCTTTGA CTCGCTCGCA TGGCTTGCAG CCGGGACGGG TGTACACCGT GACCGGCGCG
37861 AACAGCGTTC TCACGTGAGC ACCATCCCAG TCGATGTATC GGTCTCCATA CATCAGATCC
37921 TTTCCAGCAG AGCAGCTTTG CCCTGCGATG TGACTAGTGA GTTGACATCC TCGCCTTCTG
37981 GCATCGGGAT GATTCGGGCG TTCGGCAGCG TCTTCGCCAC CGACCGGGCG AACTCCATAC
38041 CGGCGTCGTC GCCGTCGGCC AGGATGTTCA CGTTGCGGTA GCCCAGGAAC AGCTCTCGGA
38101 AGTACGGCTT CCACTTCTGG GCTCCGCTGA GCCCCACCGT CGGCAGCCCA CACAGCTCGG
38161 CGGTGATCGT GTCGAGTTCT CCCTCGCAGA TCGCCATGTC CTTGCTGTAT TTGGTCAGCG
38221 CGTAGGTGTT GTAGAGCCGG TCCTTCTCCC CTGGCATCGA CAGGTACTTC GGTGTGCCAC
38281 CGTCGATTCG GCGATACCGG ATCGCAGCTA CCGTCCAGTG ACGCCAGGGC GACCACCGCA
38341 TATACGGAAT CGCCAGGCAG CCCCGGTACA TCTCATGTCC AGGGAGTGGG TCGTCCACGA
38401 ATCCCAGACC GAACCGGCTT AGTTCCGCTC GGCCGGCCAG CCCGCGACTC GCCAAATACT
38461 CGTCGGCTGG GCTTCCGGGC AGGCTTTCTC TGTACCGGGA CGTTGCCTCC CACAGATAGG
38521 TTCTCTGCGA TTCGCTTAGC CTCTGCAAAT GTCACCTCCT CTTCGTGACG AATGATCGAG
38581 ATCACGTCTC CACGGACCCC GCAGGCCATG CAGTTGTAGC CCTGTAGGTC GTAACTGACT
38641 GCGGCAGACG GCGTTTCGTC GCCGTGGAAG GGGCACAGGC ACTTGTTCCA CTCGTGGTGG
```

SEQ ID NO: 1-continued

```
38701  TCAGGTGGTG GTTCCCAATC CGGGTGGTAG CGAAGAATCG CCCTCGCGAT GGGCGAGTCG
38761  TTCATTCGTC CTCGTCAAGC TCCTCGGGAG AGAGCCCTTC GAAGATCCCG TTCAGGACGG
38821  CGGCGAAGCC CTCGCCGGTC TCCGCTGCGT CGAGCATCTC TGCAATCGTC TTTGCCATGT
38881  TTCCTCCTGG TGGATGTCAA GTTCGAGACA GCTTGTCAGC CTCGACTGGA GCGATGCGCT
38941  CCCCGATGAC TTGGACGGCC GGCGGGTTCA GCAGGTACTC GATGGCCCGT TTGAAGAACT
39001  CGATGCAGTC CCTCGCCCAG CCCAGCGTGT ACTTGTTGCA CATCGTGCAG AGCAACCCTC
39061  GGACGATGCC TGTCTTGTGA TCGTGGTCGA CCGACAGGCG CTTCTTCTTA CCGTTGGCTC
39121  GCTGGCAGAT GTAGCACCGA CCACCTTGGA ACTCGTAGAT CTGCCAATAC TCATCGCCGG
39181  TGATGCCGTA GGTGGCCAGG ATCCGGGTCT CCCAGCTCGT AGAGCTGCGA GCCGTCCTGA
39241  ACTCTCGGTG ATGAGTAGCG CATCGTGGCC CTGGATACTT GGCGTCTCGC GTGAGCGGGA
39301  GCCCCTGTGC GACACAGTCT TTGCAAGGCT TCCGCTTGTG CTTACGGTTC TGCACCCGGT
39361  ACCCCGGAGA CCTCTTCGCC GCCCTCGGCA CGCGCGTCCT CCTCCCGGTT CTCCATCACC
39421  ATGCAGAACC ACGACAGCAG CCCTGCCAGG GAGATGTAGA AGGCCACCAG AACTTGGCCG
39481  CTCACTTCAC CATTCCTCGA ACCCACCAGC GAGACAGCGC CTTACGCCCT TTGTCGAGCG
39541  GGGTCAGCTC GCGCTCATCG TCCTCACCGA AGTCGAACTC GATGCTGGCG ATCTCGTAGC
39601  CGAGGATCTT GAACGACACG TTCATAGGCG GTCTCCGAAG TTGATGACGG GAATGCCGGC
39661  CCTTTCGGCC TCTCGCATGC AGTGCCGGGT GCCGACTGAG TTGCCGAGGG GGAACGCCAG
39721  ACAGATGTCC GCACCGGCCC TGACCATCTC GATGTTGCGG AGGATGCCAG CCCGCTTGCC
39781  GTAGCGTTCC CAGTCGGCTC GGTGCAGCTC GGGGAGCACG TCCCATCCCT CCTGCTTCAT
39841  CCCCCAGGCC CAGCGGTCTG CGATGTCGTC AGCGCCGCGA GCGCCGCCGT GGACGACCGT
39901  GAGACCGGAG AAGGACCGGT GGTACTCAGT GGCCAACGCT TCCCAGACCG TGGTGCGGTC
39961  CTTCCAGATC CGAGATCCGG TGATCAGTAC TCGCCGCATC AGATCGCCTC CCACTGCAGG
40021  CCGTCGTGCG ACGTGACCAG CTCCGCTTCG TAGACGCCGT AGCGGGTGGC CAGGAACTGG
40081  ATCATCTGCG CCTGCTTGTA CCCGAAGGGA CATTCGTGGA CGCCGCTGAT CGGGTATCTG
40141  ACTCCGTATT TCACTTGATC CACCGCTTCG CGATTCGGTC GACGTTCTCC TCGGAGACGT
40201  TGCGGGCGAG GCCGGTGAAC TCCTGGCCGT GGACCTTGGT CTCGATCACG CGAGGCTTGC
40261  GGGGATCCGG GCTCTCCGGG TCGATCCGCT TGTGGGTCCA GACGGTCGGC TTCGTCTTGA
40321  TCAGAGCGCC CAGCACCTGC TGGCGCAGTG GGTTGGTCTT GCGGGGCATA GCGTTTGGAG
40381  TGGTCATCTG GATCCTTTCC TCGGTGGCTG TCAAGTCGGT GTGCGTAGTG AAGCCCCCCC
40441  AGGCATGCGC GCCCCGCCTG GGGAGAGTTG ATCAGCGCAG TTCGATGTCG GCAGGATCG
40501  CCTGCGGCTT GAAGTTGACC TGGTAGAAGT CGGTCGAGAC GTTTGCGCCA TCGACCTGCT
40561  CCATGAAGTA GGAGACGTTG TCCGACAGGC CCAGGAAGTG CTTCTTGATC CCGTCCTTGG
40621  TCTTGCAGGT CACGTCGAGC TTCTTCGACG CGGTGTCCGC GTTGATTGAG CACCGGCCCT
40681  GGATCTCGAG CAGGTACTTG TCCGTGATCC CGTTGAAGAA CACGATCCGG CGATTGATCT
40741  CGAAGTTGTC AGCGGCCTTG CTGACGTTCT CCGATGCGAC GTCGGCGTCG GAGGTACACG
40801  CGGAGAGGCC CAGGATCGCC GATCCGGCGA TGAGTGCGGT GGCGATGATC TTCTTCATGT
40861  TCGCTACTTT CTGTTTGGTG GATGTCAAGT TAGTGACCGA AGTCGTTGAT CTGCATAGTG
40921  TCTCCGACGA ACTCCAAGGA AGCGAAGTCT TGTCCCGACG GGTCCGACTT CCCCCCTCGG
40981  TTCTTGACCG TGGAGACGTT GAGCATGTCC GGGCCGAACC CGTCCGATAC TCGGTGGAGA
41041  GTGAGGATCA TCTCAGGAAC ACGCCCGATC TGACCTTTGA TGCCCGACAA CGGGATCGGC
```

SEQ ID NO: 1-continued

```
41101  TTGTCGCCGT CGTTGTGCGG GCCGGTGACG TGGTGGAGCC CGACGACGCA TGAGCCTGTC
41161  TCACGGCCCA TCTCGTGTAG GTAGTCCATC AGCGACTCCA GACCCGAGAA CGGGTCGTCT
41221  CCCTCGCTTG AATCGGTGCG GACGTTGGTG ATGTTGTCCA CGACGATCAA CGCTGGGAAG
41281  TCCTCGTACA GCGCGTCATA CGCGGCCAGA GCGTTCTCGA TCTCGTCCAA CGACGGTGAT
41341  GCCTTGTAGT TGAACCGGAT CGGGATCTCG TCTAGTGAGT CAGCTACCGC GTCCTCGATG
41401  TTCTGCTCGC GAACAGCCCG CGTAGCTCGT TCGAGCGACC ATCCGCTGAG GATGGACACC
41461  GAACGGGAGA GCTGGGTGAA CGCATCAGAG TCGGCCGAGA AGTACAACGT CGGCACCTTC
41521  GACTTGAGCG CGTAGGCGAG GACGAACGCC GACTTCCCGG TGCCGGGGCC GGCGCAGACC
41581  AGGACTAGCT GGCCTCGTCG GAGATGTGTA CCTTTCTGGT CAAGCGCGGC CCAGACCGGG
41641  GGTAGCGGAT CCCCCGCCGA CCCTCGGATG TAGAGCGATT GTCTAGGTGT GTACACCTTC
41701  CTCCTCGTGG ATGTGATTGA CCAGGTCATA GATCTCGTCG CGAGAGACCA GCCGGCCCCA
41761  GGCGTCGATC CCCACGTGGA TCTGTCTCCG GTGGATGTGT CGGGACAGGA TCATCGGCGA
41821  ATGCGTGTGC CCGTGGATCA GGATCTTGCC ATCGTCACGG AGCCTCCACT GGGTGTGTCG
41881  GTCCTCGCTG GTGTGGTCCC CGACGTATGG GAAGTGGCTC AGCAGAACAT CTGTGTGCCC
41941  GCCAGCGTCC CCGTACAGCG GCACCCGGAT ACGAGCTGCC GTCGACACAT GCTCGAACAC
42001  CATCCAGTAC GCACCAACCA GCTTGTGAGC ATCGCGGTTC ATCGGGTGGG GCCCATCGTG
42061  GTTGCCCAGG ATCAGCCGTT TGCGGCCTGG CCGATCCGAG ATCCACCCGA GGGCATGTAT
42121  CTGCCCCTTG GTGGAGCCAG AGGAGATGTC ACCTAGGATC CAGACCGTGT CGTCCTTGCC
42181  GACGACCGAG TCCCACGCCT TCGCCAGGGT GGCGTCGTGC TCTTCGACAT CATCCGCCAG
42241  GTTGCGGATC TCCATCAGCC GCTTGTGTCC GATGTGTAGA TCGGACGTGA ACCAGGTGTT
42301  GCTCATGGCT TCCTTTCAGA ACGGCGGGCC GTACAGCTCG ATCACCAGCC GTGCAGCTC
42361  CTCTGCCGCG TCGTCACGCT CGAATCCGCA GCAGGAATCG TGCCGGTCGA GGATTGCGAC
42421  GATCTGGTCG TAGAGGCTGG GCCTCACTTC ACCTTCTTCG GATCGATCAA GGCGTCGTGA
42481  ATCGGCCGAC CGGCGCGAGC CGCGTGCGTC TCGGCGTCCA AGGCTCGCTG CATCTGGTTC
42541  ATCAGCCGGG TGCCGCGCAG CTTGAGGATC TTCATGGTCG CCCGACCCTT GTATCCAGCG
42601  CGGTGCATCC GTAGGACGCA GGCTGTCTCG TGCGGGCTA TAGGTGACCT CAGCGACGGG
42661  TGGTTTGGAT CCCAGTTCGT CATGTCTTCC TCTCGGTGGC TGTCAAGTTG GTCACAGACC
42721  GAACTCTTCC TGGTACTGCG GGATGAAGTG GCCGGCCGTT CATGTTCGGC TCGATACCTC
42781  TCGCGTCACG AACTCCTGCC CGTTCCATCT CCGACCGTCC TCGAACTCGA TCACGATCTC
42841  TCGTCCGGGA TGACGCACGG CCTCCGCTTG GGCAAACCTG CGTGCAGCCT CTGGGGTCGG
42901  GAACGGAAAC TTCTGCGAGG CGTACAGCTC CTGGTGCCAC TTCGGCTTGT CAGGAATCGG
42961  CCCCATTTCC ACGTACGTGT AACCCGCGTC GGGGTCGAGT TCGAGCGTTT TCTTGTATTC
43021  CTTCGTGCCT GCCTTAGAGG GAAGGTGAGT ATCGGTGGCT GTCAAGGTGA CCTCACTTAA
43081  AAACAGGGCA GCTGTAATTC ACATCACAGA AGCCGCATTT GTCAGGTTCA GGCAGAGGCT
43141  CGAAGTCACC AGCCTGGATC CGAGCCTCGA CCTCATGGAA CCTCTCGGTG ATCCGCTCCC
43201  GCGTCCAATC GGTCAGGTCG TAGGGCGCAG TGGGCTTCGC CTTGATGCCC TTCTTCCCCG
43261  CCATGAAGTA GTCGCCCGTC TTCGGAGCCT CCACGTCATA GGTCATCGCG ACCGCGAGCG
43321  CGTACACGCC GAGCTGGAAG TCGTCACCCG GCGAGTTGCC GGTCTTGTAG TCCCGGACTC
43381  GAAGCTCACC GTTGACCACG ACGACCGCGT CGATGAACCC TCGGACGCGG ATGCCGTCCA
```

SEQ ID NO: 1-continued

```
43441 GCTCGATGTT GAACGGAAGC TCGATGGCCG GCTTGGGCTG TTCACACTCC TTGCAGTTGG
43501 TGTCTTTCCA CGCCTCCGTA GAGCAGATCC CTCGCCCAGG GGTAGTCCAG ATCTGCTGGC
43561 CCTTGTCCTT CCGCCACGCG ATGAACTTCT CTACCTGCTC CAGTCCAAGG TGGAACCGGC
43621 GCTCGATGTC ACGCTCACCG TTGTACGGCC CGGACCAAAA CCACCACTCG AAGTTCGGGG
43681 TTTCGTCGCA CAGTGCTCCG ATGTCCTTGG CGTACTCCTC GCGGAAGATC TCTTGTGCCC
43741 GTTCGAGGCT CATCTCGCGG CCCTCGGCCA GAGCCTTCTC GTAGACCTCA GCGACGGTGT
43801 GAAACGCGGT GCCCTGCGGC AACCACGCCG CAGGACGAGC CCATACCTTG TCGATGCGAG
43861 CCAGCTTGTA CGCCTGCGGG CAACGTGTGT ATTGGTTCAA CTGGCTGACG CTTCGCAGCG
43921 GCAGCAATGT CTTGGTGTCT GTCACGCAGC GGCCATCCTT CCCTTGCCTA TCGTCTCGTT
43981 CAGCGCCCCG TCGACAGCGA CACTGAGCAG TTTTGCGACC TCCGACATGT CAATCGGATC
44041 CTTGGGGAAT TGGTCAGCCT GAGTCATCCT GAGCACCATC CACTCGGTGC CCTTGTCGCA
44101 GTGGATCATG GTCGGATCCT TAATTAAGAT CCTTTAGTGA GGGTTAATTG CGGCCGCGAA
44161 TTCTTGAAGA CGAAAGGGCC TCGTGATACG CCTATTTTTA TAGGTTAATG TCATGATAAT
44221 AATGGTTTCT TAGACGTCAG GTGGCACTTT TCGGGGAAAT GTGCGCGGAA CCCCTATTTG
44281 TTTATTTTTC TAAATACATT CAAATATGTA TCCGCTCATG AGACAATAAC CCTGATAAAT
44341 GCTTCAATAA TATTGAAAAA GGAAGAGTAT GAGTATTCAA CATTTCCGTG TCGCCCTTAT
44401 TCCCTTTTTT GCGGCATTTT GCCTTCCTGT TTTTGCTCAC CCAGAAACGC TGGTGAAAGT
44461 AAAAGATGCT GAAGATCAGT TGGGTGCACG AGTGGGTTAC ATCGAACTGG ATCTCAACAG
44521 CGGTAAGATC CTTGAGAGTT TTCGCCCCGA AGAACGTTTT CCAATGATGA GCACTTTTAA
44581 AGTTCTGCTA TGTGGCGCGG TATTATCCCG TGTTGACGCC GGGCAAGAGC AACTCGGTCG
44641 CCGCATACAC TATTCTCAGA ATGACTTGGT TGAGTACTCA CCAGTCACAG AAAAGCATCT
44701 TACGGATGGC ATGACAGTAA GAGAATTATG CAGTGCTGCC ATAACCATGA GTGATAACAC
44761 TGCGGCCAAC TTACTTCTGA CAACGATCGG AGGACCGAAG GAGCTAACCG CTTTTTTGCA
44821 CAACATGGGG GATCATGTAA CTCGCCTTGA TCGTTGGGAA CCGGAGCTGA ATGAAGCCAT
44881 ACCAAACGAC GAGCGTGACA CCACGATGCC TGCAGCAATG GCAACAACGT TGCGCAAACT
44941 ATTAACTGGC GAACTACTTA CTCTAGCTTC CCGGCAACAA TTAATAGACT GGATGGAGGC
45001 GGATAAAGTT GCAGGACCAC TTCTGCGCTC GGCCCTTCCG GCTGGCTGGT TTATTGCTGA
45061 TAAATCTGGA GCCGGTGAGC GTGGGTCTCG CGGTATCATT GCAGCACTGG GGCCAGATGG
45121 TAAGCCCTCC CGTATCGTAG TTATCTACAC GACGGGGAGT CAGGCAACTA TGGATGAACG
45181 AAATAGACAG ATCGCTGAGA TAGGTGCCTC ACTGATTAAG CATTGGTAAC TGTCAGACCA
45241 AGTTTACTCA TATATACTTT AGATTGATTT AAAACTTCAT TTTTAATTTA AAAGGATCTA
45301 GGTGAAGATC CTTTTTGATA ATCTCATGAC CAAAATCCCT TAACGTGAGT TTTCGTTCCA
45361 CTGAGCGTCA GACCCCTTAA TAAGATGATC TTCTTGAGAT CGTTTTGGTC TGCGCGTAAT
45421 CTCTTGCTCT GAAAACGAAA AAACCGCCTT GCAGGGCGGT TTTTCGAAGG TTCTCTGAGC
45481 TACCAACTCT TTGAACCGAG GTAACTGGCT TGGAGGAGCG CAGTCACCAA AACTTGTCCT
45541 TTCAGTTTAG CCTTAACCGG CGCATGACTT CAAGACTAAC TCCTCTAAAT CAATTACCAG
45601 TGGCTGCTGC CAGTGGTGCT TTTGCATGTC TTTCCGGGTT GGACTCAAGA CGATAGTTAC
45661 CGGATAAGGC GCAGCGGTCG GACTGAACGG GGGGTTCGTG CATACAGTCC AGCTTGGAGC
45721 GAACTGCCTA CCCGGAACTG AGTGTCAGGC GTGGAATGAG ACAAACGCGG CCATAACAGC
45781 GGAATGACAC CGGTAAACCG AAAGGCAGGA ACAGGAGAGC GCACGAGGGA GCCGCCAGGG
```

SEQ ID NO: 1-continued

```
45841 GGAAACGCCT GGTATCTTTA TAGTCCTGTC GGGTTTCGCC ACCACTGATT TGAGCGTCAG
45901 ATTTCGTGAT GCTTGTCAGG GGGGCGGAGC CTATGGAAAA ACGGCTTTGC CGCGGCCCTC
45961 TCACTTCCCT GTTAAGTATC TTCCTGGCAT CTTCCAGGAA ATCTCCGCCC CGTTCGTAAG
46021 CCATTTCCGC TCGCCGCAGT CGAACGACCG AGCGTAGCGA GTCAGTGAGC GAGGAAGCGG
46081 AATATATCCT GTATCACATA TTCTGCTGAC GCACCGGTGC AGCCTTTTTT CTCCTGCCAC
46141 ATGAAGCACT TCACTGACAC CCTCATCAGT GCCAACATAG TAAGCCAGTA TACACTCCGC
46201 TAGCGCTGAG GTCTGCCTCG TGAAGAAGGT GTTGCTGACT CATACCAGGC CTGAATCGCC
46261 CCATCATCCA GCCAGAAAGT GAGGGAGCCA CGGTTGATGA GAGCTTTGTT GTAGGTGGAC
46321 CAGTTGGTGA TTTTGAACTT TTGCTTTGCC ACGGAACGGT CTGCGTTGTC GGGAAGATGC
46381 GTGATCTGAT CCTTCAACTC AGCAAAAGTT CGATTTATTC AACAAAGCCA CCGAACGCCA
46441 GCAAGACGTA GCCCAGCGCG TCGGCCGCCA TGCCGGCGAT AATGGCCTGC TTCTCGCCGA
46501 AACGTTTGGT GGCGGGACCA GTGACGAAGG CTTGAGCGAG GCGTGGAAG ATTCCGAATA
46561 CCGCAAGCGA CAGGCCGATC ATCGTCGCGC TCCAGCGAAA GGGGTCCTCG CCGAAAATGA
46621 CCCAGAGCGC TGCCGGCACC TGTCCTACGA GTTGCATGAT AAAGAAGACA GTCATAAGTG
46681 CGGCGACGAT AGTCATGCCC CGCGCCCACC GGAAGGAGCT GACTGGGTTG AAGGCTCTCA
46741 AGGGCATCGG TCGAGGAACT TTCGGCGGCT TTGCTGTGCG ACAGGCTCAC GTCTAAAAGG
46801 AAATAAATCA TGGGTCATAA AAATTATCAC GTTGTCGGCG CGGCGACGGA TGTTCTGTAT
46861 GCGCTGTTTT CCGTTGGCCG TTGCTGTCTG GTGATCTGCC TTCTAAATCT GCACAGCCGA
46921 ATTGCGCGAG CGGGGTTTTG CTGAAACCGA CACACAGCAA CTGAATACCA GAAAGAAAAT
46981 CACTTTGCCT TTCTGACATC AGAAGGGCAG AAATTTGCCG TTGAACACCT GGTCAATACG
47041 CGTTTTGGTG AGCAGCAATA TTGCGCTTCG ATGAGCCTTG GCGTTGAGAT TGATACCTCT
47101 GCTGCACAAA AGGCAATCGA CCGAGCTGGA CCAGCGCATT CGTGACACCG TCTCCTTCGA
47161 ACTTATTCGC AATGGAGTGT CATTCATCAA GGACNGCCTG ATCGCAAATG GTGCTATCCA
47221 CGCAGCGGCA ATCGAAAACC CTCAGCCGGT GACCAATATC TACAACATCA GCCTTGGTAT
47281 CCTGCGTGAT GAGCCAGCGC AGAACAAGGT AACCGTCAGT GCCGATAAGT TCAAAGTTAA
47341 ACCTGGTGTT GATACCAACA TTGAAACGTT GATCGAAAAC GCGCTGAAAA ACGCTGCTGA
47401 ATGTGCGGCG CTGGATGTCA CAAAGCAAAT GGCAGCAGAC AAGAAAGCGA TGGATGAACT
47461 GGCTTCCTAT GTCCGCACGG CCATCATGAT GGAATGTTTC CCCGGTGGTG TTATCTGGCA
47521 GCAGTGCCGT CGATAGTATG CAATTGATAA TTATTATCAT TTGCGGGTCC TTTCCGGCGA
47581 TCCGCCTTGT TACGGGCGG CGACCTCGCG GGTTTTCGCT ATTTATGAAA ATTTTCCGGT
47641 TTAAGGCGTT TCCGTTCTTC TTCGTCATAA CTTAATGTTT TTATTTAAAA TACCCTCTGA
47701 AAAGAAAGGA AACGACAGGT GCTGAAAGCG AGCTTTTTGG CCTCTGTCGT TTCCTTTCTC
47761 TGTTTTTGTC CGTGGAATGA ACAATGGAAG TCAACAAAAA GCAGAGCTTA TCGATGATAA
47821 GCGGTCAAAC ATGAGAATTC GCGGCCGCAT AATACGACTC ACTATAGGGA TCTTAATTAA
47881 GGCGCCTGAT CAGGATCAGG TCGATGGCTT TGTTGTTCTC CGGGCAGCGC ACCGCCGTCG
47941 GAAACTCGGC CTTGCCTTTG GCGAACGTGG TGTCGACGTA GGCGATGTTG ATGCCCTTGT
48001 CTTCCAAGAA GCGCGCCACG TCGATGTTGT CCGGGTCTGC GCTGAAGTAC AGCGCCAGGT
48061 TGTCGAGCCT CTGCGAGTGC AGGTAGACAG CCGCCGTCTG AACCCTTGTG TAGGCCCAGA
48121 ACTGGACATC CGGGTTGTCG CGGATGACTC GACCCCAAGC GGCCACATAG GTGGGGCTGA
```

SEQ ID NO: 1-continued

```
48181 AGAAGTCTCC ATCCCAGTGG ATGCGGAACA GCTTCGGAGC CTTGCGACGG TCGCAATCCT
48241 TGACGAACTC GGCGACCATC TCGGACAGCA GCGTCACGGT GTCTGTCAAG TCAGCGTCAC
48241 TGACGAACTC GGCGACCATC TCGGACAGCA GCGTCACGGT GTCTGTCAAG TCAGCGTCAC
48301 GCAACAGTTC CCAGTTGTGC AGCAGGACCG AGCTGACAGC CTTGCGAACT TTCTCCAGCT
48361 TGCCGGCGTA GCACACCTTG GCACAGAAGG CCGTCGCGTC CGGGCAGGAG AAGCCTTGAC
48421 CGGAGGGCAG GCCGATGCTG TTGGCGATAC CTACGGTGGC GTTGCCGCCC TTGGTGACGT
48481 GGACGTAGTT GGTGACCTTG CGGTCGTTCG AACGCTTCAG CTTGGCCATA CCTAGCCTTC
48541 CTTCGGTGGC TGTCAAGTTG TTGGATACAA AGCGCCCCGA GAGGGAGTCG AACCCTCACA
48601 CCGCGAACCG TCGCGGGGCC ACCGTGCCTA GTCGATAGAG GTCACTGAC TCTCGTGGAC
48661 GTAGACCACG GTGTTGCCTA CGTTCACCGC GTAGTACAGG CCATCGGCAC CTCGTAGCTT
48721 GTGCCGAACC GTGCCCGACG TGGCCGTCAT GTCTTCGCCC CAGTCGGCGT TAGGTGCCCA
48781 GGTGACTCGC ATGGTGATCC CTTCAGTAGT CGGTGGCTGT CAAGTCAGCG GATACGGACG
48841 TACCCGTTGC CTCGAGCGAC GTAGATCTTG CCGTCGATGT AAACGCGCTG CTGCTGGTTC
48901 ATAATCCTAT TCCTTTCGGT GGCTGTCAAG TCTCAGGCCC AGCGACGAGT CGTCGGCCGG
48961 GGGCGGCGCA CCTTGGGCGC GTTGGCTCGC GGTGCCTTAC GGATGGCGGT GCCTACCGTG
49021 ATCTCTTCCA ACTGGCGTTC AGCCAGGCCG ACAGGCCGGG CGTCACCGGG CAGTTCGATC
49081 TTGTAATCGA AGTCAGTCCA CCCCTTCAGA CCCTTCTCCA GCTCGCGATC AACAGACGC
49141 GGAGCCGACA GCTCAGGCGC AACAAACGGT GTCTTGACGC TCTCGCGGGC AGTAACCCGA
49201 ACCTCACGGT GCTCAGCGAA GACTGGCATA GTTCACCCCT TTGGTGGATG TCAAGCCTGA
49261 GCACCAAAGC TCAGGCGTAG TGGGTAGTCG GGAATCGAAC CCGATAGCTT CATAGCCACG
49321 TTCTACGGCT CAGCCATAGC TCAGCGATCA TTCCATCGCG CCAAGAGCTA CCCTCCCGAA
49381 TGCCGAACCA AAGCTCAGCA TTCGTAAGTG TGTATTCTCC CCGTGGCTCA GACAGTATCT
49441 ATCAGAACCT AACCACAGGT CTACATTTAG TTATCCGCAG TGCTCGCACT TTAACGGCAT
49501 CGAGCTTCCG CCGACCCTCA GTCCTCTGGC AGCGAACTAA AGGTTTGAGT CGGGCTGCGG
49561 CCCTTCTCGG TCTTGCGTGA TTCTCACTCT ACCGGATGTT TCGGTGGCTG TCAAGCGGGC
49621 CGTTTTGGTG TTGCAACGAT GCCCTCGTTT AGCGCCGCTG GCGTAATGCG CTACCCGCCT
49681 GATCTCACCG GTCCAAGTTG GTGATGCTTG CAGCTTACCC GATAACCGGG TGGCTGTCAA
49741 ACCGGAGAAT CTTGCCGCCG GATTTTCACC GGCACCGGCA CGATCCTCTC GGATCCGCCT
49801 ACCGCCTTGC TGCTGCGGTG ACACAAGAAT GCACTACTGG CCGGGTGGCT GTCAAGCCCT
49861 AATCGCAAAT TGGTGCCCTA GCTGCAGATA TGGCGCGTTC TCGGTGGCTG TAAAGGGCAC
49921 TACGTGCCGC TATCCGCTGG TCACGCTGGA CAGTCCCGGC AGCCCGTGCC GCGCATAGGC
49981 TGCTCACTAC GTGCCCGGTA TCGGCGTTGT CGTGCCGCTG TCGTGGTCGT CGCCCCGTCG
50041 CTGTCGCTGG TCTCGGTGGC ATCGCTTGAC AGTCGCCCCG CTATCCCCCG TTGCCGCTGG
50101 TCAGACGCTA ATCCGCTTAT TTCGCATAGG CTGCTCACTA TCGCATCGGT ATGCGTATGC
50161 GCTGGTCACA TATGCGTGTG GTGGTGGTGT GGTGTGCGTG TGTTTGCGCT GGTCAGCCGT
50221 GTGCGTACCG TATCCGCACA CTGTGCTTGT GCGTTTGCTG TGTGTCGAGG CCGGCTCTCG
50281 CATCGTCGCA TGTCAGCGCG GGTATGGGCG TGTATCGCAC GCTTTGCTAG CCGCGTGCCG
50341 C
```

49

EXAMPLE 3

Construction of L5 Polymerase Complementing M. smeqmatis Strains mc²889 and mc²890

Transposon delivery shuttle phasmids should not be able to replicate in the recipient strain to which the transposon is to be delivered. However, in order to maintain and propagate the shuttle phasmid, a conditional host in which this vector will be able to replicate should be available. In the case of phAE41 pol or phAE42 pol, this host should be one from which a high titer phage lysate can be obtained. Therefore, a trans-complementing derivative of M. smegmatis mc² 155 carrying the L5 polymerase gene integrated in its chromosome was constructed. phAE41 was cleaved with PvuII and SacII and 7620 bp fragment containing the pol gene, was agarose purified and subsequently cleaved with AsuII. Cleavage with the AsuII produced a 2211 bp internal DNA fragment containing the intact pol-gene. As a cloning vector, an integration proficient expression vector pMV361 was used (see Stover et al., Nature, Vol. 351, pp. 456–460 (1991)). The cloning vector was digested with ClaI, dephosphorylated and subsequently transformed in E. coli DH5α from Bethesda Research Laboratories. Kanamycin resistant colonies were screened for the presence and orientation of pol gene downstream from the hsp 60 promoter. An E. coli clone was selected. Plasmid DNA was isolated and electroporated into M. smegmatis mc²155. Two types of kanamycin resistant colonies were isolated: small and large. The small colonies were designated mc²889, and the large colonies were designated mc²890.

EXAMPLE 4

Construction of int attP xis (phAE42) and pol (phAE45) Deletion Mutants of L5 Shuttle Phasmid phAE41

Since the entire sequence of the L5 genome is known the entire sequence of the shuttle phasmid phAE41 was deduced after determining the exact site of insertion. As discussed above, restriction analysis allowed for the determination of the site of insertion.

L5 shuttle phasmids have several advantages over L5 phages. Specifically, they are stable constructs for which the sequences can easily be deduced. In addition, they can be manipulated as cosmids in E. coli. These properties allow for easy manipulation of the L5 genome. Manipulation of the L5 genome of phAE41 shuttle phasmid was performed in order to produce shuttle phasmids phAE42 and phAE45, as described below.

In order to generate transposon delivery vectors, it is necessary that the delivery phage not be able to replicate in the recipient cell. Therefore, a derivative of phAE41 which was devoid of the integration functions of L5 was constructed. This construct was achieved by recombining a previously characterized mutant of L5, L5cd31 (see Donelly-Wu, et al., Molec. Microbiol., Vol. 7, pp. 407–417 (1993)), that contained a deletion of the region containing integration functions. In order to achieve this, the L5cd31 mutant and phAE41 were both cleaved with XbaI, an enzyme that cleaves each molecule twice. The XbaI-Fragment containing the deletion of L5cd31 was isolated and ligated to the purified arm containing E. coli cosmid of phAE41. These two fragments were ligated together and packaged into bacteriophage lambda heads. The resulting transducing particles were transduced into E. coli, and clones conferring ampicillin-resistance were identified. Two different orientations of the L5cd31 fragment were found in analyzed E. coli recombinants. The fragment in the correct orientation was capable of producing plaques following transfection of M. smegmatis mc²155 cells. Restriction analysis confirmed that phAE41 had acquired the deletion of L5cd31, thus generating shuttle phasmid phAE42, to which the integration genes had been deleted. Shuttle phasmid phAE42 was deposited with the American Type Culture Collection, Rockville, Md., on May 20, 1994 and catalogued as ATCC No. 69625. This demonstrates that novel L5 shuttle phasmid derivatives can easily be constructed by common cloning methodologies and cosmid technologies known to those skilled in the art, which methods employ packaging in vitro techniques.

It was then determined whether specific genes are essential for the propagation of the L5 mycobacteriophage. The first gene studied was the polymerase (pol) gene of mycobacteriophage L5. A deletion of this gene was constructed in order to determine whether it is essential for replication of the L5 phage in M. smegmatis. To achieve this, the 7.6 kb PvuII-SacII fragment containing the pol gene of L5 was cloned into a pKS Blueskript derivative vector. An internal deletion of the pol gene was then generated with by cleaving this molecule with CleI. This removed 290 bp of the pol gene. The 7.3 kb PvuII-SacII L5 fragment containing the pol deletion was then mixed with the other purified PvuII-SacII fragments of phAE41, ligated, in vitro packaged, and in transduced in E. coli selecting for ampicillin-resistant colonies. Plasmids were isolated and characterized by restriction analysis and one out of 20 was found to have the full complement of the phAE41 parent, except that the 7.6 PvuII-SacII fragment had been replaced with the 7.3 kb deleted PvuII-SacII fragment. One such mutant was denoted phAE45, which was deposited with the American Type Culture Collection, Rockville, Md., on May 20, 1994, and catalogued as ATCC No. 69628. This demonstrates that specific deletion can be readily incorporated into specific genes of L5 and that the genome of the resulting phasmid can be readily amplified for subsequent analyses in M. smegmatis and other mycobacteria. In addition, transfection of 1 μg of phAE45 DNA isolated from E. coli yielded no plaques following transfection of mc²155 cells. In contrast, transfection of mc²155 cells with 1 μg phAE41 DNA yielded 2800 plagues. This inability of phAE45 to form plagues on mc²155 establishes that the L5 pol gene is essential for L5 propagation.

EXAMPLE 5

Construction of L5 Luciferase Shuttle Phasmids phAE43 and phAE44

Figure 5:
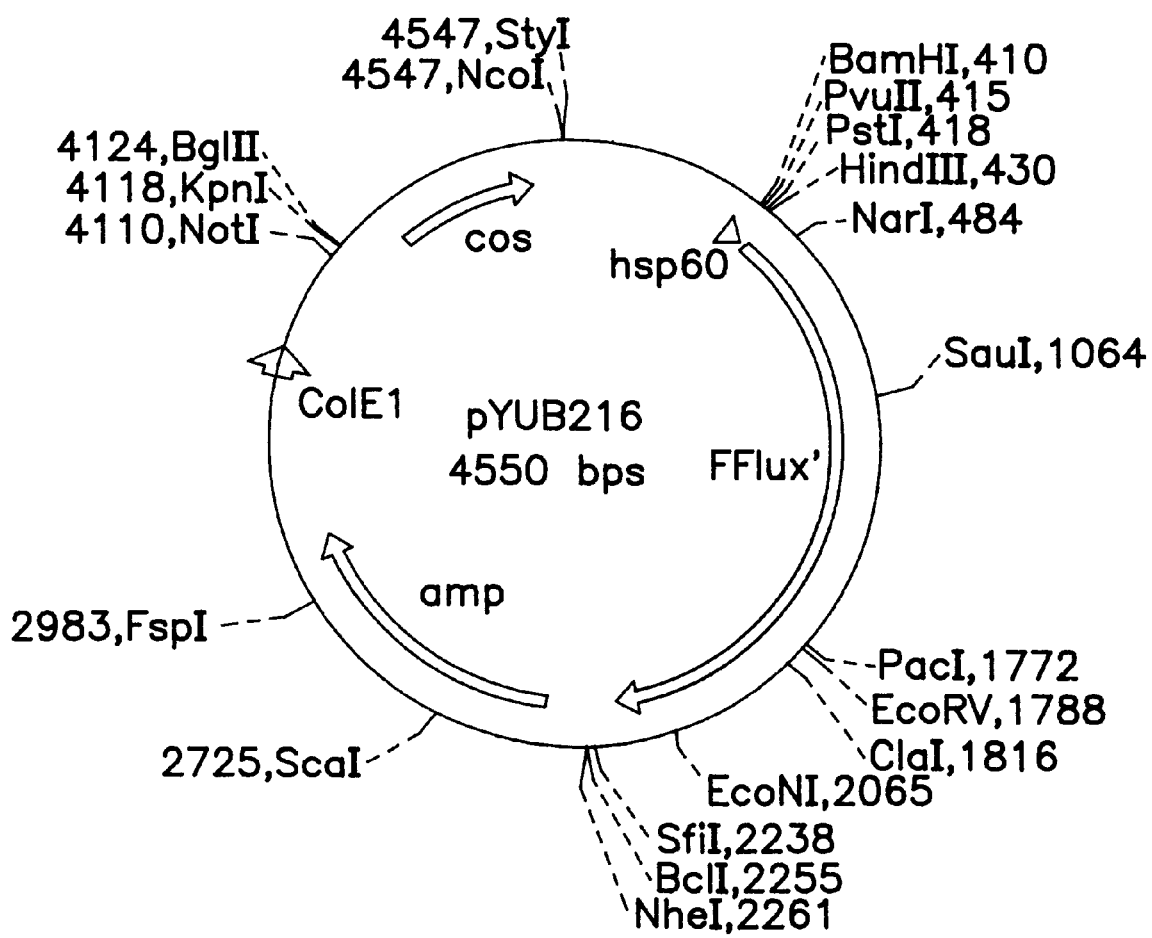
FIG. 5 represents the cosmid pYUB216 which contains the firefly luciferase gene fused to the hsp60 promoter of BCG.
Figure 6:
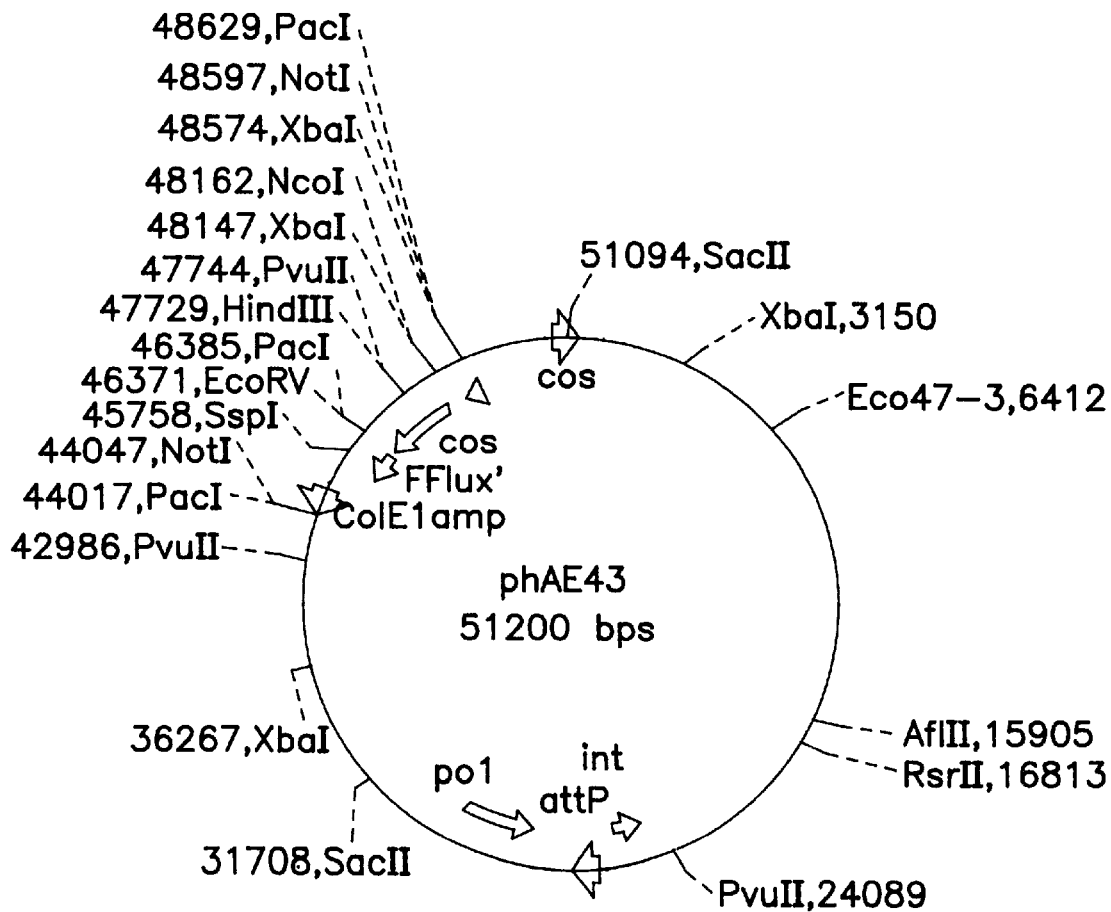
FIG. 6 represents the L5 luciferase shuttle phasmid phAE43 in which cosmid pYUB216 was inserted to replace pYUB328 in phAE41.

PacI, NotI and EcoRI sites flanking the unique BamHI restriction site of pYUB328 were incorporated into L5 shuttle phasmids. Since L5 does not contain PacI, NotI or EcoRI sites, L5 shuttle phasmids can be cleaved with any of these enzymes in order to release virtually the entire pYUB328 cosmid. This facilitates the incorporation of any new cosmid into the L5 backbone. In order to demonstrate this, phAE41 and phAE42 were cleaved with NotI, and the L5 sequences were isolated away from the cosmid portion of these shuttle phasmids. A ligation was set up between the isolated NotI fragment of phAE41 containing the L5 sequences and pYUB216 (see FIG. 5) by the method described by Jacobs, et al., Science, Vol. 260, pp. 819–822 (1993). The resulting ligation was in vitro packaged into E. coli and ampicillin-resistant colonies were selected for. The resulting cosmid molecules were screened. It was found that pYUB216 had been introduced into both orientations into the NotI backbone of phAE41. Transfection of the set of 4 different phAE41 and phAE42 derivative plasmids revealed that only those cosmids in which the Hsp60 promoter was in the same orientation as the leftward promoter of L5 yielded plaques. A single plaque derived from phAE41, which was designated phAE43 (see FIG. 6), was deposited in with the American Type Culture Collection, Rockville, Md., on May 20, 1994 and catalogued as ATCC No. 69626. A single plaque derived from phAE42, which was designated phAE44, was deposited with the American Type Culture Collection, Rockville, Md., on May 20, 1994 and catalogued as ATCC No. 69627. Both phAE43 and phAE44 were then characterized.

The L5 luciferase shuttle phasmids, phAE43 and phAE44, were compared with the TM4 derived luciferase shuttle phasmid phAE40, which was deposited with the American shows that L5 shuttle phasmids allow for the altering of every gene to determine the effect of each gene on luciferase production, and thereby provide tools for the further development of luciferase reporter phages.

EXAMPLE 6

Generation of Insertion Mutations with IS1096-derived Transposons

As discussed hereinabove, it is desirable to obtain plasmids containing transposons for use in obtaining mycobacterial mutants. In order to perform this, several plasmids were utilized. Plasmids used in transposition experiments and their features are indicated in Table 1, below.

TABLE 1

Bacterial strains, plasmids and transposable elements

| Strain, plasmid, or transposable element | Relevant characteristics | Source or reference |
|---|---|---|
| E. coli DH5α | F ϕ80dlαcZΔM15 endA1 recA1 hsdR17 glnV thi-1 λ⁻ gyrA96 relA1 Δ(lαcZYA-αrgF)U169 | Bethesda Research Laboratories |
| M. bovis BCG | Pasteur strain | Institut Pasteur |
| mc$^2$789 | M. bovis BCG[chr::Tn5367]met | This study |
| mc$^2$797 | M. bovis BCG[chr::Tn5367]leu-1 | This study |
| mc$^2$798 | M. bovis BCG[chr::Tn5366]leu-2 | This study |
| mc$^2$826 | M. bovis BCG#12[chr::Tn5367] | This study |
| mc$^2$827 | M. bovis BCG#13[chr::Tn5367] | This study |
| mc$^2$828 | M. bovis BCG#14[chr::Tn5367] | This study |
| mc$^2$829 | M. bovis BCG#21[chr::Tn5368] | This study |
| mc$^2$830 | M. bovis BCG#22tchr::Tn5368] | This study |
| mc$^2$831 | M. bovis BCG#23[chr::Tn5368] | This study |
| mc$^2$849 | M. bovis BCG#11[chr::Tn5367] | This study |
| mc$^2$850 | M. bovis BCG#15[chr::Tn5367] | This study |
| mc$^2$851 | M. bovis BCG#16[chr::Tn5367] | This study |
| mc$^2$852 | M. hovis BCG#17[chr::Tn5368] | This study |
| mc$^2$853 | M. bovis BCG#18[chr::Tn5368] | This study |
| mc$^2$854 | M. bovis BCG#19[chr::Tn5368] | This study |
| mc$^2$855 | M. bovis BCG#20[chr::Tn5368] | This study |
| mc$^2$856 | M. bovis BCG#24[chr::Tn5368] | This study |
| mc$^2$857 | M. bovis BCG#25[chr::Tn5367] | This study |
| mc$^2$858 | M. bovis BCG#26[chr::Tn5367] | This study |
| mc$^2$859 | M. bovis BCG#27[chr::Tn5367] | This study |
| mc$^2$860 | M. bovis BCG#28[chr::Tn5368] | This study |
| mc$^2$861 | M. bovis BCG#29[chr::Tn5368] | This study |
| Bluescript II KS+/− | pUC derivative, Amp$^r$ | Stratagene |
| pMV261 | contains oriE, oriM and αph genes | (38) |
| PYUB8 | pBR322 derivative containing oriE, αph and tet genes | |
| pYUB53 | pYUB8 derivative containing oriE, oriM, αph and tet genes | (22) |
| pYUB285 | ΔoriM, contains oriE and tet genes and Tn5367 | This study |
| pYUB297 | αoriM, contains oriE and tet genes and Tn5368 | This study |
| pYUB305 | αoriM, contains oriE and tet genes and Tn5369 | This study |
| PYUB312 | αoriM, contains oriE, αph and tet genes | This study |
| IS1096 | M. Smegmatis insertion sequence | (7) |
| Tn5366 | IS1096 derivative containing αph gene | This study |
| Tn5367 | IS1096 derivative containing αph gene | This study |
| Tn5368 | IS1096 derivative containing αph gene | This study |
| Tn5369 | IS1096 derivative containing αph gene | This study |

Figure 7:
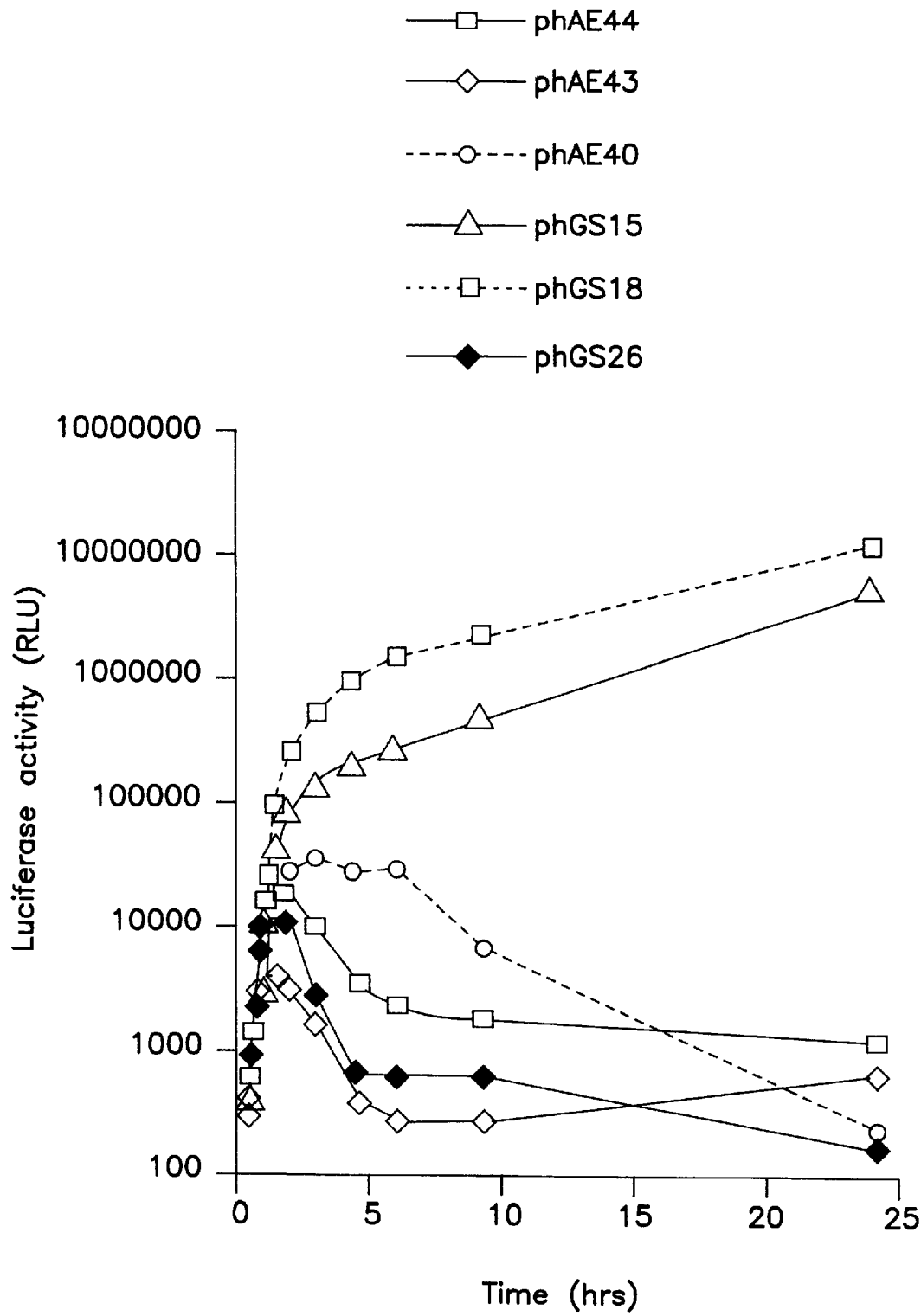
FIG. 7 represents the generation of light by the designated shuttle phasmids in $M.$ $smegmatis$ following infection with luciferase reporter phages and luciferase reporter shuttle phasmids.

Type Culture Collection, Rockville, Md., on Apr. 29, 1993, and catalogued as ATCC No. 75457 for their abilities to generate light in M. smegmatis. FIG. 7 demonstrates that both phAE43 and phAE44 luciferase shuttle phasmids yielded the production of photons in M. smegmatis in 1–3 hours post infection with yields surpassing the phAE40 yield 48 hours post infection. As a control, TM4-derived luciferase shuttle phasmid phAE40 yielded a very rapid burst of light, with maximal yields two to three hours post infection. This demonstrates that L5 shuttle phasmids can deliver luciferase genes to mycobacteria. In addition, this All plasmids have a ColE1 origin and an aminoglycoside 3′-phosphotransferase (aph) gene from Tn903 encoding kanamycin/neomycin resistance. This aph gene was PCR amplified from pKD348 (Derbyshire) to include a trp transcriptional terminator for use in transposon constructs. pYUB8 additionally has a tet gene; pYUB53 was derived from pYUB8 with the addition of the entire mycobacterial origin of replication from pAL5000; and pMV261 has a fully functional oriM, consisting of ORFs 1 and 2 from pAL5000. The remaining plasmids containing IS1096 were constructed as described herein. The DraIIi deletion internal to the oriM was performed by digestion followed by T4 DNA polymerase treatment (Pharmacia). *E. coli* was transformed with plasmids by electroporation (Bio-Rad); or the CaCl$_2$ procedure using pretreated cells (Bethesda Research Laboratories). Plasmids were prepared from *E. coli* by both Birmboim/CsCl$_2$ and column (Quiagen) methods. *M. bovis* BCG cells were transformed by electroporation after washing in 10% glycerol, and then 4 mls complete media M-ADC-TW containing 0.5% casamino acids and 20 μg/ml tryptophan were added, followed by incubation overnight at 30° C. and plating on Middlebrook 7H10 with glycerol, ADC, cyclohexamide, amino acid supplements and kanamycin at 20 μg/ml. Colonies were counted after 3 weeks incubation at 37° C.

In order to perform Southern blotting and hybridization, single *M. bovis* BCG colonies were grown in 10 mls MADCTW containing kanamycin and expanded 1:50 for preparation of DNA. Whole DNA was prepared from 50 ml cultures, by a ten fold scale up of the CTAB method (see van Soolingen et al., *J. Clin. Microbiol.*, Vol. 29, pp. 2578–2586 (1991)). DNA concentration was estimated by agarose gel electrophoresis and approximately 2 μg was digested with restriction enzyme and run on a 0.7% or 1% agarose gel at 40 V overnight. The DNA was transferred to nylon membrane (ICN). Hybridization was performed using plasmid pYUB285 as a probe labelled with [α-$^{32}$P]dCTP as described by Cirillo et al., *J. Bacteriol.*, Vol. 173, pp. 7772–7780 (1991). The sizes of fragments hybridizing on KpnI and BamHI Southern blots were estimated using the mobilities of standard DNA markers run on each gel.

In order to isolate integrated transposons and perform sequence analyses, KpnI-digested fragments containing the integrated transposon were cut from an agarose gel and cloned into Bluescript II KS+ (Promega) using kanamycin selection. Outward primers based on the sequence of IS1096 were used with the Sequenase version 2.0 and the Longranger (United States Biochemical) acrylamide gel reagents. Sequences of the insertion sites were obtained for both DNA strands.

Auxotrophs were then isolated. Colonies obtained on pYUB284 and pYUB297 transformation were picked using wooden sticks into 96-well plates containing complete medium. They were grown up and washed twice in minimal (M-ADC-TW) medium before being replicated onto agar plates with and without amino acid supplement using a 96-prong template (Dankar). Candidates were further streaked from the original 96-well plate to check their auxotrophy, and auxonographic analysis was performed on washed cultures as described by Kaplana et al., *Methods Enzymol.*, Vol. 204, pp. 139–180 (1991).

Figure 8:
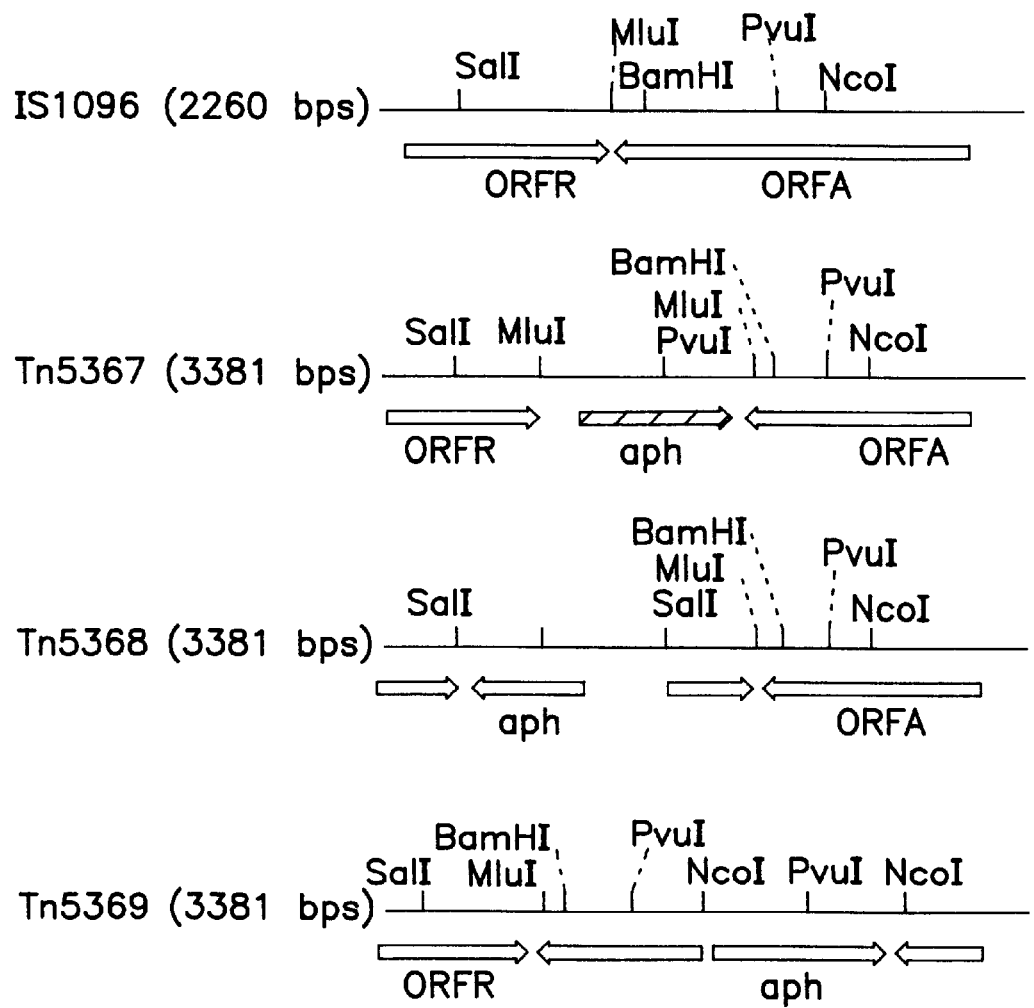
FIG. 8 represents the $M.$ $smegmatis$ insertion element IS1096 and transposons derived from it. The IS element has two major ORFs; ORFA and ORFR (marker by filled arrows), bounded by inverted repeats (IRs). Transposons were constructed by inserting an aph gene (shaded arrow), between the ORFs, into the MluI site (Tn5368), or into a SalI site within ORFR (TN5368); or in an NcoI site within ORFA (Tn5369). Relevant restriction sites are indicated.
Figure 9A:
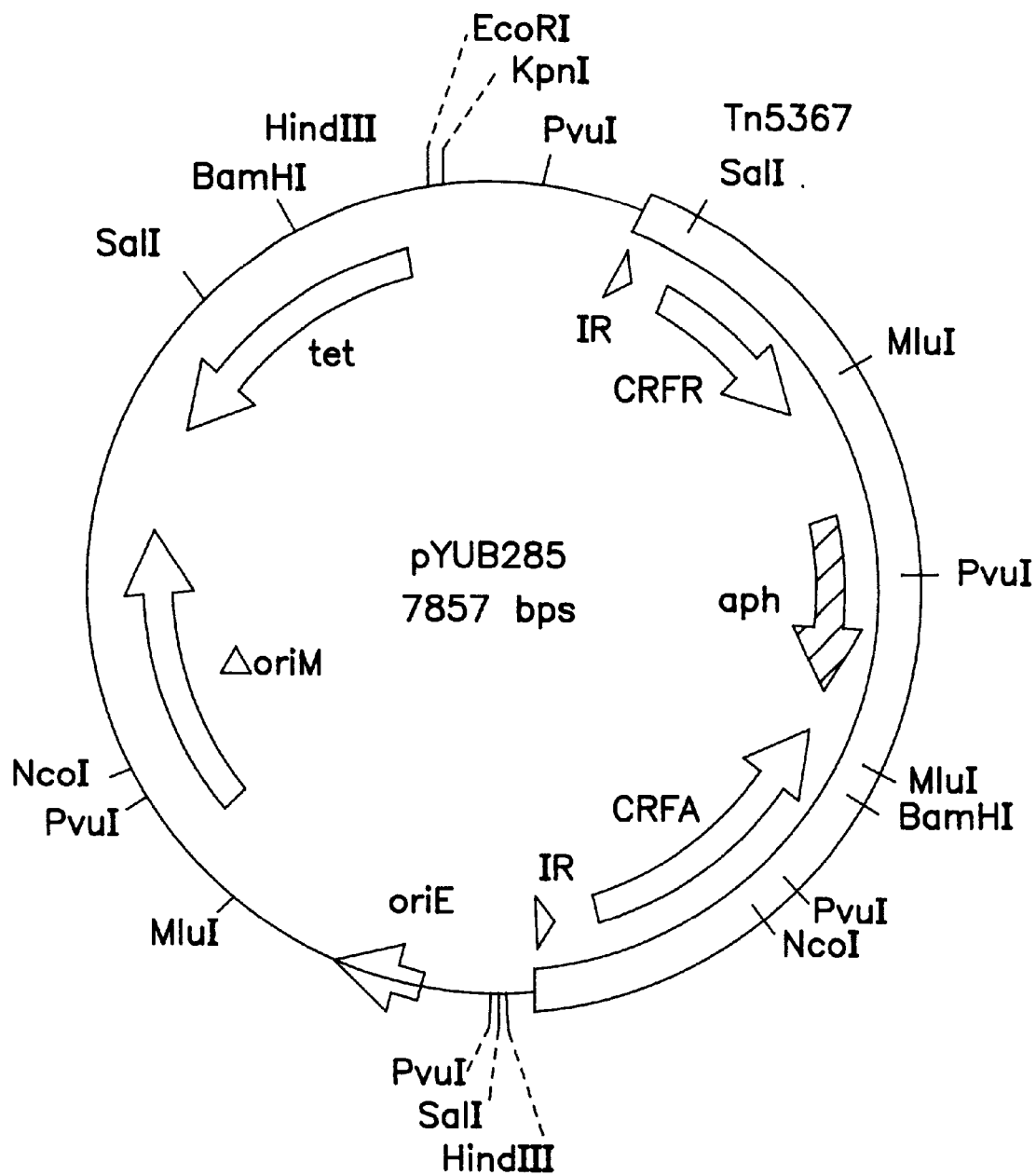
FIG. 9 represents plasmid constructs used to assess transposon activity in $M.$ $bovis$ BCG. All plasmids contain an aph gene for kanamycin resistance, which constitutes part of the transposons in pYUB285, pYUB297 and pYUB305. They also have a disabled oriM (represented by a single arrow) which contains a 556 bp deletion, marked by a bar. pYUB312 contains the aph gene outside the IS element, so transformants will only be seen if integration of the plasmid has occurred.
Figure 9B:
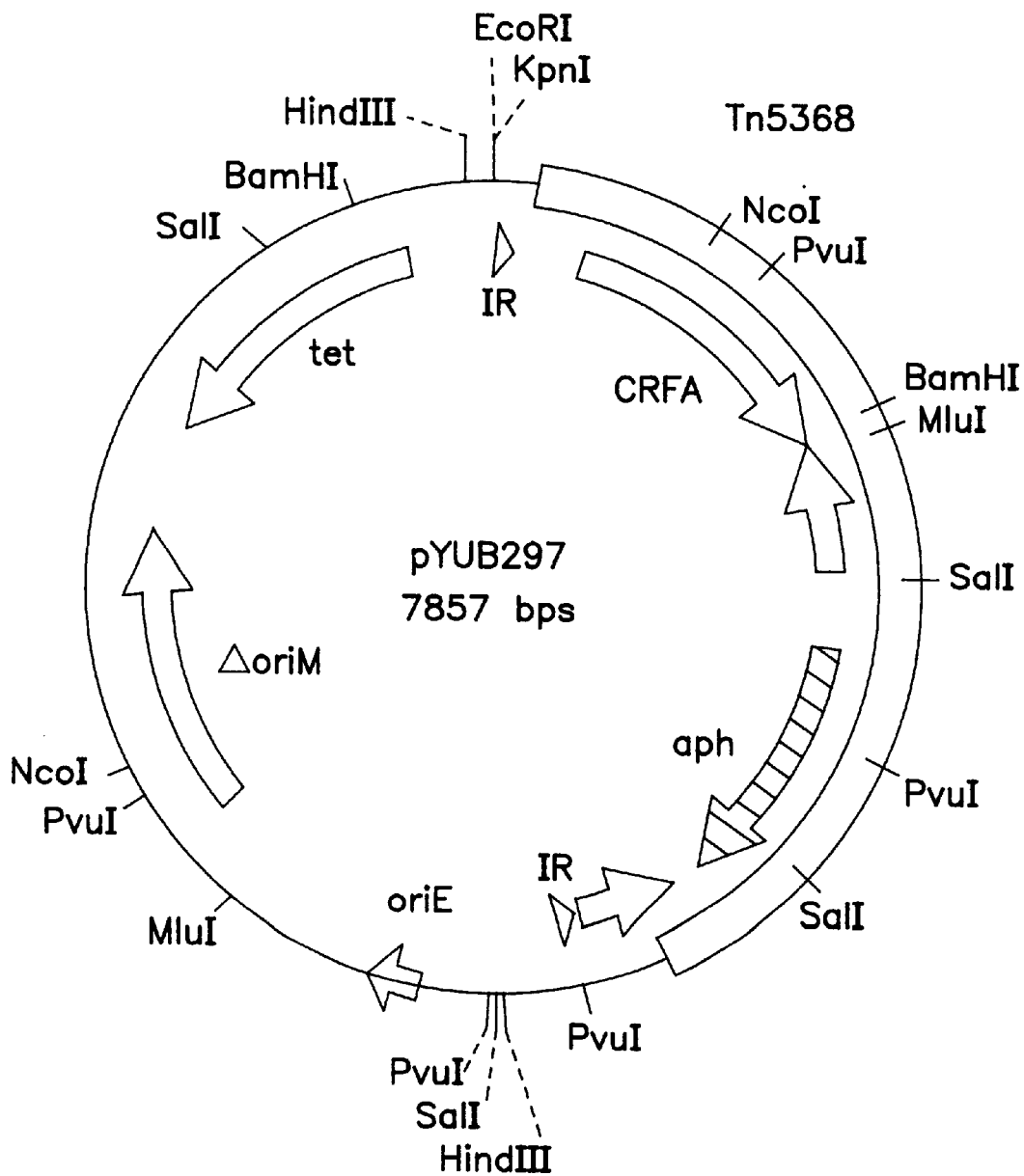
Figure 9C:
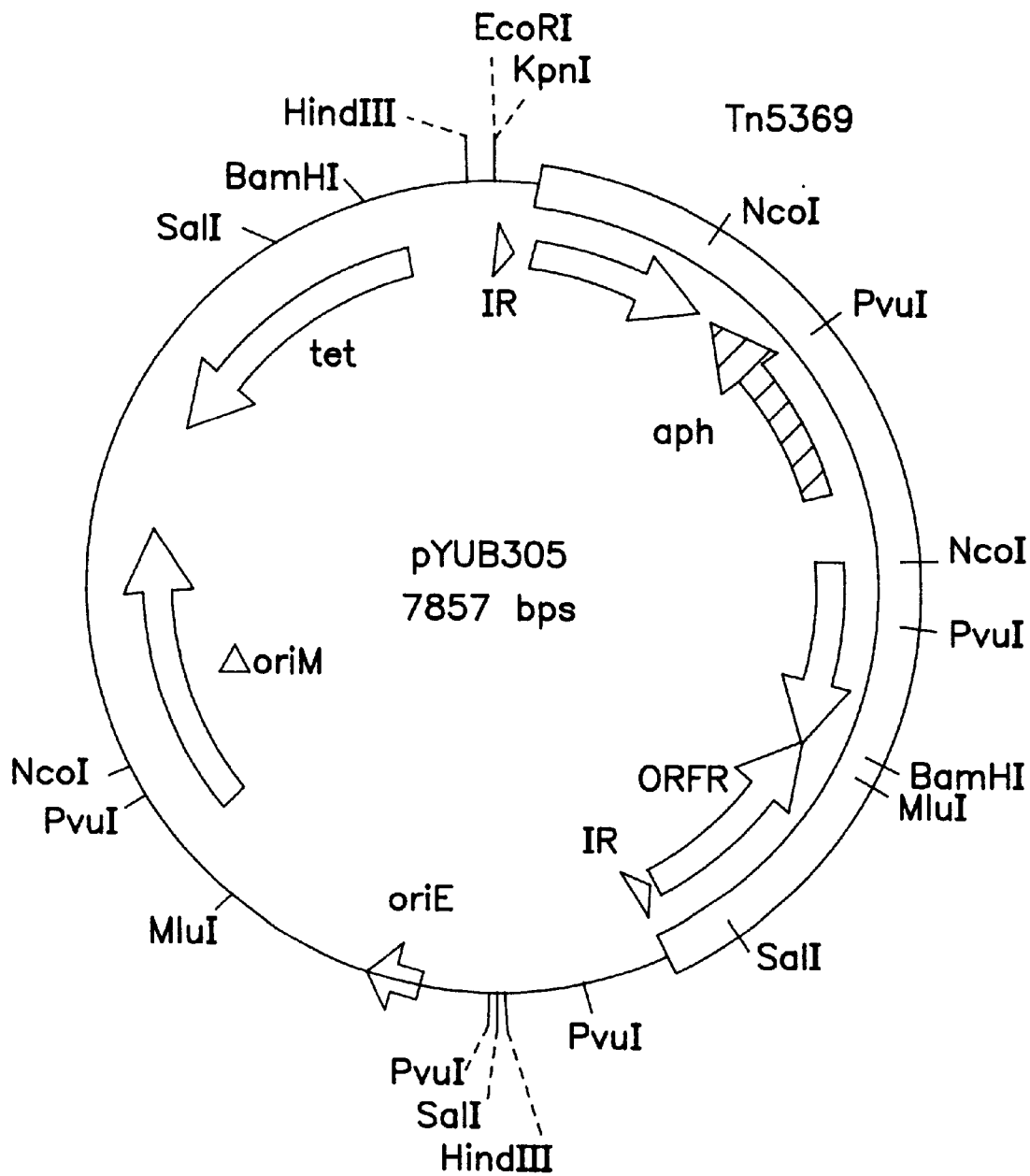
Figure 9D:
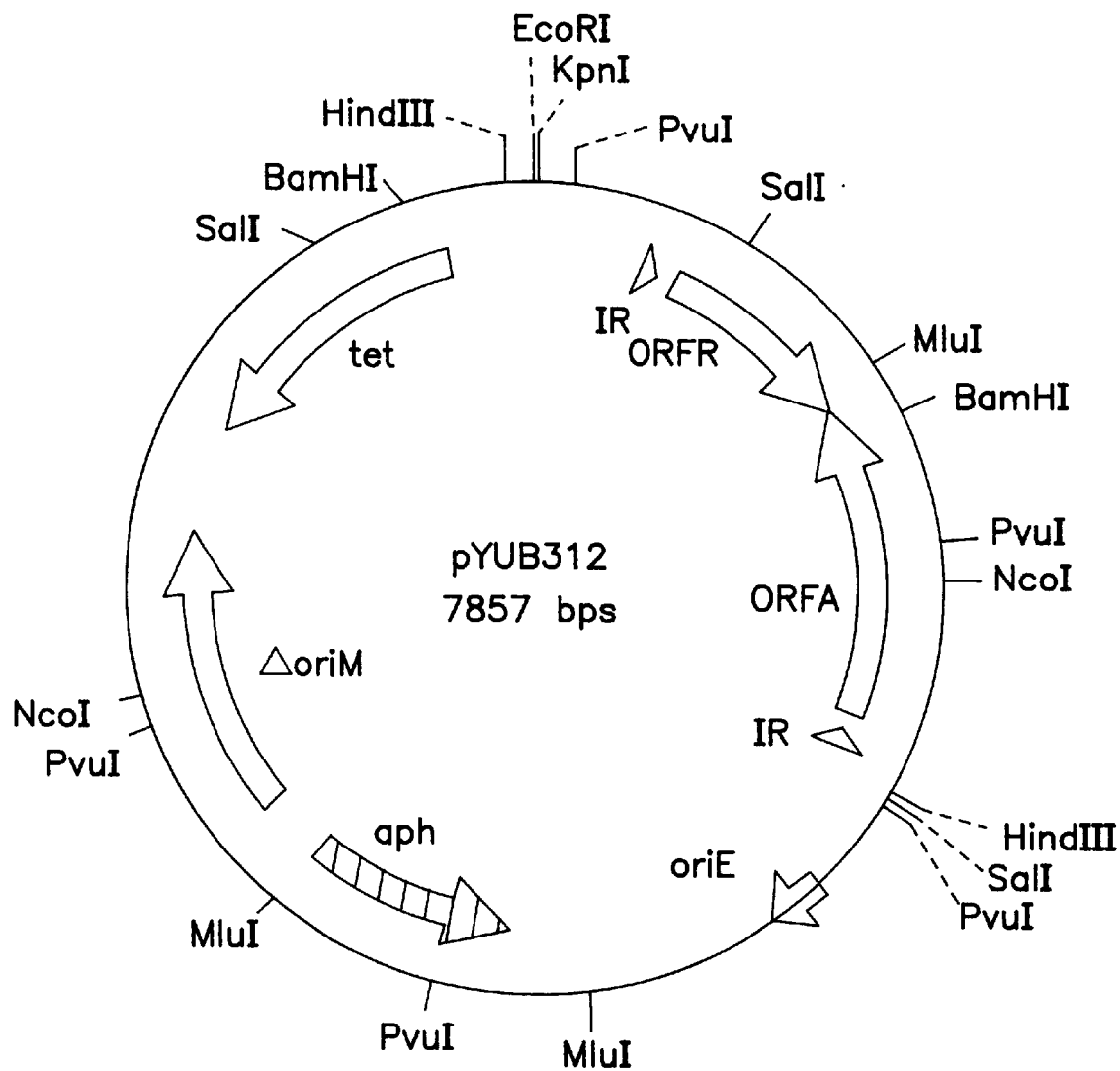

IS1096-derived transposons were constructed. The kanamycin resistance gene (aph) from Tn903 was PCR-amplified and cloned into the unique SalI, MluI or NcoI sites in the insertion sequence IS1096. This created a set of three transposons, having the aph gene in each of the open reading frames of IS1096, as well as between them. The elements are shown in FIG. 8. Tn5368 has the aph gene inserted into ORFR, Tn5369 has the insertion in ORFA, and in Tn5367, the aph gene does not disturb either ORF. Tn5366 is identical to Tn5367 but has the aph gene in the reverse orientation. TnpA and TnpR have been denoted ORFA and ORFR, respectively.

In order to construct transposon delivery plasmids, IS1096, with its adjacent lacZ sequences, (100–200 base pairs on each side), was cloned in both orientations into the multicloning site of pGEM7Zf+ (Promega) to create plasmids pYUB234 and pYUB235, thereby enabling excision of the element with EcoRI and HindIII. A third vector, pYUB272, was constructed, with EcoRI and HindIII sites, as well as origins of replication for *E. coli* and mycobacteria and a tetracycline resistance,. tet gene. This plasmid was derived from pMV261 by replacement of the NotI-PstI fragment with a tetR gene obtained by PCR from pYUB53. The transposons Tn5368 and Tn5369 which were created on pYUB234 were inserted into pYUB272 by ligation after digestion with EcoRI and HindIII. In order to obtain a delivery plasmid which is unable to replicate in mycobacteria, the mycobacterial origin of replication (oriM) was inactivated in each of the constructs by an internal deletion using DraIII, which removed 556 base pairs of DNA and a significant part of an open reading frame in the origin of replication.

Tn5367, having an aph gene in the MluI site, was created after ligation of the IS element to pYUB272. Insertion of the aph gene into the MluI site of the IS element necessitated a partial digestion since there is also an MluI site in pYUB272. The construct obtained from insertion into this second site provided a plasmid having the aph gene outside the transposon, which could then be used as a control to monitor any illegitimate integration of the plasmids. DraIII deletions within the oriM were also performed on these two plasmids. The four plasmid delivery constructs, pYUB285, pYUB297, pYUB305 and pYUB312, are shown in FIG. 9.

*M. bovis*-BCG with transposon delivery constructs were transformed. The numbers of kanamycin-resistant colonies resulting from five transformation experiments are shown in Table 2, below. In addition to the transposon delivery plasmids, three additional plasmids were used as controls. The efficiency of transformation was determined with an oriM-containing vector. Either pMV261, or pYUB53 and any illegitimate integration was monitored using either one of two plasmids: pYUB312 with oriM deletion but the aph gene outside the insertion element; or pYUB8 which has no insertion element or mycobacterial origin, but has an aph gene. A control of cells alone having no plasmid was also electroporated and plated in an identical fashion to the samples to estimate the level of spontaneous resistance to kanamycin ("background").

TABLE 2

| | *M. bovis* BCG transformation | | | | | | |
|---|---|---|---|---|---|---|---|
| | Plasmid | | | | | | |
| Experiment[a] | pYUB285 | pYUB297 | pYUB305 | pYUB312 | pYUB8 | none | oriM$^+$/μg[c] |
| 1 | 255 | — | — | — | 14 | — | 4.5 × 10$^4$ |
| 2 | 155 | 104 | — | — | 16 | 31 | 1.5 × 10$^4$ |
| 3 | 426[b] | 225 | — | 59 | — | 60 | 5 × 10$^4$ |

TABLE 2-continued

M. bovis BCG transformation

| Experiment[a] | pYUB285 | pYUB297 | pYUB305 | pYUB312 | pYUB8 | none | oriM+/µg[c] |
|---|---|---|---|---|---|---|---|
| 4 | 67 | 98 | 18 | 3 | — | 6 | $4.4 \times 10^4$ |
| 5 | 325 | — | 60 | 41 | — | 36 | $1.3 \times 10^5$ |

[1]Within each experiment, the same amount of plasmid was transformed; Experiment 1: 02 µg; Experiment 2: 5 µg and Experiment 3–5: 400 ng, except;
[b]1 µg plasmid was used.
[c]For the oriM+ control plasmid, 0.2 µg–0.4 µg was used, and numbers are represented as transformants per µg. Two different plasmids were used; Experiments 1 and 2: pYUB53 and Experiments 3–5: pMV261.
[d]Recovery conditions after electroporation were 37° C. instead of 30° C.
— Dashes represent data not obtained.

The results show that in each experiment there is a transformation frequency of $10^4$–$10^5$/µg with the oriM-containing plasmid, and a number of kanamycin-resistant colonies arising from transformation with pYUB285 or pYUB297. These numbers are well above background from any of the controls and shows transposition. Furthermore, while pYUB285 contains Tn5367 having both ORFs of the IS element intact, pYUB297 carries Tn5368 in which ORFR is disrupted, implying that this ORF is not required for transposition. In addition, the numbers of colonies obtained for pYUB305, the construct carrying Tn5369, in which ORFA is disrupted, are sharply reduced to close to background levels, suggesting that this ORF is required for transposition and is likely to be the transposase. There is no evidence of illegitimate integration of plasmids since transformation with pYUB312 or PYUB8 yields numbers at background levels.

Figure 10A:
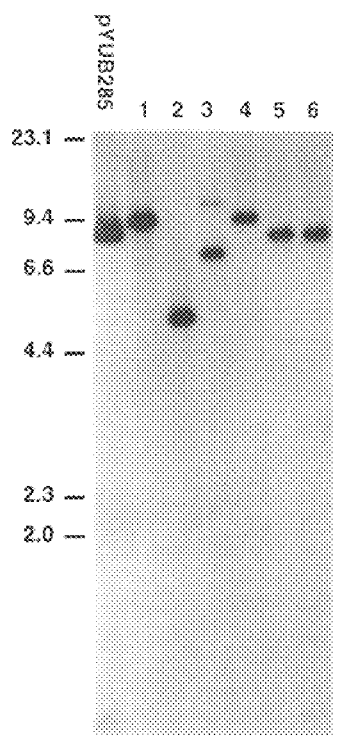
FIG. 10 is comprised of FIGS. 10A, 10B and 10C, and represents Southern blots of six clones resulting from transposition with Tn5367 (1–3) and Tn5368 (4–6). Lane 1, $mc^2826$; 2, $mc^2827$, 3, $mc^3838$; 4, $mc^2829$; 5, $mc^2$ 830 and 6, $mc^2831$. M, pYUB285; s, pYUB297. DNA was digested with A: KpnI, B: BamHI and C: PvuI. Blots were probed with pYUB285 and mobilities are indicated by markers in kbp.
Figure 10B:
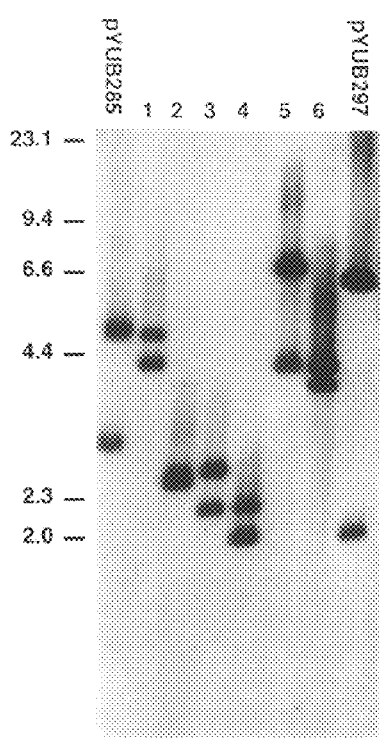

In order to perform analysis of kanamycin-resistant colonies using Southern blotting, twenty colonies arising from transformation of pYUB285 and pYUB297 were picked at random, grown up in the presence of kanamycin and examined by Southern blotting using three different enzymes and plasmid pYUB285 as probe. The Southern blot results of six of such clones, strains mc$^2$826–mc$^2$831, are shown in FIG. 10. Using KpnI, one fragment hybridizes in each clone (see FIG. 10A), since there is no KpnI site in the transposon. To verify that insertion was random, BamHI was also used. This enzyme cuts once within the transposon, and when probed with plasmid, two bands are seen, corresponding to fragments obtained from the transposon's insertion into the chromosome (see FIG. 10B). These fragments appear to be of random size, and indicate that mc$^2$830 and mc$^2$831, which yield similar-sized KpnI fragments, are not identical clones.

Figure 10C:
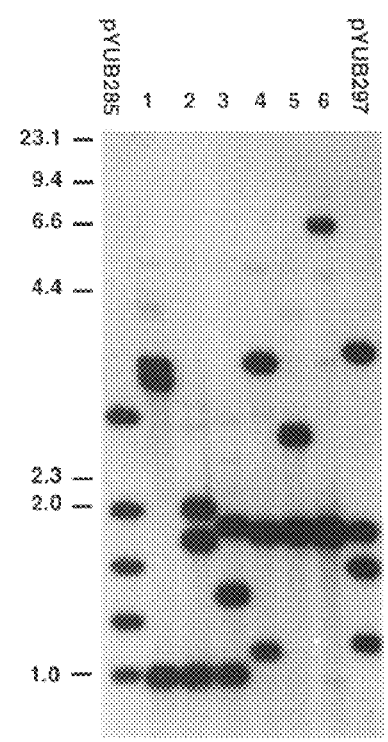

Digestion with PvuI and hybridization with plasmid was carried out in order to determine whether any plasmid sequences were present which would suggest either the presence of cointegrate intermediates or an illegitimate recombination event. The results are shown in FIG. 10C. Digestion of the delivery plasmids with PvuI yields several fragments, including one internal to the transposon (see FIG. 9). If transposition had occurred by simple insertion rather than replication and cointegrate formation, the expected bands from the transposon-containing clones would include this internal fragment and two additional bands resulting from the insertion of the transposon into the chromosome. Three bands were seen with Tn5367 insertions mc$^2$826, mc$^2$827, mc$^2$828, each with expected internal band as well as two unique bands of differing size. Results for the clones transformed with Tn5368 show that one of the clones (mc$^2$829) gives three bands, but the other two (mc$^2$820 and mc$^2$831) display only one additional band along with the expected internal fragment, suggesting that deletions of the transposon are occurring. The absence of extra bands, however excludes the possibility of plasmid integration.

Figure 11A:
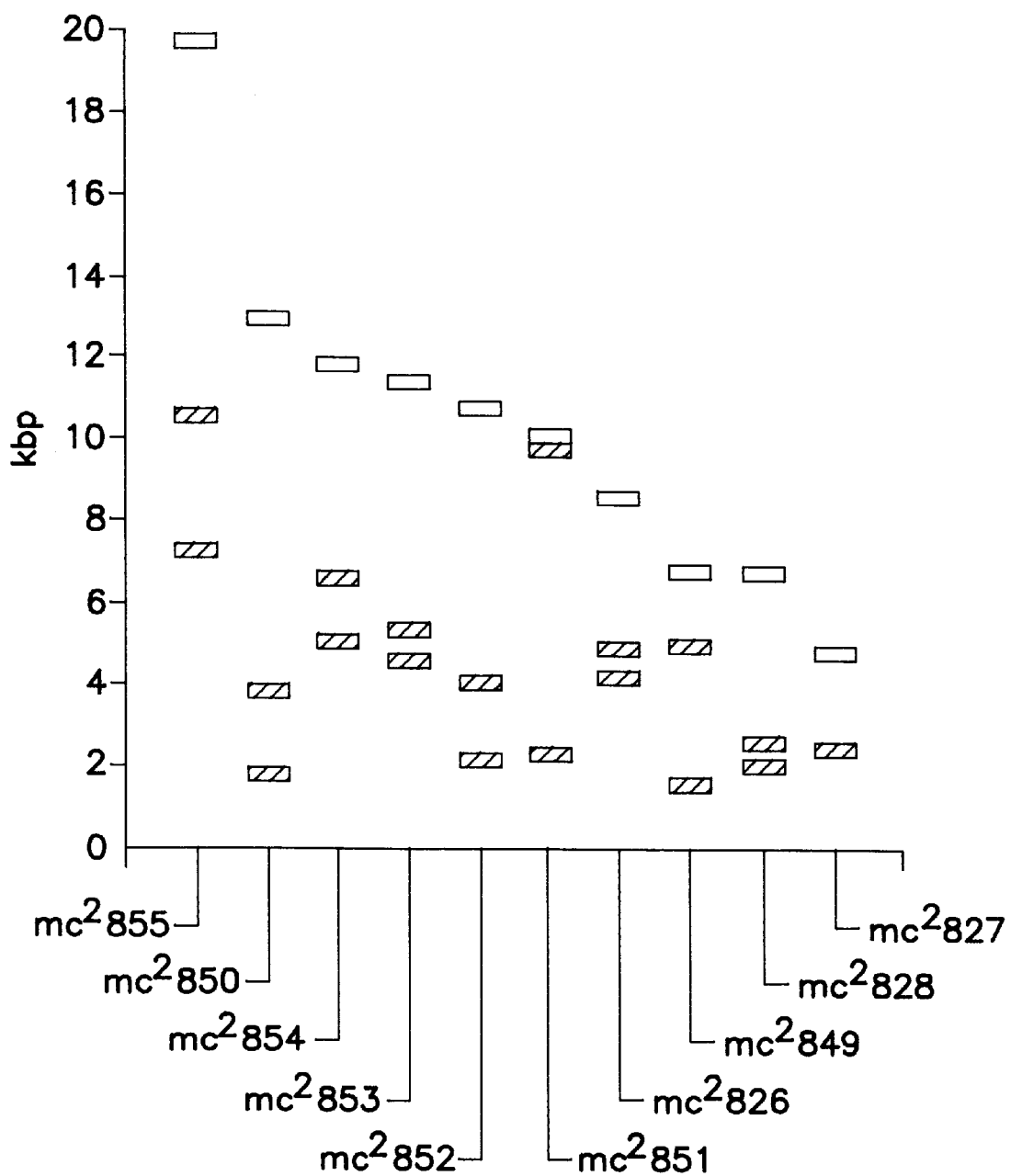
FIG. 11A and 11B are graphical representations of the sizes of restriction fragments obtained from a total of nineteen BCG clones picked at random.
Figure 11B:
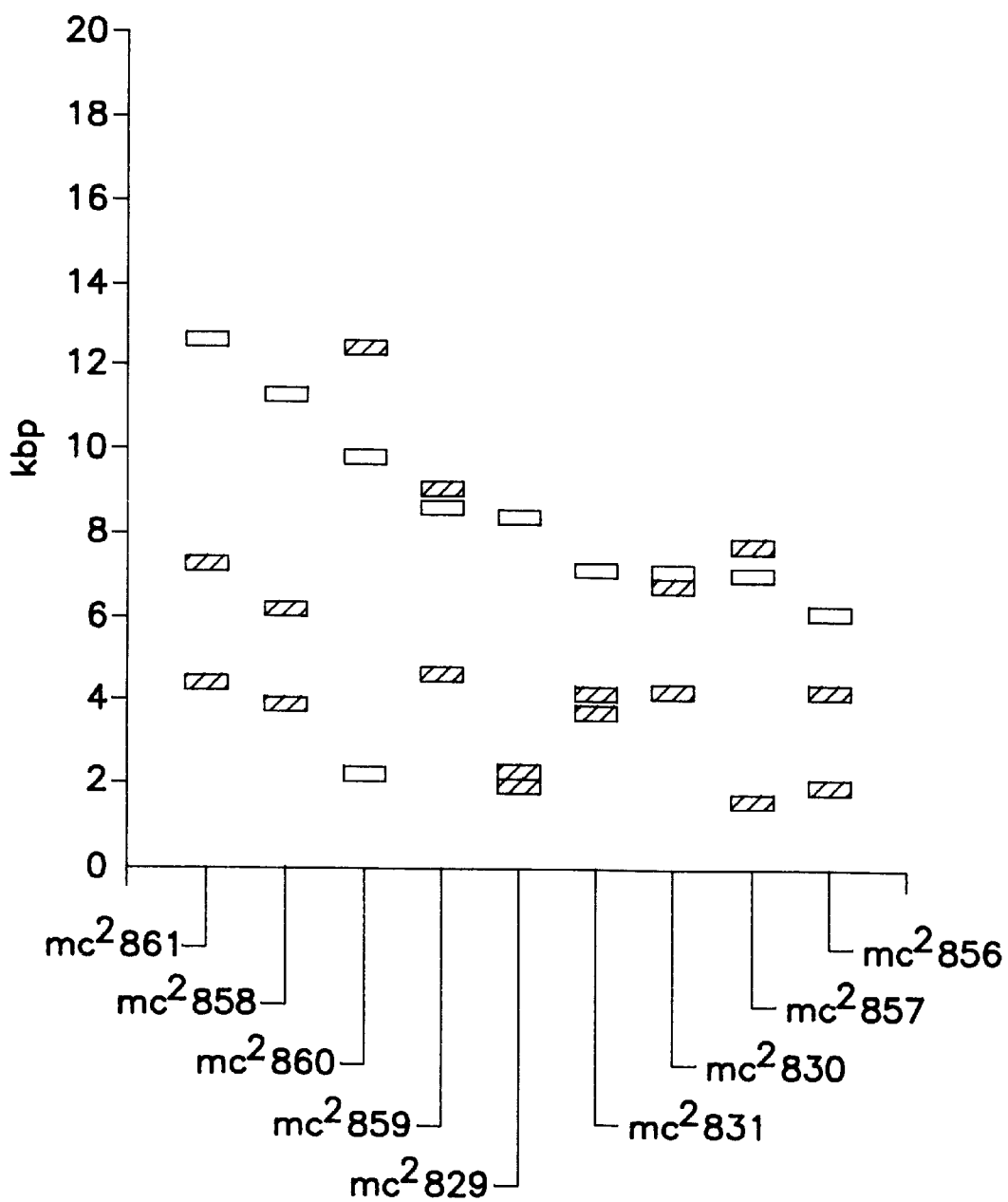

Of the 20 colonies analyzed in total, one clone did not hybridize on Southern blot, suggesting that its kanamycin resistance was due to a spontaneous mutation. The results of Southern blots of the remaining 19 clones with KpnI and BamHI were analyzed and are represented graphically in FIG. 11, to illustrate the random nature of insertion of Tn5367 and Tn5368 into different restriction fragments in each clone. The KpnI fragment sizes were plotted in descending order and the BamHI fragments corresponding to each lone are superimposed. This representation of the data was chosen so that results for each enzyme could be combined to show that the insertion site of the transposon differs for each clone. Even clones showing similar sized KpnI fragments differ in the size of the BamHI fragment into which the transposon was inserted. No plasmid sequences were detected after Southern blotting using PvuI.

Figure 12:
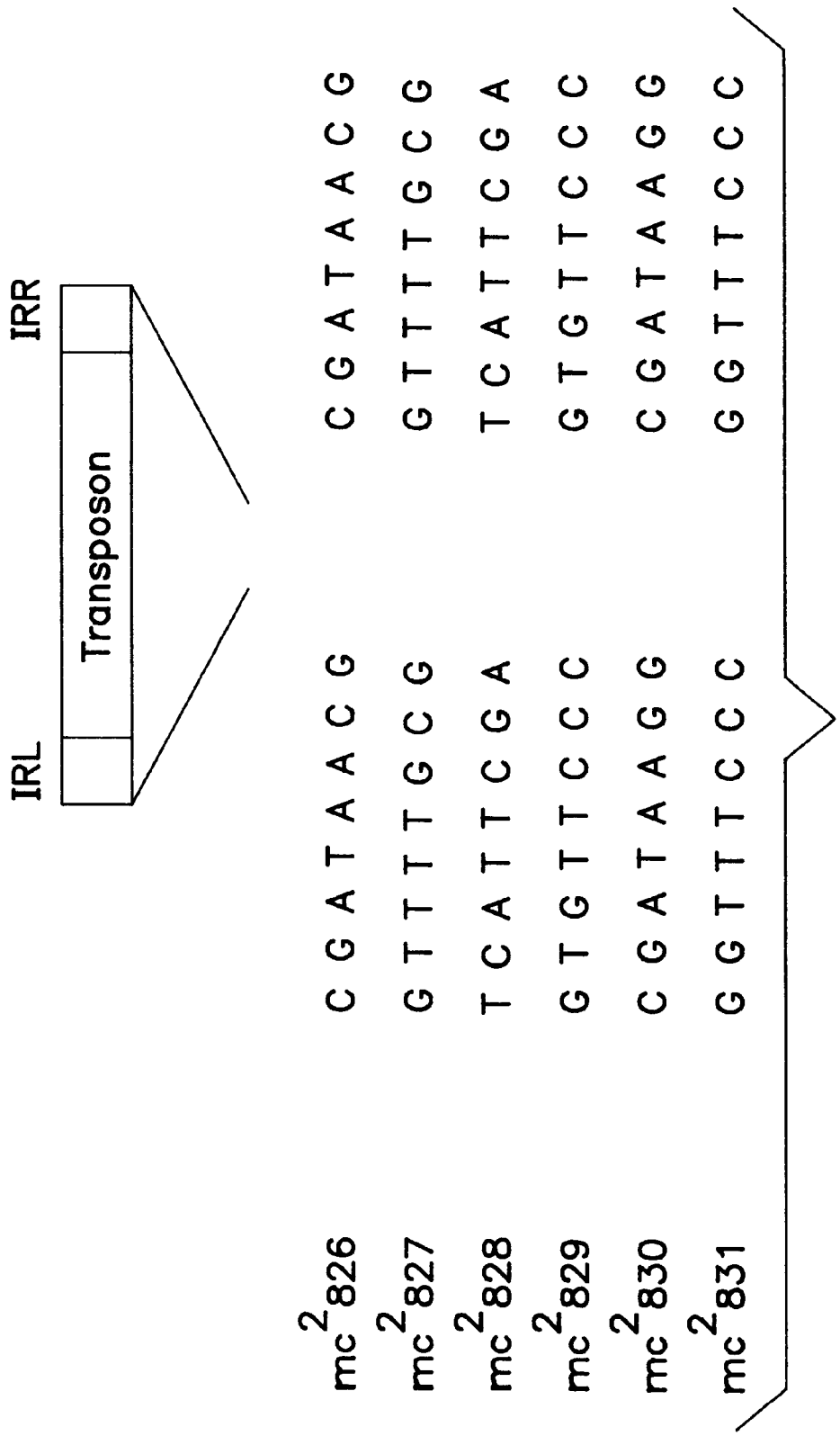
FIG. 12 represents a DNA sequence found on either side of the transposon in the six clones examined. An eight base-pair direct repeat is present in each clone, presumably from duplication of target DNA. $mc^2826$, $mc^2827$ and $mc^{828}$ are clones containing Tn5367 and $mc^2829$, $mc^2830$ and $mc^2831$, contain Tn5368.
Figure 13:
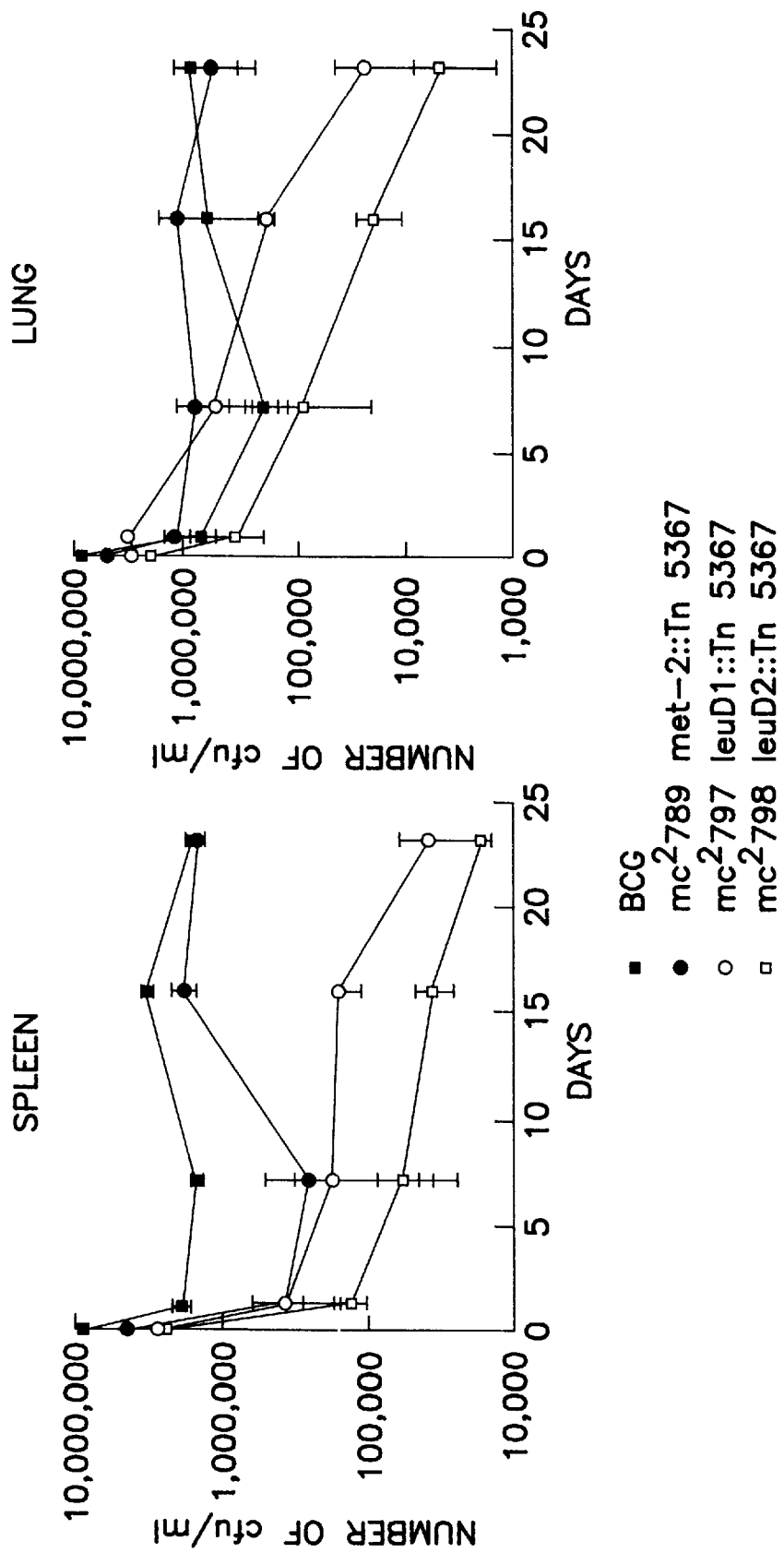
FIG. 13 represents the survival of transposon-derived auxotrophs of BCG in mice. Methionine auxotroph grows in a fashion similar to wild-type BCG as compared to the leucine auxotrophs, which are quickly lost from both the mouse spleen and lungs.
Figure 14:
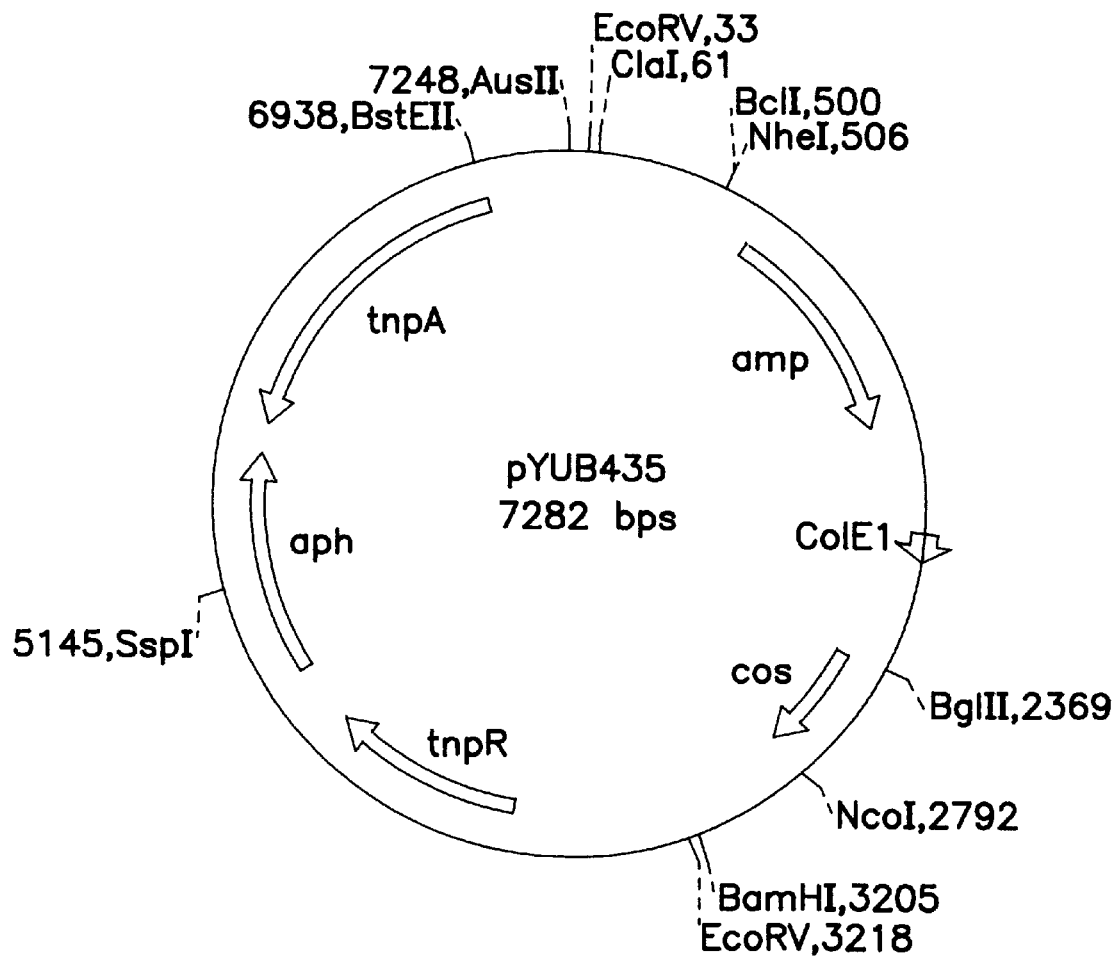
FIG. 14 represents a cosmid pYUB435 containing the IS1096 derived transposon TN5367.
Figure 15:
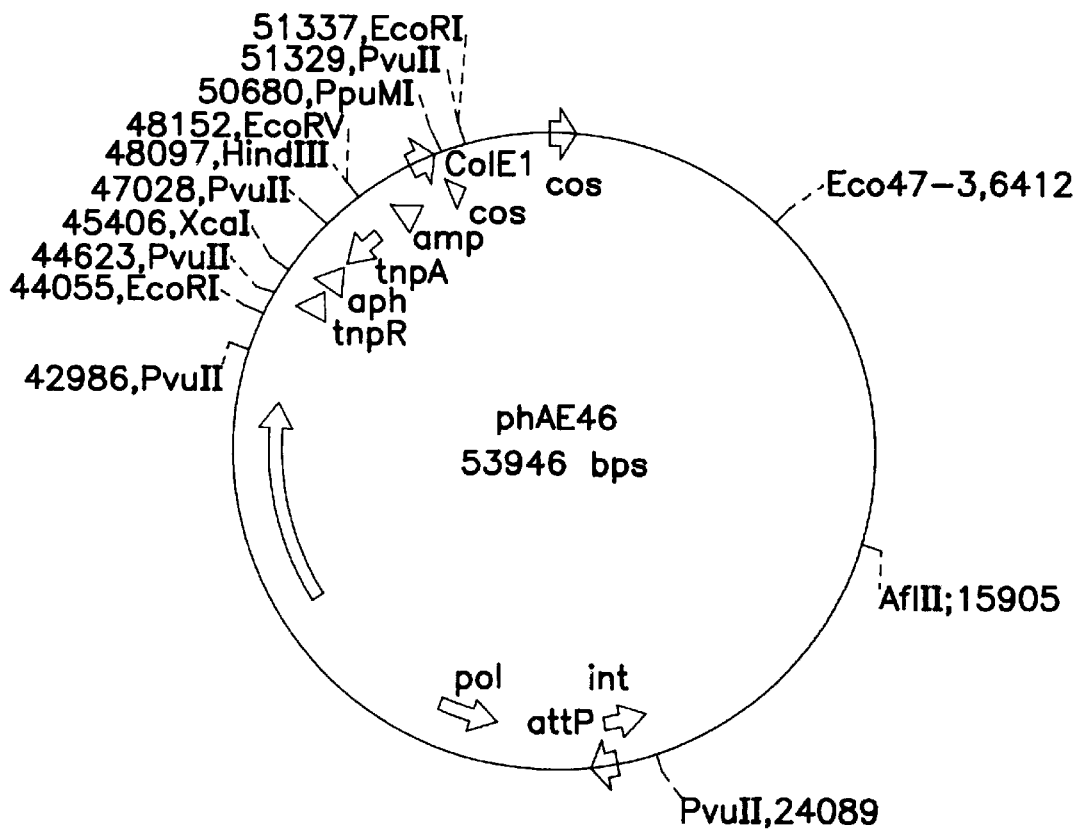
FIG. 15 represents a transposon delivery shuttle phasmid phAE46 derived from phAE41 containing the cosmid pYUB435.

Insertion junctions were then sequenced. IS1096 was previously found to create 8-base pair direct repeats on insertion into its target site (see Cirillo et al., J. Bacteriol., Vol. 173, pp. 7772–7780 (1991)). Therefore, sequencing was performed on the six clones (mc$^2$826-mc$^2$831) described above in order to confirm that the transposons retained this property, and in order to investigate any target-site preference. The sequences of the duplicated target sites are given in FIG. 12. There is a weak consensus at the insertion junctions of XXXTA/TXC/GX, where T always stands at position 4, and there is a preference in the target site for an AT-rich center and GC-rich ends. No similarities were seen between clones comparing 50 base pairs of flanking DNA.

Auxotrophic mutants were isolated and characterized. 923 kanamycin-resistant colonies resulting from the first and second experiments (see Table 2) were arrayed in 96-well plates, grown up, washed and tested for auxotrophy by patching onto plates lacking amino acid supplement. Candidates were tested in auxonography and three auxotrophs were found, one for methionine (Mc$^2$789) and two for leucine ($mc^2797$ and $mc^2798$). The leucine mutants appeared to be distinct, as $mc^2798$ grows more slowly than $mc^2797$. The growth of all three auxotrophs could be supported in liquid or solid minimal media by the addition of the relevant amino acid.

A transposon capable of random insertional mutagenesis in the *M. tuberculosis* complex allows for the isolation of auxotrophic mutants of *M. bovis* BCG and *M. tuberculosis,* which can be used for vaccine development and in new approaches to the study of virulence, such as in vivo expression technology (IVET). It also facilitates the analysis of mechanisms of invasion and survival in the host, and can lead to the identification of new drug targets in *M. tuberculosis.* The ability to mutate genes and locate them easily, is essential in the *M. tuberculosis* complex where gene replacement by homologous recombination prior hereto, has been is difficult.

The inventors have shown that transposons derived from IS1096 do transpose in BCG. The products of transposition appear to be the insertion of one copy of the transposon, with no cointegrates or plasmid sequences. The inference that ORFA is a transposase, and should be referred to as TnpA, is also supported by the recent isolation of insertion element IS1001 from *Bordetella pertussis* and ISAE1 from *Alcaligenes eutrophus*, which both have an open reading frame with homology to ORFA of IS1096 (see Van der Zee et al., *J. Bacteriol.,* Vol. 175, pp. 141–147 (1993) and Kung et al., *J. Bacteriol.,* Vol. 174, pp. 8023–8029 (1992)). Tn610 from *M. fortuitum* and transposon derivatives of IS900 from *M. paratuberculosis,* transpose by a replicative mechanism which can involve cointegrate formation (see Martin et al., *Nature,* Vol. 345,k pp. 739–743 (1990) and England et al., *Mol. Microbiol.,* Vol. 5, pp. 2047–2052 (1991)). It is not uncommon for insertion sequences to exhibit more than one open reading frame. These can be involved in the transposition mechanism, or in the regulation of transposition. If ORFR is indeed a resolvase, it is not required for transposition or resolution in *M. bovis* BCG. However, two of the clones analyzed by Southern blot using PvuI showed evidence of deletions, and both of these clones were derived from transformation with Tn5368, having an insertion in ORFR.

In nineteen out of twenty clones isolated at random, the transposons were found in different sites in the chromosome, as evidenced by restriction fragment size on Southern blotting. In each of the six insertions sequenced, a target duplication of eight base pairs was seen on either side of the element. The DNA sequence of the insertion site differed in each clone analyzed, with only a weak consensus, indicating that there is little constraint on insertion site. Two of the clones have the sequence ATAA at the center. The related IS1001 and ISAE1 both recognize AT-rich targets. IS1001 recognizes runs of As or Ts, and ISAE1 has a preference for A or T at the ends. Both bacteria are also high %G+C organisms. The random nature of the transposition and the ability of the transposons to insert into coding regions is also demonstrated by the isolation of methionine and leucine auxotrophs in BCG.

EXAMPLE 7

Characterization of Methionine and Leucine Auxotrophs of BCG Generated by IS1096-derived Transposons IS1096-derived transposons are able to transpose in BCG. In order to show this, a library of approximately 1000 random insertions of IS1096-derived transposons in BCG was screened for the ability to grow on minimal media after originally selecting on media containing casamino acids. Three auxotrophic mutants of BCG were identified. Auxonography analysis revealed that two of the auxotrophs were leucine-requiring mutants, and one was a methionine-requiring mutant. The reversion frequencies were determined to be between $10^{-7}$ to $10^{-8}$, as shown in Table 3, below. When the BCG auxotrophs were then grown in mice, it was determined that the auxotrophs possessed very properties. The methionine auxotroph resembled BCG when inoculated in mice. In contrast, both of the leucine auxotrophs were cleared rapidly from both the spleens and lungs of the mice (see FIG. 13). This confirms that the IS1096-derived transposons caused different mutations in BCG.

TABLE 3

| *M. bovis*-BCG Strains | | | |
|---|---|---|---|
| Strain | Genotype | Phenotype | Reversion Frequency |
| BCG-Pasteur | wild-type | prototroph | NA |
| $mc^2797$ | leuD1::Tn5367 | leucine auxotroph | $1.6 \times 10^{-7}$ |
| $mc^2798$ | leuD2::Tn5366 | leucine auxotroph | $2.0 \times 10^{-7}$ |
| $mc^2789$ | met-2::Tn5367 | met auxotroph | $1.0 \times 10^{-7}$ |
| $mc^2796$ | zzz::Tn5366 | prototroph | NA |

EXAMPLE 8

Construction of L5 Transposon Delivery Vectors phAE46 and phAE47

By utilizing the cosmid replacement technology in L5 replacement shuttle phasmid phAE41, the pYUB328 cosmid was replaced by the cosmid pYUB435. The pYUB435 cosmid was cloned into the EcoR1 site of both phAE41 and phAE42 in order to generate L5 shuttle phasmids phAE46 (see FIG. 14) and phAE47 (see FIG. 15), respectively. The resulting transposon delivery vectors phAE46 and phAE47 were deposited with the American Type Culture Collection, Rockville, Md., on May 20, 1994, and catalogued as ATCC Nos. 69629 and 69630, respectively. Both of these vectors contain the IS1096-derived transposon Tn5367 which was shown to be able to transpose and make mutations in BCG (see Examples 6 and 7).

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 50341
      (B) TYPE: nucleic acid
      (C) STRANDEDNESS: single
      (D) TOPOLOGY: linear (ii) MOLECULE TYPE:
      (A) DESCRIPTION: L5 shuttle phasmid sequence (iii) HYPOTHETICAL: No (iv) ANTI-SENSE:

(v) FRAGMENT TYPE:

(vi) ORIGINAL SOURCE:
      (A) ORGANISM: L5 mycobacteriophage
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(vii) IMMEDIATE SOURCE:

(viii) POSITION IN GENOME:
      (A) CHROMOSOME/SEGMENT:

(ix) FEATURE:
      (A) NAME/KEY:
      (B) LOCATION:
      (C) IDENTIFICATION METHOD:
      (D) OTHER INFORMATION:

(x) PUBLICATION INFORMATION: None
      (A) AUTHORS:
      (B) TITLE:
      (C) JOURNAL:
      (D) VOLUME:
      (F) PAGES:
      (G) DATE:
      (H) DOCUMENT NUMBER:
      (I) FILING DATE:
      (J) PUBLICATION DATE:
      (K) RELEVANT RESIDUES IN SEQ ID NO:

(xi) SEQUENCE DESCRIPTION: SEQ ID NO: 1:

```
GGCGCTCTCG CATCGCATCG AGTGTTTGCT GTGTCTCTCA TCGTCGCAGG TCAGAAGGGG      60

TAGGGGGGTT CCCCCTAGGG GTCGGTCCTT GACCGGTCGG TTAGGTCGGT TATGCGGCCG     120

AGCCATCCTG TACGGGTTTC CAAGTCGATC AGAGGTAGGG GCCGGCACAG AAACCACTCA     180

CATCAGGGCT GTGCGCCTCC AGGGCGCGTG AACTCCCACA CCCCGGTGTA GTTACATCCC     240

GGAATTGTCT CAGCGCCTCT CAGGGCGCTT CTCATAAACA GTGATCTACG CCACTCCTGA     300

CGGGTGGCTG TCAAGGATAC TCACCTTCCC TACTAATGAG GGGCTAAGAG CCCCTCTCTA     360

TAGAGCGCCG CACAGGCGGC GCGATAAGAG CGCCACCAGG CGCTCATCTA AAGACCGGCC     420

TTGAAGGGCC GGTCATAGAG ATCTATTCGA TCCGGCAACC GCCGGATCTC AAGGCCGCGC     480

CAGTGCGCGG CCCTATAGAG GGGTGACTCA ACTGTGCATG GCACTCGCTC GAGTGCCCAC     540

TGGAGCACTC AACCGGGGAA GTTCGACGTT CTCAACCTGC GAATGACGTT TGAATCGTCA     600
```

```
TCCGCGTACG AAATCCCCGA TCTGCGGCCG ACCGACTTCG TGCCGGCCTA TCTCGCGGCC    660

TGGAATATGC CGCGTCACCG CGATTACGCC GCCAAGAACG GCGGCGCGCT GCACTTCTTC    720

CTTGACGATT ACCGGTTTGA GACCGCGTGG TCGTCCCCCG AGCGCCTTCT CGACCGCGTA    780

AAGCAGGTCG GCGCTGCACT CACGCCGGAT TTCAGCCTCT GGACGAACAT GCCGAAGGCG    840

GCGCAGCTAT GGAACGTCTA CCGCTCCCGC TGGTGTGGCG CGTATTGGCA GTCGGAAGGA    900

ATCGAGGTGA TTCCGACGGC GTGTTGGGCG ACTCCCGACA CGTTCGATTT CTGTTTCGAC    960

GGGATCCCGA TGGGATCGAC CGTCGCAATT TCTTCGATGG GCATTCGCTC TTCAAAAGTC   1020

GACCAGGAGC TTTTCCGGTA CGGACTACGC GAACTCATCG ATCGCACTCA ACCGCAACTG   1080

CTTTTGGCAT ATGGCCAGCT TCGGCATTGC GACGACATGG ATTTACCAGA GGTCCGCGAA   1140

TACCCGACCT ACTGGGACAG ACGACGAAAG TGGGTAACTG CCGATGGGAG GCCGGGGAAG   1200

TAAAGGCGGC CCCGGTCCCG GAACCGGAGC ACGCAACCGC AGAGGCGCTG GAGCCCCCGG   1260

ATCGGGCGGC GTAGGCGGCG TCGGAGGCGG GGGTGGAGCT GCAGGGAGCA GCGGAGGCGG   1320

CAAGGGAACG GCAGCGCCGG TACCGGAGGC GTCACCGGTG GCGGCGGAAG TGGAGCCGGC   1380

GGCGGTGGCA GCAGCCCCAA CACCCCGGTG CCCCCCACCG AGCTGGAGAA GAAGCGCGGC   1440

GAATACAACC AGATCGCCAT CGACGCCCAG AAACAGCACG CGCCCACCGA TGAGAAGCGC   1500

GAGGCCAAGC GCAAGCAACT GATGGATCGA GTCGGAGGAG ACTGGCAGGC TTTGGACCCG   1560

GATCACCACG ACGCCATCAA GGTGGCGATG GATGACGCCA TGCGGAAGAT CCTCTCCGAG   1620

GAGGAGATCG TCCACCGCAC CAAGCACTTC GGCGACCTAC TCGACTCCGG TCGACTCAAG   1680

TCGCTGTTCG AGGTCGGCTT CTCAGCCGGT GGCGACACCC CGACCGAACG CGCCCTCCTC   1740

GAGGACGCCT GGTTCGGCGC AGGCAAGGTT CCCCCGATCT ACTCGGCAAT CGAGTTCAAC   1800

GGCGCTCCGA CAGCCGGCCT CGGCATGTAC GGCGGCACCA AGCTCTACAT GAAGGACTCG   1860

GTCAAGGACC GCGTCACCGT GACCATCGGC GACTCGCTGA TGTCGAGCTG GACGTATTC    1920

CCCGGCCGTC CTGGCGACGG CGTGGGGCTG TGGGCCAGCC TGTCGAAGAT CGAGGGGCTG   1980

GTCGATCCGA GCAAGACCCG CGAAGAGAAC ATGCAGGCGG TGTACGACTC GTTCAAGAAG   2040

TACGGCACCC TGGACGGCTT CATCGAGGCG CAGATCCACG GCGGCGTCCT GGTCGAGGAC   2100

ATCAAGAAGG TCGTGTTCAC GCAGCCGCCG AGCCCGATCT TCACCGATAA ACTGGACGAA   2160

CTTGGAATCC CGTGGGAGGT GCAGTAATGG CGCAGATGCA GGCGACACAC ACAATCGAGG   2220

GGTTCCTGGC TGTCGAGGTG GCCCCTCGGG CGTTCGTCGC AGAGAACGGC CACGTACTGA   2280

CCCGGCTGTC GGCCACGAAG TGGGGCGGTG GCGAGGGTCT CGAGATCCTC AACTACGAGG   2340

GTCCAGGGAC CGTCGAGGTC TCCGACGAGA AGCTCGCCGA AGCCCAGCGG GCCAGCGAGG   2400

TCGAGGCTGA ACTTCGCCGC GAGGTCGGCA AGGAGTGAGC TGGGCCGGCT CAGGCCGGCG   2460

ACAGGAACTA CCAGAGGACT GGGAGCTGAA TTACCGGCTC CCGGTCCTTT CTGCTGCCAA   2520

CTGGCTTTGC CAGATCAACG GTCCCGGATG CGTAAGGGCC GCAACCGATG TCGACCACAT   2580

CAAGCGCGGG AACGACCACA GCCGGTCCAA TCTGCAGGCA GCCTGCCATG TCTGTCACGG   2640

CAAGAAATCA GCCGCCGAGG GCGTAGCCCG ACGGCGGGAA CTTAGAGCCC GGAGGAAGCG   2700

ACCACCCGAA CGCCATCCTG GGCGTCGATA AGCGGGCCAG GTGCCCGCTC CACCCAGGAG   2760

GTGAACAGTG GGCACGCGAG GCCCAATCGG AAAACGAGAT GAAGAGCGGG TTCGTCGGAA   2820

CACCCCGGAC AGTCCAACCG ACACGATCCA GATGCCCGGT CTGGTGACGA TCCCCGAGAT   2880

GGGCGATCTA AGCCACGACG GCCGCACGCA CCAGCTCGTC AAGGACATGT ACGAGTCGAT   2940

CAAGCAGTCG GCAGCCGTGA AGTACTACGA GCCGACCGAC TGGCAGATGG CCCGACTCGC   3000
```

```
CCTCTACACA CTTAACCAGG AACTCATCGC AGCCGAGAAC AACGGCAAGC CCGTGGGCGC    3060

GATGAAGCTC ACTGCCATCA ACCAGATGCT CTCCGCGCTG CTGCTGACCG AAGGTGACCG    3120

ACGCCGCGTC CGACTCGAAG TCGAACGAGC ACCCGCTGAC CCGACAGGCG GGAAGGTCGT    3180

TGACGTGACC GACGTGCTCA AGCAGCGCCT CGCCAAGGCG AGCGGCGGGA GCTGATGGTC    3240

CCCCGAGGGG TTTCTAGAGC CGCTGCCGCT ACCAGCCGCT CCCCCTCGGG GTAGACATCG    3300

AAAGGAACCA CATGGCCGAC CTCGGCAACC CACTCGACCT CGAGATGCTC TGCCTGGTCA    3360

CAGGCCGGGA CTTCCGCTGG ACCATCGATT ACCCGTGGGG TCCGGAGAG CTGTTCCTCG     3420

AACTCGAGAC CGGCGGCGAA CACAACGCGC TGCATCAGGT CTATGTCACC GGGGCGACCG    3480

GAGGCACGTA CACGCTGAAC GTCAACGGCA CCAACACCCC GGCCATCGAC TACAACGACG    3540

TGTCGGAGAA TCCGCAGGGG CTGGCAGGCG ACATCCAAGA CGCTCTGGAC GCAGCCGTCG    3600

GAGCCGGAAA CGCTGTCGTG CATCCGGTCT CGCTGTTCCC TGCGTGGACA CTGAACTTCA    3660

ACCTCAACGC CAGCAAGCCG CTCACCGAGC AGTTGGTCAA CACGATCAAC AAGGCCGCGA    3720

ACGACTTCTT CGACACGTTC GACCAACTAC TTGGGGTCGA CGTGGAGATG ACGGTCACCG    3780

ACACCCTGAA CTTCAAGCTC AAGGTGACCT CGCGGCGCTC GTTCGATGAG GTCGGTGTCG    3840

TCACGTTCGC GGTCGACGTG ACCAGCCAGG CAGTCATCAA CTTCTTCAAC TCCGTCGCCG    3900

AACTCACCGG AGCGGTGAAC ACCGTCAACG TCGACTTCTA CTGGAACCGG ACGTATGACA    3960

TCGAGTTCAC CGGATCCCTT GGGCTGCAGC CGATTCCGGC TACTACAGCC GACATCACCA    4020

ACCTGGCGGG TACCAGCAAG GCCGTCTCAG TCACGGTGGT CGAGCCAGGA AAGAAGAGGC    4080

TGACCATCTG GCCGTTCACG GTCAACGGTG AAACCGCAAC CATCAAGGTC GAGTCCGAAG    4140

AGGCCGACAA GATCCCCAAC CGCTGCCGCT GGCAGTTGGT TCACATGCCG ACCGGCGAGG    4200

CAGCCGGCGG CGATGCAAAG CAGCTCGGCC GCGTTTACCG ACAGCCGAGG TAACACCGCA    4260

CCCATCAGAG ATGGTGGGCC AGACGGCCTT CGGGCCGTCC CCTGACGTGT AGCTCAATGG    4320

CAGAGCGCCC GACTGTTAAT CGGGTGGTTG AAGGTTCGAG TCCTTCCATG TCAGCGAGGG    4380

CTGAACCGGA CCCGTGTCCG GTGTAGGCAC TTTCCGCAGG CGGTTCCCCA GAGCGTGGGG    4440

AGCCCCTGCC CTGTACACGT AGCTCAATTG GTAGAGCAGC GGTCTCCAAA GCCGCCGGTT    4500

CCAGGTTCGA CTCCTGGCGT GTATGCACAC ACCCCTGACT CCTGCTAGCG GAGTGTTCGC    4560

CTTTCGGGCC TGGGGTCTTT TTCCCCGTTC GTCTAATCGG TAAGACACCC GGCTCTGGAC    4620

CGGGCAATTG AGGTTCGAGT CCTTGGCGGG GAGCCAACTT GACATCCACC CGAAAGGAAC    4680

AACATGACCT TCACAGTCAC CCGCGAGAGA GCGCAGTGGG TCCACGACAT GGCCCGCGCT    4740

CGCGACGGTC TCCCCTACGC GTACGGCGGG GCGTTCACCA ACAACCCGAG GGTGTCGACT    4800

GACTGCTCTG GCCTGGTGCT GCAGACCGGG GCTTGGTATG GAGGTCGCAC CGACTGGGTC    4860

GGAAACCGTT ACGGCTCAAC CGAATCGTTC CGGCTCGACC ACAAGATCGT CTACGACCTA    4920

GGGTTCAAGC GGATGCCCCG AGGCGGGCCA GCGGCCTTGC CGATCAAGCC GGTGATGCTC    4980

GTCGGGCTCC AGCACGGAGG CGGCGGGGTC TACTCGCACA CCGCTTGCAC GTTGATGACG    5040

ATGGACCACC CCGGTGGCCC GGTCAAGATG TCCGACCGAG GCGTCGACTG GGAGTCCCAC    5100

GGCAACCGCA ACGGCGTAGG CGTCGAACTT TACGAGGGCG CACGGGCATG GAACGACCCT    5160

CTGTTCCATG ACTTTTGGTA CCTGGACGCA GTCCTCGAAG ACGAAGGAGA CGATGACGAA    5220

TTGGCTGACC CAGTTCTAGG GAAGATGATC CGCGAGATCC ACGCGTGCCT GTTCAATCAG    5280

ACCGCGTCGA CCAGCGATCT GGCGACCCCT GGTGAAGGCG CTATCTGGCA GCTACACCAG    5340

AAGATCCACT CGATTGACGG CATGCTCCAC CCGATCCACG CTGAGCGGCG CGCTCGCGCA    5400
```

```
GGCGATCTCG GTGAGCTGCA CCGAATCGTG TTGGCCGCGA AGGGCTTGGG CGTGAAGCGC    5460

GACGAGGTGA CCAAGCGGGT CTACCAGAGC ATCCTCGCCG ACATCGAGCG GGACAACCCC    5520

GAAGTACTTC AGCGATACAT CGCAGAAAGA GGTGGCCTAT GAGCCCCAAG ATCCGACAGA    5580

CCATCTACCT GCTCGGCACC GCCGCCCCGG CACTGCTGGG CATCGTCCTG ATCTGGGGCG    5640

GGCTCGACGC TGAGTCGGCG GCTGACCTCG GTGACATCAT TGCGGGCGTC GTGTCGATAC    5700

TAGTCTCCGG TGCGCCGGCC GTAGCGGCAG GCACCGTACG CAGCCAGCGC AAGGACGGCA    5760

CGTTGTCCAC CAGCCCGGTG GATCAGGTCA CCAAGGGCGT CGAGCAGGTG CTCGCGGCCA    5820

GGCAGAGTGC CGAGGCTGAA GTCGCGAAGG TCAAGCAGGC GCTGGAGACC GCCGTCAGCG    5880

GTTCTCTCCC CCAGCTCGGC CCGCTGGCCA CGCAGATCCT CAACGTGGCT GACGACACCG    5940

TCTGGCGTCC ATGAGCAAGC CCTGGCTGTT CACCGTCCAC GGCACAGGCC AGCCCGACCC    6000

GCTCGGGCCT GGTCTGCCTG CCGATACCGC ACGGGACGTA CTTGACATCT ACCGGTGGCA    6060

GCCCATCGGC AACTACCCGG CAGCGGCGTT CCCGATGTGG CCGTCGGTCG AAAAGGGTGT    6120

CGCTGAGCTG ATCCTGCAGA TCGAGCTGAA GCTGGACGCA GATCCGTACG GGACTTCGC    6180

GCTGGCCGGC TACTCGCAGG GAGCCATCGT GGTGGGCCAG GTGCTCAAGC ACCACATCAT    6240

CAACCCGAGA GGTCGACTGC ACCGGTTCCT GCACCGGCTC AGGAAGGTCA TCTTCTGGGG    6300

TAATCCGATG CGGCAGAAGG GCTTTGCCCA CACCGACGAG TGGATTCACC AGGTCGCTGC    6360

CTCGGACACG ATGGGCATCC TCGAGGACCG ACTGGAGAAC CTCGAGCAGT ACGGCTTTGA    6420

GGTCCGCGAC TACGCGCACG ACGGCGACAT GTACGCCTCC ATCAAGGAGG ACGACATGCA    6480

CGAGTACGAG GTGGCCATTG GCCGAATCGT GATGAGCGCT AGGCGATTCA TCGGAGGTAA    6540

GGACTCCGTC ATCGCCCAGC TCATCGAGCT TGGACAGCGT CCGATCTGGG AGGGAATCGC    6600

GATGGCCAGA GCCATCATCG ACGCCCTCAC GTTCTTCGCC AAGTCGACCC AAGGCCCGAG    6660

CTGGCCGCAT TTGTACAACC GCTTCCCGGC GGTCGAGTTC CTACGACGAA TCTGAGAAAG    6720

GAGGCGGGGT GAGCCTCAAC AACCACCACC CGGAGCTTGC CCCGTCTCCC CCTCACATCA    6780

TCGGCCCGTC CTGGCAGAAG ACGGTCGATG GTGAGTGGTA TCTGCCTGAG AAGACCCTCG    6840

GCTGGGGAGT CCTGAAGTGG CTCTCCGAGT ACGTGAATAC CCCTGGCGGG CATGACGATC    6900

CGAACCGTCT GGCGACGTTG ATCGCGCTCT CCGAGGCAGG TCTTCTCGAC AACGAGAACA    6960

TGTTCATCCC CACCGACGAG CAGGTACGCC TGGTCCTCTG GTGGTACGCA GTAGATGACC    7020

AGGGCCAGTA CATCTACCGC GAGGGCGTGA TCCGCCGGCT CAAGGGCTGG GGCAAGGATC    7080

CGTTCACCGC CGCGCTCTGC TTGGCGGAAC TCTGTGGCCC CGTAGCCTTT TCACACTTCG    7140

ACGCCGACGG TAACCCGGTC GGCAAGCCGC GTTCAGCCGC GTGGATCACC GTCGCGGCCG    7200

TCAGCCAGGA CCAGACGAAG AACACGTTCT CGCTGTTCCC GGTGATGATC AGCAAGAAGC    7260

TGAAGGCCGA GTACGGCCTG GACGTGAACC GCTTCATCAT CTACTCCGCA GCCGGTGGCC    7320

GTATTGAGGC AGCGACCTCG AGCCCCGCGT CGATGGAGGG TAACCGCCCG ACGTTCGTCG    7380

TCCAGAACGA GACGCAGTGG TGGGGCCAAG GCCCCGACGG CAAGGTCAAT GAAGGCCACG    7440

CGATGGCAGA GGTCATCGAA GGCAACATGA CCAAGGTCGA GGGCTCCCGC ACCCTGTCGA    7500

TCTGCAACGC CCACATCCCC GGCACCGAGA CGGTCGCCGA GAAGGCATGG GACGAGTACC    7560

AGAAGGTCCA GGCAGGCGAC TCTGTCGACA CCGGGATGAT GTACGACGCG CTGGAAGCGC    7620

CGGCCGACAC CCCGGTCTCC GAGATCCCCC CGCAGAAGGA GGATCCCGAG GGATTCGAGA    7680

AGGGCATCGA GAAGCTCCGC GAGGGCCTGC TCATCGCCCG AGGCGACTCC ACCTGGCTGC    7740

CGATAGACGA CATCATCAAG TCGATTCTGT CGACCAAGAA CCCGATCACC GAGTCGCGGC    7800
```

```
GCAAGTTCCT GAATCAGGTA AACGCCGCTG AGGACTCGTG GCTCTCACCG CAGGAATGGA    7860

ACCGGTGCCA GGTCGACCTG GCCAAGTACC TGGATAAGCA CGGCAGGGAG TTCGCTCCGC    7920

TGCAGCGCGG TGACCGGATC ACCCTCGGGT TCGACGGGTC GAAGTCCAAC GACTGGACCG    7980

CGCTCGTCGG CTGCCGTGTC AGCGACGGCC TGCTGTTCGT CATCGACATC TGGGATCCCC    8040

AGAAGTACGG CGGGGAGGTT CCCCGCGAAG ACGTTGACGC CAAGGTCCAT TCGGCGTTCG    8100

CCCACTACGA CGTGGTGGCG TTCCGCGCCG ACGTGAAGGA GTTCGAGGCG TACGTCGACC    8160

AGTGGGGCCG GACCTACAAG AAGAAGCTCA AGGTCAACGC CAGCCCGAAC AACCCGGTGG    8220

CGTTCGACAT GCGCGGACAG CAGAAGAGGT TCGCGTTCGA CTGCGAGCGA CTCGAGGACG    8280

CGGTCCTTGA GGGCGAGGTC TGGCACGACG GCAATCCCGT TCTGCGCCAA CACGTTCTGA    8340

ACGCCAAACG ACACCCAACG AACTACGACG CCATCGCGAT TCGCAAGGTC ACGAAGGACT    8400

CCAGCAAGAA AATCGACGCT GCAGTCTGCG CTGTCCTCGC GTTCGGGGCG AGACAGGACT    8460

ACCTCATGAG CAAGAAGGCC CGTAGCGGCC GGGTGGTGAT GGTTCGATGA CAGCACCGCT    8520

CCCCGGTATG GAGGAGATCG AAGACCCCGC AGTCGTACGA GAAGAGATGA TCTCGGCCTT    8580

CGAGGATGCT TCCAAGGATC TCGCCAGCAA CACCAGCTAC TACGACGCTG AGCGCCGGCC    8640

AGAGGCCATC GGCGTCACCG TCCCGAGAGA GATGCAGCAA CTGCTGGCTC ACGTCGGATA    8700

CCCCAGGCTC TACGTCGACT CAGTCGCCGA GCGCCAGGCC GTCGAGGGTT TCCGCCTCGG    8760

CGATGCCGAC GAGGCTGACG AAGAGCTGTG GCAGTGGTGG CAGGCCAACA ACCTCGACAT    8820

CGAGGCACCA CTGGGCTACA CCGACGCTTA CGTTCACGGC CGGTCGTTCA TCACGATCAG    8880

CAAGCCAGAC CCGCAGCTCG ACCTGGGTTG GGATCAGAAC GTCCCGATCA TCCGCGTCGA    8940

GCCGCCCACC CGAATGCACG CCGAGATCGA CCCCCGGATC AACCGGGTGT CCAAGGCCAT    9000

CCGAGTCGCA TATGACAAGG AGGGCAACGA GATTCAGGCT GCCACGCTGT ACACGCCGAT    9060

GGAGACCATC GGCTGGTTCC GCGCTGACGG TGAGTGGGCT GAGTGGTTCA ACGTCCCGCA    9120

CGGTCTGGGC GTCGTTCCCG TTGTGCCGCT TCCGAACCGG ACCCGGCTCT CGGACCTGTA    9180

CGGCACCAGT GAGATCACGC CCGAGCTTCG GTCGATGACC GACGCGGCGG CGCGCATCCT    9240

CATGTTGATG CAGGCGACCG CCGAGCTGAT GGGTGTCCCC CAGCGCCTGA TCTTCGGCAT    9300

CAAGCCCGAA GAGATCGGCG TCGACTCCGA GACCGGCCAG ACGCTGTTCG ATGCGTACCT    9360

GGCCCGGATC CTGGCGTTCG AGGACGCTGA GGGCAAGATC CAGCAGTTCT CTGCAGCCGA    9420

GCTGGCCAAC TTCACCAACG CGCTCGATCA GATCGCCAAA CAGGTCGCTG CGTACACGGG    9480

ATTGCCTCCC CAGTACCTGA GTACCGCCGC AGACAATCCG GCCTCCGCTG AGGCGATCAG    9540

GGCCGCTGAG AGCCGACTCA TCAAGAAGGT CGAGCGGAAG AACCTGATGT TCGGCGGCGC    9600

ATGGGAAGAG GCCATGCGGA TCGCCTACCG GATCATGAAG GGCGGCGACG TTCCCCCGGA    9660

CATGCTCCGC ATGGAGACCG TCTGGCGAGA CCCGAGCACT CCCACCTACG CGGCCAAGGC    9720

CGACGCAGCC ACGAAGCTGT ACGGCAACGG CCAGGGTGTC ATCCCGCGTG AACGTGCTCG    9780

CATCGACATG GGCTACTCCG TCAAGGAGCG CGAAGAGATG CGCCGATGGG ACGAGGAAGA    9840

GGCCGCAATG GGTCTCGGCC TGTTGGGCAC GATGGTCGAC GCCGACCCGA CGGTCCCAGG    9900

CTCCCCGAGC CCCACGGCAC CGCCGAAGCC ACAGCCGGCC ATCGAGTCGT CTGGTGGTGA    9960

TGCGTGACCG CAGAGGAGTA CGCGGCGGCT CAAGCCGCGA TCACTGCGGG TCTTGCCACA   10020

TACGTCCAGA GGTTCGCTTC GCTCTTCGTC GGTCCAGCTC TCGCTGTAGG TGAGTGGCTG   10080

CGACTGCTGC AGGTGCTGTT CCCCGAAATC CAACGGCGGT ATGCAGATGC TGCCGCCTTG   10140

GGCAGGGACT TCTACGACTC CCAACGCGCA CTACACCACC CAGAGCTGCC CCGGAACGAG   10200
```

```
AGGTTCCGGG GAGAGCTTCG GTGGGAGTGG TTCGTCCAGA ACATGGAGCC CGCTCGAAAA    10260

GAGATGTCGC AGGCCGACTC TCCGCCGAGT GCGACCTCTA AGTTGGCTCT GGCCGCAGTT    10320

CGCGAAGTGG AGATGGCAGC ACGCCGACAG ATCATCGGCG CTGTCAAGAA CGATCCGGCC    10380

CCGCAGATCG TGCAGGGCTG GGCGAGGGTC GCCACCGGGC GCGAAACATG CGCCTGGTGT    10440

CTGATGCTCA TCTCACGGGG TGCCGAGCTG AATCACAAGG GCAACTTCGC CTACAGCTCA    10500

GCGGAAGCCG CAGGGCTCAA CCTCGATGAC GAGACCGTGA TCGACCTCTG GAACGAGTCC    10560

GGTCACGACC TTGAGAAGTT CCGCGAGGAG ACCAGAGAGG ACTTCGAGAA GTGGCACGCA    10620

GGGTGCGACT GTCTGGTGGT CCCGGTCTTC GATGTGCAGA ACTGGCCCGG AAGAGACGCT    10680

GCCCTACGGG CGCAGCAACT TTGGATCGAA GCCAGCGACG AAGCTGACGA CCTCATTGCG    10740

TCAGGCAAGG CCCGCTCCAA GAACAAGAAC ACGGAGACGC TCAACGCGCT CCGACGCCGC    10800

CTAGCACGCG GCGAAATCAC CATGTCCAAC TACGCCCTCG CTGCGTAGTC CCTCGAACCC    10860

CAGGTGGGTT CTCTCAACAT GCCCAGGAGG CGAAAACACA TGTCCGACAA CCCCACTCCC    10920

GAGAGCACCC CAGAGGCCGA GACCCCGGAG GTCGAGAAGC CGATGGAACC GCAGGGCAAG    10980

GTCTTCGATG AAGCGTACGT TCAGTCGCTT CGCCAGGAGG CTGCAGCCGC TCGGGTGGCG    11040

AAGAAGGACG CCGTAGAAGC GGCAGAGGCT CGAGTGAAGG CCGAGTACGA GGCCAAGCTC    11100

GCTGAGCGCG ACACCGCTTA CACCGAACTG CAGAACCAGT TGGGACAGGC GTGGATTGAG    11160

CTGGAGAAGG TCTACCTCTC TCTCGACGCC AAGGTGCCCA ACGACAAGGT TCGGGCGTTT    11220

GTCGAGATCC TCGAAGGCAA CGACAGGGAC AGCATCGCTG AGTCAGTGAA GTCCCGTCTG    11280

GAGCTGGTCG GCGGATTCGG CAACAAGACC CCGAGTCCTG CGTTCGACCC GTCTCAGGGT    11340

CGCGGCGGTA AGCCGCCGAT CCCGCTGAAC GGTGACCCGA TCCTCGAGGC CATCAAGGCC    11400

GCTGTCGGGA TCAAGAAGTA ACCCACCCAA CAGATCTCAA GGAGAGATAA ACAATGGCAG    11460

TCAACCCTGA CCGCACCACG CCGTTCCTCG GCGTGAACGA CCCCAAGGTC GCGCAGACCG    11520

GCGACTCGAT GTTCGAGGGC TACCTCGAGC CCGAGCAGGC CCAGGACTAC TTCGCCGAAG    11580

CGGAGAAGAT CTCCATCGTC CAGCAGTTCG CCCAGAAGAT CCCGATGGGC ACGACCGGCC    11640

AGAAGATCCC GCACTGGACC GGCGACGTGA GTGCGTCGTG GATCGGTGAA GGCGACATGA    11700

AGCCCATCAC CAAGGGCAAC ATGACCTCGC AGACCATCGC CCCCCACAAG ATCGCGACGA    11760

TCTTCGTGGC CTCGGCGGAA ACCGTCCGTG CGAACCCGGC CAACTACCTG GCACCATGC    11820

GGACCAAGGT CGCGACCGCC TTCGCGATGG CGTTCGACAA CGCCGCGATC AACGGCACCG    11880

ACAGCCCGTT CCCGACCTTC CTAGCGCAGA CCACCAAGGA GGTCTCGCTG GTGGACCCGG    11940

ACGGCACCGG CTCAACGCC GACCTCACCG TCTACGACGC GGTCGCCGTC AACGCCCTGT    12000

CGCTGTTGGT CAATGCCGGC AAGAAGTGGA CCCACACTCT GCTGGACGAC ATCACCGAGC    12060

CGATCCTCAA CGGCGCGAAG GACAAGAGCG GTCGCCCGCT GTTCATCGAG TCGACCTACA    12120

CCGAGGAGAA CAGCCCGTTC CGCCTCGGTC GGATTGTGGC CCGTCCGACC ATCCTGAGCG    12180

ACCACGTCGC CTCGGGCACG GTCGTCGGCT ACCAGGGTGA CTTCCGCCAG CTCGTCTGGG    12240

GCCAGGTCGG CGGCCTGTCC TTCGACGTGA CGGATCAGGC GACTCTGAAC CTGGGCACCC    12300

CCCAGGCTCC GAACTTCGTC TCGCTGTGGC AGCACAACCT CGTCGCAGTC CGAGTCGAGG    12360

CCGAGTACGC CTTCCACTGC AACGACAAGG ACGCGTTCGT CAAGCTCACG AACGTGGACG    12420

CCACCGAAGC CTGATCCAGG CTTGACATCC ACCGGGAGGG GGCTCCTTCG GGAGCCCTCT    12480

CCTGATGTGG AGCAGGAAGG ACCACATGCG AATCCAGTCC ACCCTCAACG GCGGTTTCGC    12540

CGAGGTTTCC GAGGAGTTCG CCAAGCAGTT GATCGCCACT GGCGGCTGGA AGGTGCCCCG    12600
```

```
GAAACCGCGC AACACCAAGA CCAAGACCGC TCCTGAGGAG CCCAAGAACG AGGAGTAACC    12660

CGTGGCCTAC GCGACCGCCG AAGACGTTGT GACGTTGTGG GCCAAGGAGC CTGAGCCCGA    12720

AGTGATGGCG CTGATCGAGC GCCGGCTCCA GCAGATCGAG CGCATGATCA AGCGCCGGAT    12780

CCCCGACCTG GACGTGAAAG CCGCTGCGTC GGCGACGTTC CGGGCCGATC TGATCGACAT    12840

CGAAGCTGAT GCTGTTCTGC GCCTCGTGCG TAACCCGGAG GGCTACCTCT CGGAGACCGA    12900

CGGTGCGTAC ACCTATCAGC TCCAGGCCGA CCTGTCGCAA GGCAAGCTCA CCATCCTCGA    12960

TGAGGAGTGG GAGATCCTCG GGGTCAACTC CCAGAAGCGC ATGGCGGTCA TCGTCCCGAA    13020

CGTGGTGATG CCGACGTGAG CGCGAGCGAC CGACACCGCG CCCCGATTGT CTATCCGCCT    13080

GGCACTCAGG CGGTTACGCC GGATCGGGTC AACGCGTTTG ACTGCGATCA CGAAGCTGAT    13140

CCTCCGGTGT GCCGGTGCGT CCACGACTGG CGCATCGAGT GGGGAAACGT CAAGAAGGCC    13200

ACCGCCAGAT CACGGTCGGC GGTGCTCTGA TGAGCCTCCT CGACACCGGT GCCCGGTACC    13260

AGACCTGCAT CGTCTACCCC GAAGAGATGG TCATCGACTC CGATGGCAAC AAGCGGACCA    13320

GGCCGTCGAA TACCGGCATC CCGGCCATCG CACGGTTCCA GGTAGCCAAC CAGTCTGGTA    13380

CGTCGGCACG ACGTGCTGAG CAGGACAACG AGGGGTTCGA GACCGAGAAG GTCTACCGGA    13440

TGCGGTTTCC CCGCTCGTTC ACCAAGGAGC ACGGCATCCT CGGGGCCCAG TCCCAGATCG    13500

AGTGGCGAGA CCAGCGGTGG GCGCTCTTCG GAGACGCCAC CGTCTACGAC TCATCCCCTG    13560

CGTTGGCGCG GGTCGACTAC ACGATCAAGA GGTACTGATG GCCAAGGTCT ACGCGAACGC    13620

GAACAAGGTC GCGGCCCGGT ACGTCGAGAC GAGGGACGCC GTCCGAGACG AGCGGAACAA    13680

GGTCACCCGT CGAGCCAAAG CCAATCTGGC GCGGCAGAAC TCGACCACCC GCATCACCGA    13740

CGAGGGCTAC TTCCCGGCCA CCATCACCGA GCAAGACGGC GATGTCGACT TCCACACGAT    13800

CCTCAACGCG CCCAACGCGT TGGCGCTTGA GTTCGGCCAC GCGCCGTCTG GCTTCTTCGC    13860

TGGCACCGAC ACGAAACCAC CGGAGGCCAC TTACATCCTC ACCCGAGCCG CCATCGGCGG    13920

CACCGTCTCA TAAGGAGGTC ACATGGCGCG AATGCCTCGC GTCCAGGCAG TAGCGGCCCC    13980

GATCCTCCGG TCAGACCCCC GACTGGAGGG AGTGACGGTC ACGACATGGG TTCCAGACGT    14040

GGACTTCCGA GAGTTCCCGA TGATCAACCT CCGCCGCATA GGCGGGACGA GGAACCCCAA    14100

CGCACCGACG CTGCACACGC TGCCGGTGGT CGAAATGACC GCCTACACCA GAGACGGTCT    14160

CATCGAGACT GAGGAGCTGT ACGAGACCGC GCTAGAGGTT CTCTACGACG CGGTGGAGAA    14220

CGGAACACAA ACTCCCGCAG GGTATTTGAC CTCCATCTTC GAGACGATGG GCGCCACTCA    14280

GTTCAGCTCC CTCTACCAGG ACTCCTGGCG CATCCAGGGT CTGATCAGGC TCGGCGTCCG    14340

CAGACCGAGA ACCACCCTCT AACCGAAAGG TAAAGCCACA TGGCTGAAAA CGACGACGCA    14400

GTGTTGACTG CGGCGGTCGG CTACGTGTAC GTCGGTGCTG CAGGCACCGC TGCTCCTACG    14460

CCGGCCTTGC TCAAGACCAT CGACCTCAGC AAGCCCGAGA CCTGGACCGG TGCTACCGGT    14520

TGGACGAGCG TCGGCCACAC CAGCCGAGGC ACGCTCCCTG AGTTCGGCTT CGAAGGCGGC    14580

GAGTCCGAGG TCAAGGGCTC CTGGCAGAAG AAGAAGCTCC GCGAGATCAC CACCGAGGAT    14640

CCCATCGACT ACGTCACGGT CCTACTGCAC CAGTTCGATG AGCAGTCGCT GGGTCTGTAC    14700

TACGCCCCA ACGCCTCTGA GACTCCTGGT GTGTTCGGTG TGAAGACCGG CCAGACCAAC    14760

GAGAAGGCCG TGCTGGTCGT GATCGAAGAC GGCGACATGC GCCTGGGGCA TCACGCCCAC    14820

AAGGCTGGAG TTCGCCGCGA CGACGCGATT GAGCTGCCCA TCGATGACCT GGCTGCGCTG    14880

CCCGTCCGGT TCACCTACCT GGACCACGAA GACGAGCTGC CGTTCTCCTG GATCAACGAA    14940

GACCTCTTCA ACGTGCCCGA GGTTCCCGAG GGCTGATCCC AACTTGACAG CCACCCGGCT    15000
```

```
GTCTACCCCG GAGGGGGAGG TTTCCTTGGC GGGCCTGGCC TCCCCCTCCT CCCGCCACTC   15060

ACAGACCCGC CGACACTGAA AGGTTCGCCA TGACAAACGT ATTCACCATC GACGCATTCC   15120

GCGAAGAGGT CAAGAAGAAG TACGCTCCGG TCCTCATCGG CCTGTCCGAC GATGTGACCG   15180

TCGAGCTGAA GCCGCTGCTG AAGCTGGGCC AGAAGGCCCG CGAAGCGGTG GTCGAGGTGT   15240

TCAAGGAGTT CGCGGACATC CCCGACCTCG AAGAGGACGA CGACGACGAG TTGGTCGATG   15300

AGTACTCGCT CCAGGTCTGC GACATCATCG CCAAGGCGTT CCGGCTGATC GCCACGAAGC   15360

CCAAGAAGCT GATCGCCGCC TTGGACGAGG AGCCGGATCC CCGTATCCGC GCAGAGCTGT   15420

ATGCAGCGGT ACTCAACACC TGGAAGCGAG AGACGCAACT GGGGGAAGCC GCGCCCTCGC   15480

CGAGCTGATC GACAAGTTCG GCGGGGCGAT CCTCGCAGAC CTGCTCCAGT ACTACCGGGT   15540

AGACCTGCGC GACCTGTTCC GCGACGAGGA TCCGCTTTCG CCGAGATTCG TTCTGTCCCT   15600

GGTGCTCTGC CTTCCCAAAG ACGGCGCGTT CTACGCAGAA CGTCGTGGTG GGCAGCAGTA   15660

CCGGGGCTGG ACCGAGGACC GCTACGCGCT CGCGGACATC TACGACGCCA TCCAGGCGGG   15720

CAACCACATC CTGCTGCTGG CGAATCGTGA TCCGAAGAAG CCAAAGCCCA AGGCACCCAA   15780

GTCATACCCG CGTCCCGACG ACCTAGAGAA GACCACACCG AAGCCGGGTT CGTTCGCCGC   15840

AATGGTCGTG CGAGCGAAGA AGGCGGCTCG AGAGAGAAGG GAAAGGGAGG AGGAGAGTGC   15900

CGAATAGTGC TGGCGTAGAA GTCGCCCGGA TCTCGGTCAA GGTCAGCCCG AACACCAAGG   15960

AGTTCCGCCG GGAACTCAAG ACCGAACTCG AGAAGATCGA GCGGGAGCTT AAGGGCGATG   16020

TCGAGATCAA CGGTCATCTC GATGCGGCCC AGGCCAAGGC CGACTTCAAG CGCATGATGA   16080

TGCAGCTCAA GACCGAAGCT GCCAAGGGCG TTCACGTCCC GGTCGACGTA ACCGTCGACA   16140

AGAAGAGCAA GAAGGGAGGT CTCCTCGGAG GTCTCCTCGG CGGCAGCCGG GGGCTCGGAG   16200

ATCTAGGCGA TGACGCCGAG AAGGCGTCGT CTCAAGTACA ACACCTTGGC AAGTCGTTCC   16260

TGGGCCTCAC ACGAGCCGCC TGGATAGGCG TAGGCATCGT CGCCGTAGCA GCTCCGCTGG   16320

TCGGCATCGT GGCCGGTCTG CTGGCCGGTC TGCCGTCGCT GCTGTCTGCG TTCGGAGCCG   16380

GCGCTGGCGT AGTCGCGCTC GGCATGGACG GCATCAAGGC AGCCGCCTCG ACGCTGGCCC   16440

CGACGCTGGA GACGGTCAAG GCCGCTGTCT CCTCGACGTT CCAGCAGGGA CTCACCCCGG   16500

TGTTCCAGCA GCTCGGCCCG ATGCTGACCG CGATCACCCC CAACCTGCAG AACGTGGCCT   16560

CGGGCCTCGT GAACATGGCC GGGTCGATCA CCGACGTGAT CACCCAGGCT CCTGGTCTGC   16620

AGCAGATCCA GAACATCCTC ACCAAGACCG GAGAGTTCTT CACGGGCCTC GGCCCTGTGC   16680

TCGCTACCGG CACGCAGGCG TTCCTGACGC TGTCCAACGC CGGCGCGAAC TCGTTCGGCA   16740

CGCTCCTGGC TCCCCTGCAG GAGTTCACCA ACGGCTTCAA CGACATGGTC AACCGAGTCA   16800

CGTCCAACGG CGTGTTCGAG GGTGCCATGC AAGGGCTTTC GCAGACGCTG GGCAGCGTCC   16860

TCAACCTGTT CAACCGGCTC ATGGAGTCCG GTCTGCAGGC GATGGGACAG CTCGGCGGTC   16920

CGCTGTCGAC GTTCATCAAC GGGTTCGGAG ATCTCTTCGT CTCGCTGATG CCGGCGCTGA   16980

CTTCGGTCTC TGGTCTGATC GGCAACGTCC TCGGACGCT  GGGCACACAG CTCGCTCCCA   17040

TCGTCACGGC GCTCACGCCG GCCTTCCAGA CGCTGGCGAG CACGCTCGGC ACGATGCTCA   17100

CCGGAGCCCT CCAAGCTCTG GGTCCGATCC TGACTCAGGT CGCTACGTTG ATCGGCACGA   17160

CGCTGAACAC GGCGCTGCAG GCTCTCCAGC CGATGCTGCC GTCGCTCATG CAGAGCTTCC   17220

AGCAGATCTC CGACGTACTG GTGACCAGTC TGGCCCCGCA CATCCCGGCG CTGGCGACGG   17280

CCCTCGGCCA GGTCGCAGGC GCGGTGCTGC AGCTCGCTCC GACGATCATC TCGACGTTGG   17340

TTCCGGCGTT CGTTCAGTTG GTCCCAAAGG TCGCTGAGCT AGTTCCGACC ATCGTCAACC   17400
```

```
TGGTCCAGTC GTTCGCCAAC CTGATGCCGG TGGTTCTGCC CCTGGCGCAG GCTCTGGTCA   17460

GCGTTGCTGG CGCGGTGATT CAGGTGGGTG TCTCCATCGG CGGCGCGCTC ATCGGCGCGC   17520

TGGCGAACCT CACGGAGATC ATCTCCAACG TCATCAAGAA GGTGTCCGAG TGGGTCAGCA   17580

GCTTCTCCAG CGGAGCCCAG CAGATCGCTG CGAAGGCAGC GGAACTGCCG GGATGATCC    17640

AGTCGGCTCT CGCCAACCTG ATGGCCATCG GCCTGCAGGC CGGTAAGGAT CTCGTCCAGG   17700

GCCTGATCAA CGGCATCGGC GGGATGGTCA GCGCAGCGGT CAACAAGGCC AAGGAGCTGG   17760

CGTCCAGCGT GGCTGGTGCA GTGAAGGGCT TCCTGGGCAT CGAGTCCCCG TCGAAGTTGT   17820

TCACCGAGTA CGGCCAGTTC ACCGCCGAGG GATTCGGCAA CGGCATGGAG GCAGGGTTCA   17880

AGCCCGTCAT CGAACGGGCC AAGGATCTCG CGGCTGAGCT GTCCAGGGCG ATGGAGTCGG   17940

GCACCGACCC CTCCGGGATT CTCGCTGGGC TGGATCAGAA TGAGCTGAAG CAGATGCTGG   18000

CGGCTCTCGA AGAGGAGCGC AAGCGACTCA AGGTCGAGAA GAACGGTATC CCCAAGGGAG   18060

ACAAGGCAGG CCGAGAGGCG CTGCAGAACC AGCTCGACCA GATCCAGGCG CAGAAGGACA   18120

TCCTGTCCTA CCAGCGTGAC CGCATCAAGA ACGAGTCTGA GTACGGCGAC ATGGCCGGCG   18180

AAGACCCGTT GGTGAAGGCA GCCTCCGGGC TGATGAGCGC ACCGGTCGAC TTCGCGAAAG   18240

CGACTGGCAA GCAGTTCCTT TCGGACATCG GCATCAGCGG AGATGGGTTC ATCTCGAAGG   18300

CCATCACCGA GGGCATCCAG TACATCTTCC AGATCGGCTC TGTCGATGAG GCGCTGTCGA   18360

TCAAGGACCG CGAGGAGTCG AAGAACGCGC TGTCCGTCGT TGGCCGCTGA CTTGACATCC   18420

ACCAGGAGGT AAGCATTGAT CACCGACACC ATCGTTGAAC TCGAGGGTGT CAATGGTGAG   18480

CGTTTCAACT TGACGACCGG TGACCAGGGT GTGTACCTGG CCACAGACGT GGAGGGTTGT   18540

TTCTACGACC CTCCCGTCAA GGTCGTTGTT GAAGAGCCGG GGAACTACCC CGGCGCTCGC   18600

TACTTGTCCC ACCGAGCCCT GAAGCGAGAC ATCGTCTTTG GGGTCGTCAT CCTCAACGAC   18660

GCGAAGCAGG GGCCGCGCTC CTGGCTGTCG CGAGACTCCG AGTGGCGCAA GGCGTGGGCG   18720

TTCAACCGCA CCTGCAAGCT CTACGTCACC ACCCCGGACT CCGGTACCCG CTACCTGAAG   18780

CTGGCGCTGT TCGAGTCCCC CACCGTCAAG ATGGACACCG ACCCAAGAGG TAAACCCCTT   18840

GAGGTCACGG TGATGTCGTG CATCGCGTAC GACCCGTTCT GGTACGAGGA CGACAAGGTC   18900

TTCTCGGCCA AGACCAAGAC CGACACCCGG TTCGACCCGT CGTTCTGGAC GCCGCCGTGG   18960

CCGTGGGAGG AACTGCCCAA GGAGACGCTG CGGATCAAGG TCGGCCGCGA GCAGGGTGGG   19020

CTAAACCCCA CCGACCAGTA CATCTTCCCG AAGTGGACCG TTCCCGGCTC CACCGAGAAG   19080

GTGCCGAACT TCCCCTGGCC GTTCCCCCCG AACGTCCCGA TCCCGTGGGA CACAGCACCG   19140

TTCACTCAGT TCGTCATCCC GGACTACTCG TTCGAGGATG AGGAGTTCCG CAACCGCCGG   19200

CTCAAGACGC CGGGGTTGAT CTACGGCGAG AACTGCGTCA TCGACACCGA CCGGCGCGAG   19260

GAGCAGATCG CTTCCGAGTC GGGCTCCCCG GTGTGGGCTC GGATGAACGG TGTCCGGTTC   19320

CGCAACTCGA TCCCGCCCTA CACCGAAGAG GCTGAGTTCG TCATAGACGC ATCGGGATGC   19380

GCTCCGGGAC AGGTAGTTAC CCTCCGGCTC ACGAGGCCGT GGTCGCGCTG CTGGGGGCTA   19440

GAGTGAGTGG TCTGACGAGC GTTCGTGAGG CCGAAGATCT CTGGCAGAAG ATCCAATTGC   19500

GGCGCTGCAA GCGCGAGCAG GAACGGCTCA AGCATCCCGA CGTAGAGCTG CGCGATGGCG   19560

ACTTCCGCCT GCGCGGCCTG GTCGCTGGCG AGCGGGTGCT CGAGTGGGAG TTCATCGAGA   19620

ACGAGACTGG CACCTGCACC TTGCAGCTCT CACTGAGCCA TTACCTGGCG AAGTGGGTGA   19680

TGGACCACCG GGGTCGAGCA AAGCGCAACG TCATCATCAA CATCGAGAAG CAAGGCGCTC   19740

GATGGACCGG GATGATGGAC CACTACCGGG TCATCAAGAC CGACGCAGGG GACGCCTACA   19800
```

```
TCGAGATCGT GTTTTTGCAC GACTTCGAGC AGACCAAGCA TATCCGGGTA TGGTGCAACC   19860
CGTTCCTACG CCCCGAGCTG CAGTTCCCCA AGGTGTGGAT CATCTTCGGG CCGGCCAAGT   19920
GGTGTTTGCT GGTGACACTG TTCGTCAACC TGCTCAGGCT CGAGACGAGC TTGTGGACGC   19980
TGCCTGATGA CCCCACGGAC ATCAACGAGT GGATGGGTCC GAGCTTCAAC CCAGCAAATT   20040
GGCGGAACAT CGTCAAGCCG TTCCCGTTCC TGGCCGACAA CTCACCGGTC ACGATGGTGT   20100
TCAGCCGGTT CGGGACGTTC TACGACACCG CCAAGAAGAT CCTCGAAGAC CATCAGCTCA   20160
CGCTGACGTG TCGTCGGTAC ATCAAGGACC GCGACCCGCA TCCGTTCGAA GATCTCAAGG   20220
GGCTCTGGGG AATTGATCCT GTCGAAGACC TGCTGCAGAA GATCCCGCTC CGGGACGGCT   20280
GCGTGGTCTG GGACATCGAG GACAACTCAG GTTGGGGCAC TCAGACCGCG TTCGGCGGTT   20340
CGTGGCTGAC CGGGTTCGTC CGAGGGATGG TCCAACTGGC CGGCGACGGC CAGGTCGAGG   20400
GCGTCGATGT GTTCACCGGG GACTACACGT TCCCAGGCGA GTACTACTCC CCCTGGTTCA   20460
TGGGCACCAG CCCGATAGCA CCCCACGTCG TGTTCGAAGA AGGACCGCTG ACCGGGATCA   20520
AGTCGTCGGA GTTCTCGTAC TACGAGGCCA CCGACACCAG CTTCCTGGCT GGTGGACAGA   20580
GCGCACCTGG CATCAACGAG GGCATCTCGG CCCTGGTGAA CATCGGTGGC GACCTGCTGA   20640
CCTCGTTCAT CAACAGCCAG CTCGCCGCGC TCGGCGCGGT CGGTGGAGCG ATTGACCTCC   20700
CGCCTCTGGG CGGTCTGCTC GATGCGGTGT TGCAGCCTCT GTACTCCGAT GTGTTCGGCG   20760
CGTTCATGGA AGTTCCGACT CTGCGTGCGA TGGGCATCTC GCTCCCGATC TCCGGGCTCG   20820
AGGACATCGT CACCGGACTG GGCGACTTCC ACTACTTCGA GAACATGGCC GACGGGGCGA   20880
TGAAGGCGTT CACGCTGTCA GCGTTCGCAG CCATCGCATC GCAGATCCAC AAGACGAGGG   20940
CTCGAACGAC CCACACCCTC AAGGTGTCTG ACGCCGCTCC GTACATCTTC GCGCCAAAGC   21000
CCTACGGGCA CTGCTGGATC GGAGATCGCG TCGGCACGTC GGTCCTCGGC TACCCGGTCG   21060
AGCACCAGTT GTTCGTGGAG CGCATCCGCA AGGTGAAGTA CCGCATCGAC AAAGACGGCA   21120
TGAAGCCGTT GGAGATCGAG ATCGGTTACC GCGAACCGAA GAACCCAGCA CTACACATCC   21180
TCGAAGAGAT CAAGCGCGTC AACGGCGCTC TTGGCACTGC GGGGATTCTC TAAACCGAAA   21240
GGCACGCCGC ATGATTCCCT CACAAGAGTC TCACAATCCG AACGACCCGC GACAGCACGT   21300
CATGTGGGCG CTACGCAATC TCCCGATGAT TGCTGGCGTC GGGGCGATCA CGCATCCGGG   21360
TTACCTGGCG GATTGGTCAG AGCACTTGTG GAAGTGCGGC TTTCGGCACG TCGACTGGCT   21420
CCGGGAGCTG GCTGATGAGG ACGGCAACAT CCACGTCAGT CAGCTTCCTG ACCAGGAGAT   21480
CAAGTTTCAG CAGCCCTTCC GGGGCCAGCG AAGCGACTAC AACAACGCAG CTCGATGGGT   21540
CGGCAAAGAC GATCCTGACC CAGAGCCCGT GCGTATTCCA GACATTCGCA AGCTCACAGA   21600
CCAGGAGAAC AGAGCGATGA TCGCGCAGTA CGAACGAGAC GGTTGGATCA AGGATGGATC   21660
CCCCGGCCCA GCGATAGCCG AGGTCGTGGA GTGACCCCGT TCAACCCAGA CTCCATAGGC   21720
GACTACGTGA CACTGCTCGG CGTTGCGTTC CTGACCTTCT CGGTTCCCGC ATGGTTCACC   21780
GGACGAGCAC GCAAGCACAG CAGTGACATC GGCGAAATCA AGAACAGGT ATGTAACACC    21840
CACGACACGA ACCTGCGCGA TGACCTCGAC AGCGTCAAGG CAGACATCAG CGACTTGAAA   21900
GAGATTGTGT TGCAAGGGTT CCACCAGGTG AACGAGTCGA TCAACCTCGA GCGCCGTGAG   21960
CGGATCGAAG GAGACCGCCG AAAGGAGGTT GCGTGACCTA CCCCACCAAC CCACTAGAGG   22020
CCATCGGCGC TGACGGCGCA TTCGAGATCG GTGGGGCGA CTGGAGCTTC GGCCAGGACT    22080
ACACCGAACA GGCCATCCGG GCTCTGTTCA CGATGCCAGC GGTCACGATG GAGAACGCTC   22140
TCGGCCTGCT CGAAGAGCAC CTGCTGAAGC TGCCTCTGGA GGCGCTGCAG GGCTTCAAAG   22200
```

```
ACATGATCCC GGACTGGGTC GAAGGAGCAT TCGACACGGT CACCGGCGCT GTGCAGGCGA    22260
TCATGAACGC GCTCCAAGAC GGCCCGCTGT TCCTGAAGTT CGCCGAGTTC CAGCTCTTCC    22320
TGCAGCGTCT GCTGAACAAC CCGGCCGAGG TCATCGGCGA GATCCCCCAG ACGTTGATCG    22380
ACGGCCTACA GGACGCGCTC AACACCGTCA ACAACACCAT CCAGACCATC GTGGACATGC    22440
TCCTGCAGGC GCTGGGCATC ACCCCGGAGG GGGAGCTGAT CGACCGGATC TTCGACCTGA    22500
GCGATGAGAT GGAGTGGCTG CAGACCGCAG CCTCGAATGC AGCTACCGGC ATCCAGGACA    22560
CCTGGAACAA GTTCTGGGGA GCCCTCACCG GGCGCGTCCC AGACCAGGAC CAGACCGTCG    22620
CTGAGCCCGC CGAGCGTATC GGCGAGCTGG CCGGCACCAC GTCTGCTAAC TCGTCTGCCA    22680
TCGCGGAGCT GCAGCGTCGA CTGGACAACC AGCAGAACGC TGGCGGCGTG GCCGGCGGTG    22740
ACGACTTCGA GCGACTGAAC ATATCCGGTT GGGACATCAG GTATTCCAAC GGATCCAGCG    22800
GCCGAGGGTA CTACCGTGCC GACGGCCACC AACTGGTCTG GATGGACGAA GGCAACCAGC    22860
AGAACACCGC GACGTTCGTC CGCACCAACC CCGCAGACGA GAAGACAGCC ACCGACTACC    22920
AGAAGATGAC GTTGGTCGTC GGGACTATCT CCGGTGAGGT ACAGACCGTG TTCCCGCCGC    22980
AGGGAGGTTC GCACACCCGG CTATGGGTCC GCGTCAACGA CAACGCTCCG ACCGTCGGCA    23040
TCACCGACGG CGTGTTCGTA GAGATCGGCG GCGTATCGAA GGCCCAGATC GGCTACCGCC    23100
GCAACGGCAA TGACACGTTC GTCGGATCTA TGGTCGACTG CACCTGGGGT GCTGGATCGA    23160
TCTTCGCTCT GACCGCCGGC ACGGCCAACG GTGCTGAGAA GTTCGAGGTC TCAAGAACG     23220
GCCCCGTGCT GGCCACATGG TCGGACGACG GCGTCGTCTC CGCGATGGGT GCGAACTACC    23280
GCCGCTGGGG CTGGGAAGGC CAGGCTCGTA ACCGCAACCT CGGCCAGGGC ACTCCGAACT    23340
CGGTCACCCG AGTGACGATC ACCGACAACG ATCCTACCGG CGCAGGCGGT GGAGCTGTCA    23400
ACGTCGGAGG AGATGTCGTA GGTGTACTCC CCATAGAGAA CGGAGGCACC GGAGCTTCGA    23460
CAGCTTCGGC AGCCCGTACC GCTCTCGGAA TCGATGACCT GGTCGAAGAT ATGTCCGACG    23520
TAGTTCGTGG ATCCGTCGAA GGACTCCCGT TGATACCGAA GATCTGGGTA GGAACAGAAG    23580
CTCAGTACAC GGCTCTCGCC ACCAAGGATC AGTCCACGCT ATACTTCAGG ACCGCTTAAT    23640
GACTGGTATC TCGTTGGGTG TCAACGACAT CCGCAACCTC TCGATATTCT TAGGCGTCAG    23700
CAACAAGATA TTGAAGGTCA GTCTAGGCAC AGAAAAGGTC TGGCCTGCGT TCACCCCGGT    23760
GCTGACCACG TTCGCCACGG TCGGCACGTA CACCTACAAC ATCCCCGACG GGCCAAGTT    23820
CATCGACGTC ATCCTCCTCG GAGGAGGCGG CGGGGGTAAA GGCATGGCCC TGGCTGACGG    23880
CTGGGGCAGA GGTGGAGACG CCGGAAGCTG GGCTATCGTC ACTCTCGAAC GCGGGGTACA    23940
CATCCCGTTG TCGACCAAGA CGATCACCGG GCTCGTCGGA GCTGGAGGCG CAGCGGGAGC    24000
TGGCTCTGTA TTCTCAGGCA AGGCCGGAGG CCCTGGAGGA AACACCACGG CGTCCGCTGT    24060
CGGATGGTCA GGTTTGACCG CAACCGGCGG TCCCGGAGGC TCTGTGATCG ACATCCTCAG    24120
CGTCGCCGGA AAGTCGCCTG GAGATCGGAC CTACAACGAC CAGCTCTACA TAGGCGGCGC    24180
ACAACAGAAC TCAGCTGGCG GGAACGGCAA TGCTCCTGGC GGCGGCGGGG CTGGTGCCCA    24240
GGTCTCCGCA CAGAGCGGCG GTGCTGGCGC TCGCGGCCAG GCGTGGTTCT TCGCGTACTG    24300
ACAAGAAACC CCCCTCTTTA GGACTCAGTG TCCTTGGGAG GGGGGCTTTT TGCGTTTCAG    24360
GAGGTCTTGG CCAGCTTGGA CATCGCCTCA GCGATAGCCT CGTCGCGGGC CTCAGACGCC    24420
ATCTGGTACT TCATCGCCAT CCTAGGAGTC GTGTGACCGA GACGGGCCAT CAGCTCCTTG    24480
GTCGTCGCAC CTGCCTGAGC GGCGAACGTA GCGCCGACAG CGCGGAGGTC GTGGATGCGG    24540
AGTTCCGGCC GACCGATCTT GGCGTAGCCA CGCTTCAGCG ACTTGGTGAA CGCGGACTTC    24600
```

```
GACAGCCGGT TGCCCTGCGT CGTGGTCACC AGGAATGCCT CGGGGCCCTT GTTCATCTTC    24660

GTACGGTCCT TCATGTGCGC TCGGATCATC TCCGCGACGT GAGGCGGAAC CGTCACAGGA    24720

CGCTTCGACC GGACGGTCTT GGCGTTGCCA ACGACGATCT TGTTCCCCAC GCGGGAAGCG    24780

CCACGGCGCA CCCGGAGCTT CATCGTCATG CCGTCGTCCA CGATGTCCTT GCGGCGAAGC    24840

TCGATCAGCT CTCCGAACCG GAGGCTCGTC CACGCCAGGA TGTATGCCGC GATCCGGTAG    24900

TGCTCGAAGA TCTCAGCGGC GACGATGTCC AGCTCCTCAG GCGTCAGCGC CTCTACGTCG    24960

CGCTCATCGG CTGCCTTCTG CTCGATCCGG CACGGGTTCT CTGCGATCAG CTTGTCCTCG    25020

ACCGCTGTGT TCATCACCGC CCGGAGGACG TTGTAGGCAT GCCGGCGGGC AGTCGGGTGC    25080

TTCCTACCCA TCCCGGCCCA CCACGCACGC ACCAGAGCTG GCGTCATCTC TGTGACCGCC    25140

ACTTCACCTA GCACCGGGTA GATGCGGCGC TCCGCGTGCC CGCTGTACAG ATCCCTGGTG    25200

CCGTCTGCGA GGTCGCGCTC CACGAGCCAC TTCCGGGTGT ACTCCTCCAG CGTGATGGCG    25260

CTGGCGGCTG CCTTCTTCGC CCGGTCCTGT GGAGGGGTCC AGGTCTCCAT CTCGATGAGC    25320

CGCTTCTCGC CCGCGAGCCA GGCTTCGGCG TCCATCTTGT TGTCGTAGGT CTGCAGCGCG    25380

TAGTACCTCA CACCGTCCTG CGGGTTGACG TATGAGGCTT GGATCCTCCC GCTGCGCTGA    25440

GTCTTCAGCG ATCCCCATCC GCGACGTGCC AACTAGGTCT CCTCTCGTCG TGAACAAGGC    25500

TACCGGGTTG CAACTCCTGT GCAACTCTCA GGCTTCAACG CGCTTCTACG ACCTGCAATT    25560

TCTTTCCACT TAGAGGATGC AGCCGAGAGG GGGTAAAAAC CTATCTTGAC CGGCCCATAT    25620

GTGGTCGGCA GACACCCATT CTTCCAAACT AGCTACGCGG GTTCGATTCC CGTCGCCCGC    25680

TCCGCTGGTC AGAGGGTGTT TTCGCCCTCT GGCCATTTTT CTTTCCAGGG GTCTGCAACT    25740

CTTGTGCGAC TCTTCTGACC TGGGCATACG CGGTTGCAAC GCATCCCTGA TCTGGCTACT    25800

TTCGATGCTG ACAAACGAAT AGAGCCCCCC GCCTGCGCGA ACAGACGAGG GGCATTCACA    25860

CCAGATTGGA GCTGGTGCAG TGAAGAGAAT AGACCGGGAC AAGGTTGCAC CGGGAGTTGC    25920

AGCGGTCGGA ACCCTCGCCG TCGGCGGGCT GGCGTTCGCC CTGTCGTTCA CGGCTCTCAG    25980

CGAGCTGGCT GCGGCCAACG GGGTGGCCCA AGCAGAGATG GTGCCCTTGG TGGTCGACGG    26040

CCTGACGCTC GTCGCCACGG TCGCCACAGT GGCCCTCAAG CAGAACAGTT GGTACGCGTG    26100

GTCGCTGCTG ATCCTGTCCA CCGTCGTATC GGTGGCCGGC AACGTGGCAC ACGCCTACCC    26160

CCACGGCATC ATCGCGATGG TGATCGCTGC GATCCCTCCG CTCTGGCTAC TGGCGTCGAC    26220

CCACCTAACC GTGATGCTGG CGAAGCAGCA CTCGGAGCAC GCCGAAGTAC CTGTCTCGCG    26280

GCCAGAACCC GCGCCTCGGG GCCTGGAGCC CGCTGCCGCT TGACTGCGCC CGACCGGGAC    26340

AGAAATACAT AGAGAACCTA TGGATGTAGG AGGCACAAAA AAATACCCCC CGAGCCAGCC    26400

CGAAGGCCAG CCCAGGGGGC ATGGTTCTGC TTCAGTAGAC CTTGCGAGTC CGACCCGAGT    26460

TGATCATCGC CATGATGACC CAGACGGGCA ACCACATTCC GCAGGTGATG AGCGAAAGCA    26520

ACAGGTGCAT CGCGTGGTTC GTCCTGACAG GCATGACAGT GGGCTGCGGC ATCGGAGGAG    26580

GCGCGACCGG GTACGGCGAG CCCGCGTACC ACTGAGGTCG ATCTTGTTGG GGCGGATACT    26640

GATTGGTCAT CCCGACAGCC TACTTGCCGA TGGGTCGCAT CAGCTCCTCG ACCGACTCGC    26700

GCTCCACGCG GATCAGCCGG GGACCGAGCC GAACGGCCTT GAGCCGGCCG TCGGCGATGT    26760

AGTTGCGGAC GGTCTTGGTG CTGACACCGA GGTAGTCAGC GGTCTCCTGG ATGGATGCTC    26820

TCGGGGGCAT CAGCGCGGTC CTCCGTGCTT CATCGGTTGT CTCCCGAACC CTGGATCACG    26880

CCACGATCCT TGCGGCTCTG GAGCTTGTTG AGGTTCCTCT GGGTGACGGT GCTCAACCAG    26940

ACATCGAGCT GGTTGGCTAG CTGGGCGACG TACCACATCA CGTCTCCGAG TTCCGCCTGG    27000
```

```
AGGTCGTCTC GGTTCTCCTG GGTGATGACA CCGTCTTTAT CCCGGAGGAT TTTCTTGACC   27060

TTGTTGGCGA TCTCGCCGGC TTCGCCTACG AGACCCATCG TCACGTAGGA GAGACCCTCG   27120

ATGCTGTCGC AGTCGCCTGC ACCGGGGTAG ATCGCTGTGT CGCTCGCGGC GATCTGGTAG   27180

ATGTCGACGT GCATCAGATC ATCACCGGGA ACAACTGGCC ACCGGGCATC TGGATGAACA   27240

CCGGGACGCT GGGGGTGTAG TCCGACGAAC CCGTGCCGCC CTCACAGGCG GACAGGCTCA   27300

GGGTGGCGGC AAGGCCGATG ATGGCTGCTG CGATGGTCTT CTTCATCTGT TGCTCCAGTA   27360

GCTAAGTTCG GACTCCAGTT CGCGGATACG CTCCTGTAGC CCTTGGTTTT CCAGGTACGC   27420

CTCGGCGAGG TTGGCCTCGG CGCGGTCACG GGCCTCGTCC TTCGACGTGG CCTCATCGAT   27480

TGCCTCGTGT AGCCGGCGGA TCAGATCTGG GATGGCACCG TGCAGACCGC ATATGAAGTC   27540

GGCGTCTGCC TCGGAGAGGT GGGACGCCAC CAGATCCTTG TCCTGGGTCT CCTGGTTGAC   27600

CGCCCAGATG ACGTGATCCT CTAGCCCGTG GTCGGTCTCG CAGATAGAAG GCGGTTCTAC   27660

CTCCTCTGGC ATCCAGTAAG TCTTCTCAGC CCCGGTGGAC TTCGCCCACT GCTGGTAGAG   27720

GATGTCGAAG AACTCGTGGT CCTGTTCGTC GGCGGTAATC ACAGATCGTC CTCTTCATCC   27780

CATTCGTCGT AGTAACACGT ACAGCCGCAG CAGGTGCAGC AGCCGCACTC GTAGGTGCCG   27840

TAGTCGTAGT CATCCCAGTC GTCTTCGTCC ATCTAGCTGT ACTCCTTCAT GATTCGGTCG   27900

AACGCACGCG TCTGCACGCG CATCTCCAGG TCGACCGTTC GCTTCAACCA CGCCCATTCG   27960

CCGTCGTGGT TGATCTCCCA CTGGCTCTTG AATGTCGCTG TCTCAACGAG GAACTCGACA   28020

GTCAACGTGT GCAGTCCGTT GTTGCTGGGC TGGAATCCGA TACCGTCCTC AGCGATGTAC   28080

CAGGGCAACT CCTGGCCGTC GAAGTAGACG GCCTTGTCGG TCACCAGTAC TTCAGGGAAG   28140

GTGTGCTCGG TCAACGGCGT CCCAGGTATG GGATGACGCT GGCCCGGAAC TCAAGGAACA   28200

CCATGTTGTC CGGGCAGTCC TCGGGGACGT TGTCGGGGCG TTCGGCGGTG TAGACGCCGA   28260

TCTCGTTGCC CTCCAGGGTT CCAAGCTCGT TGAGCTTGTA GATCGCCAGA CCCATCAGCT   28320

CTTCATCGAG ACCGTTCGGT GCTGGCAGTA CAACTTTGGC TTGTGGCATT AGCCCTCCCT   28380

CGGAATTACG TATGCGCTGA ACTCGACGGC CGTAATGCCG TCTGGCAGTT GGAATCCGAA   28440

CCGCTCTTCG AACTCCTCGT TGGTGATGGG GCCGTACTCG AAGGTTCCGG GCACTACCTC   28500

GCCCTCCCCC TCGATCAGGA GGTACGCACC GGCGGCGTAC ACCTCCTCGT CGTTCGGCCA   28560

TCCGACTACG GTCCCGAGGA CCGTGAACTT CCTCGGCTCC ATCAGGGCAC GTCCACTTCG   28620

TTGATGAGGA ACCGCATCGG AGGTGGAGTG AGCATTGCCT CGGCTATGGC GATGAGGGCG   28680

TTCAACTGAC CCTTCAGCAG CTTCTCCTCG TCGCCTGCGG GAAGGTGGCG CACTCGGCGC   28740

TCCATCTCCT TGGCGCGTTC CAGATATTCG GTGGCTGTCA AGTTGTCCTC CTTAGTAATC   28800

AGCGCCGTAG AGCGAACCCC ACGAACGCTT TCCGACCTCG GGGTCGGTGC CAACCAGCAC   28860

CGGACCCATC TGTTCTTGCA TCAGGTGGCC AATGTGTGCA GCGGCTCTCT CAGCCTCTGA   28920

GGCGGGCAGA GACGCGACGA TCTCGTCGTG GATAGGCAAC CGTAGGTACG GGGTGTATCC   28980

GGCCTCGTGG AGGCGAATCA GAGCCCGACA GGTCACGTCC CGCGACGACG ACTGGATCAT   29040

GTAGTTCAGC GCGGAGTATG TCCGCGAGCT GTCCACCGGC AGCCGCCGGC CCATCGCGTT   29100

GACGATGTAG CCGTTGCGGC CAGCTTCCAT CGCCAGCTTC TTGCTCAGCC GCTCCACACC   29160

GGGGTATGTC GCAGAGAACG CCTCATGAAC TCGCTTGGCC ACAGGGATCG AGATCCCCAC   29220

TGCCTCAGCG AGAGCCTTCG CCCCACCGCC GTAGACCTTC TGAAAGTTGG CGGTCTTCCC   29280

AACCTTTCGC GGCACCTGGG CTGCGTCAGC GGTCATCTGG TGGAGGTCCG CACCGTTCTC   29340

GAATGCCTCG ATCATGTTGC GGTCGCCCGA CAGCGCCGCC AGGACGCGAA GCTCCTGCGC   29400
```

```
CTGGTAGTCG ACTGAGGCCA TCACATCGCC TGGCTCAGCG ATGAAGCATC GCCGCACGAT      29460

CCAGTCCGAC GACGGCAGCG TCTGCGCCGG GATGCCGGTG ATCGACATGC GCGAGGTCCG      29520

CGCCTGCAGT GGGTTGATGA ACGTGTGGCA GCGGTCCTCA GAGTCCCTGG TGTCGATGAA      29580

CTTCTGGACC CAGGTCTTCC GCCACTTCCC CAGCTTCTTA GCCTCCTGAG CGATGGCGGC      29640

AAGCTCGTTG CCATCTTCGA CCAGCTTGTC GAGCAGAGCC GCGTTGACCT GGCGCTTGCC      29700

AGTCTCGGTG CGACCGGTGA TCTTGACGCC CATCTCCTCA AGCCCCTCGG CCAGATCCTC      29760

GGTCGAGTTG ACCTTCTCCA CGCCGTACTC GGTGAAAGCG ATTGCCTCCC AGACCTCCTG      29820

ATCGGCCAAC CACTTCTCGG CGAGCGACCG CGAGTACTCC ACATCGAGCA GGAAGCCCTG      29880

CCTGTCGATG TAGCTGCAGA TCTCACTGAT CTTGTGCTCG TACGGCACCA GCGACCGACT      29940

CACGTCGGGC ACCAACGGTG TCAGGCTCTT GCAGACCCTC GCGGTGAAGA TCGTGTCCAT      30000

CCCGGCGTAC AGCAGGTACT CCGGGTGGAA CAGGTCGATG GTCGACCAGA TCTTGGCCTT      30060

GGTCGTCTTG TGCTCGGCGG CTAGCTTGGC CATGAGCTTC TTGACGTTCT CGGCCTGGTC      30120

CTCGGAGATG AACTTCGCGA TCAGCTCTTC GAGCGAGTGC CCGAACCCGC CGGCCTCGAA      30180

GGGCCGGGGG TCCACCAGCT TCGCCAGGAT CTGCGTGTCA AGCACGCGGG GCCACAGACC      30240

CTCCATCTCG ATCCCGAAGC ACTGGTCGAG CACCTGGAGG TCGAAGGAGG CGTTCTGGAG      30300

CACCATGCGC TTGAGAGCGC CGATGGCGAT CCGCACGTCC TCGATGAACA CGTCTCCCAG      30360

CTCCACCGGC ACCACCCAGG CTTCGTCCTG AGTACCGAAC TGGACGAGGC GGCACTCGAA      30420

GGTGTCGCTG TAGATGTCCA GCCCGGTGGT CTCAGTGTCG ACGGCGAGGC AGTTCAGGTG      30480

AGCCCGGATG AAGTTGCGGA AGCCTTCCAG ATCCTCTGGG GTTTCAACGA CGTTGACGGT      30540

GACGAGGTCT CCCTGAACCT CATGCCGCAG CTCGATCAAA ATGCTCTCCT ACTGGAAGTA      30600

CTGAGGCGGA ATCCAGGTGG CTGAGGCCAT CTCCTTGATG GCCTGCTGCA TGGCCGCTTC      30660

GAACGGACAG TCCGGGTCGA TGTCCGGCTT GTAATGGGTG ACGATGATCC GGCTGTTGCC      30720

GCCGAAGTCG TGGCTGACCA AGCCCTTTGG GGGCAGCTTC TTCAGCGCCT TGATCAGTTC      30780

CTCAACCGTG GTCCCGGTAG GGGCCTTGCC GTCAGGCAAT GCCTCCCCTC CGTACGGCAC      30840

GTCCAATGGG ATCGTGTACC GCTCAACGTC TTTGATCTTC ATCGAGCCTC TTCCTCTTCG      30900

ACTACCTCGT CTACCCGGCG GAATAACTCC GCTAGTTCTG CGGGTAGCAA TACTGGGTAC      30960

TTCTCTCGGG CTTCCTGCAT CGCTACCGCG ATCCCAATCA GGGCAGCGAG CAGTTCATTG      31020

ACGGAGTACG CCAACAGCTC TTCGCGGATC TCTTCTCGGG TCATTAGTGG TAGATCCCCC      31080

GGACGGTGCG CGAGATCGTG GCAGGGTTCA CGCCGTAGTT CTCGGCGAGA TCCTTCTGCT      31140

TCATACCGCC CAGGTACGCC TGGCGGATGT CCTTGACCTC GCGCTCGGTG AGCTTCTTGC      31200

GGTTCGGCCG GCTCGGGCCG GTCTCAGGCT TGACCTGAGC CAGCGCCTTG CCGAACAGCT      31260

CGTTCTGCGT CCGCTGCTTG ATCGCGTACC GACGGTTCGC TGCAAGCACC TCGTTGAGCC      31320

GCTGGGACAA CTTGACATTG GCCTCACGCA CTACCTCGAC CTCTCCGAGC AAGTTCGTGA      31380

TCCGGTAGTC CTTGTCCTGG TTCTCGATGG CCAACCGGTT GTTCTCCTCG AAAGCATCG      31440

AGACCTTGTA TTGCGCCTCT CCCAGCGCAG CTTTCAGGTG CTTCTTCCTC ATTCAGCGCC      31500

CCTCTCTCGG CGGAACTGTT CGTACTCGTC TTCGGTCATG TAGTAGTAGT AGTCAACGAC      31560

CTTGTCCCAG TTGAAGGTTC GGGACGTGCC GTCATCGAAC GCGATGATCA GGACACCCTC      31620

TTGGGTGTCT AGGATCGGCT CGCCAGCCAC GACGTGGAAG CGGTCCTCGA GGGTCACCGC      31680

AGTCGCTCTG CGTGCCATGT CAGTTCCTCT CAGTAGCTGT AGGGGACATC CGGGATGTCC      31740

TGGTAGGTGT TGGGTGCGAT CTGTCGGAGC TGCCGAAGCA ATTCCCCTGC CAGCTCACGG      31800
```

-continued

| | | | | |
|---|---|---|---|---|
| ATCTCGGCAT | CCGCGGCCTC | GTGCCAGCGG | GCCTTGATGA | CGTACCGCCA | CGCCCGATGG | 31860 |
| TTGCCCGTGA | CGACCATCGG | TGAGTTCGTC | ATGTTCGGCA | GGACAGCTCG | CGCTGCCTCG | 31920 |
| CGGGCCTGCT | TGCGCGGCAA | GCCCCGGTCA | GCCAGCCGGT | TGACGATGTG | TTCGTAGACA | 31980 |
| GCGTCAATCT | CAGAGCTGAC | GGACTCCATG | ATGTGGACGA | GGTCGTCTCG | GTCGTCGGGG | 32040 |
| TGGAGCTTGA | ACAGAGCCGG | GGGCAGATGG | ATGCCAAGGT | CGGTCGGATC | CACATATCGC | 32100 |
| TGAGACACCA | CCGAGAAGCT | CAAGTGACGG | TGACGCTCCA | GCTCGGTCAG | CACCGACCTG | 32160 |
| CTGGCCTCGA | TGTAGAACGT | CGCCGAGGCG | TGCTCGAACA | CGCTCTCGTG | GCCCAGATCG | 32220 |
| ATGATGTGGT | TGAGGTAGTC | CTCGTTCTCG | GCAGTTGCCG | GGTTCGGTCG | GTGGAACGAC | 32280 |
| CGGTAGCAGT | TCCGGCCCGC | GAACTCGGCC | AGCTCGTCGG | CATCGAAGTC | GCCGAAGTAG | 32340 |
| GGATCTTCGT | CCTTGGATTC | TTCGAAGTCA | TCGACCTCGA | ATCCGATGTC | CGCAACGCA | 32400 |
| CCCGGATCGA | TCTCGGTGGC | AGCGATCAGT | TTGGCTTTCA | TACTCTCCGC | TCAGAGTTGG | 32460 |
| TGGAACGAGG | TCAGCCAGGG | GGCAGCGAAG | CCCTTCTACA | GCTCCCCTTG | GCTCGTTACC | 32520 |
| GGCTTCTCGA | CCTCGGTGGA | TGTCAAGTAG | TCGAGATGAC | TACTTCTTGT | CGGGCCATTG | 32580 |
| CGCGTCACAC | TGCTGATCGC | GAGGTGCGGT | GCAGGAGAAC | AGCGCGTACG | GCTTGCCCGT | 32640 |
| CTTCTTCGAG | ACGCCCGACT | TGTAGACCAT | CTCGCCGTGC | TGGCAGTACC | GCTTCTCGCC | 32700 |
| ACCAGGCGCT | TCCTGAGCTG | CCTGCGGGGC | GCGAGACTGC | TGCTGGCCAC | CGCCGCCGCC | 32760 |
| GTTGGCCGGC | GCGGATCCAC | CGGAGCCTGC | GTAGTGGCCT | GCGATCTGCT | GGACCTTGTC | 32820 |
| CATCAGCGCC | TTGAACTCGG | CGGTGTTGAC | CTTGGCCAGC | ACGTCGGCCG | GGTCCGCACC | 32880 |
| CTTCACGACC | ACCCACGGGT | CGCTGTACTG | ACCGGCGAAC | TTGAACGTGG | CCGACACCCC | 32940 |
| ATCGGTGGAG | TGCTGGACCG | CCATCGAGTC | GCGCACAGCA | GCCGAGGCCG | TCGTCACCGT | 33000 |
| CGCCGACGGC | GCGGTCTCAG | GCTCAGGAGC | CGGGGCCGGC | TCGGGCTGGG | CAGGGGCGGT | 33060 |
| GCTCCACGGA | TCGTCGTAGG | ACAACTGGTT | ACCTTTCACT | TAATGGGCA | TGCGCCGTTG | 33120 |
| GCGCACTCTT | CATCGACACC | GTCTTCGACG | GCTTTGGCCG | CAGCAGATTC | GTACTGCTGC | 33180 |
| TTGGTGATTC | GCTCGTACGG | AGCCTGCGGG | AAGCTGGACT | CCGGGAAGAT | CGTGGAGCCC | 33240 |
| TTGATGAGCC | CCGCGAACCT | CTTGAGATCG | GCTGCGACAT | CCTCGGCCTC | GTAGGCGTCT | 33300 |
| GGATGGACGT | TGGCGGTGAA | CGACACCGCG | TTGTCAGCCC | AGCACATCTG | GTAGAGCGCC | 33360 |
| TGGAACGCCA | GGAGCTGGTG | GAGGGTCAAC | TCGTCGGCTG | ACTCAACGAT | CTCCTCGTCC | 33420 |
| CAACCGAGTT | CCTCGACAGC | CTGGACCAAC | GTGTCCTTGG | TCGGGATCGA | AACCACCTCG | 33480 |
| GTGTTCGGAG | CGAAGAGATC | CTTCTCGATC | TCGTAACCCT | CGGCTGCCAA | CCTCCGCAGC | 33540 |
| TCGGCCATGT | CGCTGTTGAG | GTTGAACCGC | ACACGCCGGA | TGAAGTACCG | CGAGAAGATC | 33600 |
| GGGTGGATCC | CCTCGGAGAC | TCCTGGCATC | TTCGCCACCG | TGCCTGTGGG | AGCGATGGTT | 33660 |
| CGCTTCTTCA | CCGGGACAGG | GATCCTCAGA | TCATGGGCGA | ACCGTTCGGC | CTCTGAGTCG | 33720 |
| ACCTCAGCGG | CCATCTCCCG | CAAGAACTGG | GTGAACCGCT | TATCTCCGGG | TGCCTCGGAG | 33780 |
| TACCTGCTAC | CTGTGAGGGC | CAAATAGGAG | GCAACTCCGA | GATGACCCAC | GCCGATGCGA | 33840 |
| CGGTTTCGGT | CCAGAACCTC | CCGGCTCTTC | GGGTCGGCCA | CTTCCGAGAA | CGTCGCCCGG | 33900 |
| ATCAGGAATC | TCGTCATCAG | ACGATGCGCC | CGGATCAGGT | CGAGGTAGTC | GGTCTTGCCC | 33960 |
| GCCGGCGTCA | CGAACGCCGC | CAGGTTGATG | TGGCCGAGGT | TGCACGGCTC | CCACGGTTCG | 34020 |
| AGAGTGATCT | CGCCGCATGG | GTTGGTGCAG | ACCACCCGGT | TGGGCTCACC | GACGTTGGAC | 34080 |
| AGTGACGAGT | CCCACATCCC | CGGCTCTCCG | TTGCGTACGG | CTCCCTCGGA | GAGTGCCTTG | 34140 |
| AGCACTCGGT | GGGCTCGCTT | CTGCTTGGGC | ATGTCCTCGC | GGGCGACCGC | GAAGCTGCCG | 34200 |

```
TAGCCCTCCT TGGCCAGACG CCAGAACTCG TCGTCAACCT CGACCGAGAT GTTCGTCGTC    34260

CAGTGCTCGC CCGTGCTCGC CTTGATGTTG ATGAACTTGT CGATCTGGTA GTCGTCCCAG    34320

TGCATCATCG ACATCCGCGC CGACCGGCGC ACACCGCCGG CCACAACACA CTGAGCGATG    34380

GCGTGGTCGA CCTCCATCGC GGCGATGCCG TCGAGCGTGA TCCCTGCGTA CTCCGAGAAG    34440

ATGTTGGCGA CCTTCTGCAG CATCACAGCG AACGGCAGCG GGCCGCTGGC CACTCCACCG    34500

AACGTCTTGA GCTTGGCCCC TTGCGGCCGG ATGCGGCTCA CGTCGTACAC CCGCTGGTAG    34560

TGGACCGTGC CGGGTCGGTA GTGCGTGTCG ATCAGATCGA CCAGCGCAGC AGCCCAGCCC    34620

TCTCGTGAGT CCTCGATGGC GTAGGCACCG GCCCAGTCGT GGCTGTAGTG CTCCGACAGA    34680

ATGCCTACAT CCTTCATCGC CTGGTAGTCG ACATGCTCTG GATCACAGAC GATCTCGACC    34740

CGCAGGGGGT TTACGACCTC GGGGTAGCCT TCGAGGTAGT GGTTCGAGTA GTTCGCCCCG    34800

ACTCCCCCGC CCTCCATCAG GCGCATGAAC GTGAACTGGA AGTGGTCCGA GATCTTCTCG    34860

GGCCAGCCAG CTACCCAGCA GTTGAAGAGG TGCTGCGCGT TCTTGACCCC CGAGGCCCAC    34920

AGATGCCGAC CTGCCGGCAG CACCTTGAAC TTGGTCATCA GACGAACGAG ATCTTCTCGC    34980

TCTCCTTCCA ACATATGTCG CCGGTCGACA AGAGCAAGAT TGCCGTCCAC GACCCTCTCG    35040

ACCGTTTCCG GCCAGGTTTC CTTCGAGCCG TCAGGCTTGG TCCTGGCGTA GGTTCGGTTG    35100

TAAACGAGTT CACCGGTTGG TCCCCAAGGG ATTTCGTCAG TCAACTACTT CCTCTCAGTC    35160

AGTTCGTATC GCTTGAAATA GGCGTCGGCA GAGTCGCCGC CAGAGAACGA GACCCCGTAC    35220

TCGACCGGGC CTGCACCACG CACCTCGCAG GTAACGACGC CCTTCCTTCC CCGGAACATC    35280

GGCCAGGTTC CCTTGGAGGG GTGCTTGGTC TCGTCCCGCT GGACGATGAC CTTGGTGCCC    35340

TTCTTCATGC CGACTTCCGT TCTCCGTAGC CGGGAGTGAA GCAACCCCCG ACGTACAGCT    35400

CGAGATCTTC TTGCGACCAG TTCTCCAGTC GCATCGGCGG CTGGTGCGGG AACAGCTCCG    35460

GGAACACCTC GGCCCGGTAC AGCTCCGAAC CGGGCATCCC GTTGAACGTC GGATCAAGAA    35520

TGTTGTGCAT GGCACCTCCC TCCCAAGAAC TCGGAGATCG GCGGCTCGTA GAGGTAGCCA    35580

TCGCGCAGCT CGGGGTTCTC GATGAGCATG ATCGCGATGT TCGCTGTGGG GTCAGAGTGC    35640

CCATCCCCCT GCGACTTTCG GATGTCTGGG AAGATAGCGT GCTTGCTGCC CGGACCATCC    35700

TTGACGATGA CCTTGCCCTT GTCGTCCTTC TCCACGCCAG CCGTGATCGC GATGATGTTG    35760

ACGTGCTCGG TCAGCGACTT GTGAGCGCGG AACAACCGGT TCTGCCCGCT CTTATCCTTC    35820

GGGGAGATCC CGTCGGTGTA GCGGCTCCTG ATCGCCTCTG CATAGCCCCC GTTCTGAGCG    35880

TCCAGAGCCT TCATCGCCAG CGGGAGGATG TCGACCAGGT ACCGATTGGT CGACTCCCCC    35940

TGCAGAGCCT CTTTGACGTT CTCGGACGAG TAGTGGCTGC GCTCCTGGAA CAAGTCGCGG    36000

GCCTTGGCCG CTCCCGACAG GATGTTGCGA ACCTGATTGC GTACGTAGTG AACTGCCTCA    36060

CCACGGTGCA AGCTCTCCAG CGTCTTCTGG ATGTACGGGC TCTCGAGGTA CCAGACCCAC    36120

AGCTCTTGGA TGATCTCCTC GGCTGTCAGG TTGGTCTCCC AACCGATCAG CGCCTTCCGG    36180

GTGGCCCTGC TGAACAGCTT GCTGATGTCG TCGGTCAAGG CATCACCTTT CGTAGGTACT    36240

CCTCCCGGTC CAATCGGCGG TCGAGGTGTC GAGTGACCTC CTCCGCGAAG ACCTCGCGGA    36300

CTTCGCTGGA GGTGATCTGG CGCGAACGTG CGTTCTTGTG CAGGTACGGC AGCTTGGTGG    36360

CTGTCAAGTT CTAGACCTCC CAGACTCGGC CGTCGACCGA GAACCGGCCT CCGACAATCG    36420

GAACAAGCTC AGGCTTGACG TGCTGGCCGT CGACCGTCAG CAGAGCAAAA CCACTCTGCC    36480

AGTTGGCTGT TGCACCCTTG AGGTACTGAG CTAGCTTCAT GTTCATCAGG TTGCCGACCT    36540

CCATCGACCA CAGCACCTTC TGGTTGCCGC CGTAGCCCAG CGTGTGTGGC TTGATGCCCT    36600
```

```
GGCGGTGGGT GTGTCCGATG ATCACCGACG TGCCGAACCG CATCATCGCG TTGTACGCGG    36660

TGTCAGCGGA CTTCTGCGTC ACCCGGACCC CACCACGGTG GCCGTGGGTG GAGATCCAGC    36720

CTGGAGCGAT CTTGTAGAAC TCAGGCAGCA CGTCAACACC GAACCCGTCG AAGTCCAGCA    36780

GGTTCTGGAA CTGGAACGAG CTGACGTACT CGACCAGCGC CGGGGCGAAC TGGTGCAGGT    36840

AGTCGACTGG CCGGCGGTCG TGGTTGCCCT CGTGGACACC AACCGGGCCG TCGTAGACCT    36900

GGCGCAGCGG CTCCAGGAAC CGCCGCTTGC ACTGCTCGGA GTCGGGCTTG ATCCGCTGAG    36960

CGAACTCTTC CTTGGTGCCC TTGGTCCACC GAGACGGGCT CGGGTAGTCC ATCAGGTCAC    37020

CGATGTGGAC GACCTCGTCA GGCTGGGTGT CCCCGATGTA GCCGATGACC GCCTTCAACT    37080

GCTTGCGATC ATCGAACGGA ATCTGGGTGT CCGAGATGAC GACGATGCGC TTGCTCACTC    37140

AGCGACCTCG GTGAAGGGGC CCCGCATACG TTCCTCGTGG GAGCTGGCGT TGCCTCCTGA    37200

CCAGCGTCGC TTGCCCACCT TGGTGTGGTG CAACCCGTTG GGGTAGTAGA TCCACTTCAC    37260

TCCTGTGGCG TTGGTGACGG TCTTCACATC GGCAGGAACG TCCAGCAAGG TGTCCCACTG    37320

GCGAGGCCCC TTGGGATACC GCTCGTCCTC GGGGAGCTGC ATCTTCTCCA GAACGCCTGC    37380

GTAACCGGCG ATGTCGACCA CCGTGTCCTG GTGGTAGCCG TTCTCCATGA ACCGGGCGAT    37440

CTTCAGCAGG ATCATCATGA CGGCCACGTC CTCCGGGGTG AACTCGACGC CGCGCTTGTA    37500

CGCGCCCCAC AGGGTCGCGA TGCGTTCGTG GTTCTCCTTG GCGTCCCCGT AGTCCTGGGC    37560

TCGCTGTCCG TTGATGATCT CTTCGGCGGT GGTCAGAATG CTCACAGTCC AGTCTCCGAT    37620

GCGGTGTAGT AGTCGATCAG CTCATCGAGC TGGTCCGGTT GATAGCCGAG GATCGGCTTG    37680

TGGGTGTCAG TGACGACGAC GGGAACCGAC ATCGCGTTGA GCACCTTGGT GACGTAGTCG    37740

TACGCCTCCG AGTTGGCCGT GACATCGACT GCGTCGAAGT CGATCCCGGC AGCCGTCAGC    37800

TTGTCTTTGA CTCGCTCGCA TGGCTTGCAG CCGGGACGGG TGTACACCGT GACCGGCGCG    37860

AACAGCGTTC TCACGTGAGC ACCATCCCAG TCGATGTATC GGTCTCCATA CATCAGATCC    37920

TTTCCAGCAG AGCAGCTTTG CCCTGCGATG TGACTAGTGA GTTGACATCC TCGCCTTCTG    37980

GCATCGGGAT GATTCGGGCG TTCGGCAGCG TCTTCGCCAC CGACCGGGCG AACTCCATAC    38040

CGGCGTCGTC GCCGTCGGCC AGGATGTTCA CGTTGCGGTA GCCCAGGAAC AGCTCTCGGA    38100

AGTACGGCTT CCACTTCTGG GCTCCGCTGA GCCCCACCGT CGGCAGCCCA CACAGCTCGG    38160

CGGTGATCGT GTCGAGTTCT CCCTCGCAGA TCGCCATGTC CTTGCTGTAT TTGGTCAGCG    38220

CGTAGGTGTT GTAGAGCCGG TCCTTCTCCC CTGGCATCGA CAGGTACTTC GGTGTGCCAC    38280

CGTCGATTCG GCGATACCGG ATCGCAGCTA CCGTCCAGTG ACGCCAGGGC GACCACCGCA    38340

TATACGGAAT CGCCAGGCAG CCCCGGTACA TCTCATGTCC AGGGAGTGGG TCGTCCACGA    38400

ATCCCAGACC GAACCGGCTT AGTTCCGCTC GGCCGGCCAG CCCGCGACTC GCCAAATACT    38460

CGTCGGCTGG GCTTCCGGGC AGGCTTTCTC TGTACCGGGA CGTTGCCTCC CACAGATAGG    38520

TTCTCTGCGA TTCGCTTAGC CTCTGCAAAT GTCACCTCCT CTTCGTGACG AATGATCGAG    38580

ATCACGTCTC CACGGACCCC GCAGGCCATG CAGTTGTAGC CCTGTAGGTC GTAACTGACT    38640

GCGGCAGACG GCGTTTCGTC GCCGTGGAAG GGCACAGGC ACTTGTTCCA CTCGTGGTGG     38700

TCAGGTGGTG GTTCCCAATC CGGGTGGTAG CGAAGAATCG CCCTCGCGAT GGGCGAGTCG    38760

TTCATTCGTC CTCGTCAAGC TCCTCGGGAG AGAGCCCTTC GAAGATCCCG TTCAGGACGG    38820

CGGCGAAGCC CTCGCCGGTC TCCGCTGCGT CGAGCATCTC TGCAATCGTC TTTGCCATGT    38880

TTCCTCCTGG TGGATGTCAA GTTCGAGACA GCTTGTCAGC CTCGACTGGA GCGATGCGCT    38940

CCCCGATGAC TTGGACGGCC GGCGGGTTCA GCAGGTACTC GATGGCCCGT TTGAAGAACT    39000
```

```
CGATGCAGTC CCTCGCCCAG CCCAGCGTGT ACTTGTTGCA CATCGTGCAG AGCAACCCTC    39060

GGACGATGCC TGTCTTGTGA TCGTGGTCGA CCGACAGGCG CTTCTTCTTA CCGTTGGCTC    39120

GCTGGCAGAT GTAGCACCGA CCACCTTGGA ACTCGTAGAT CTGCCAATAC TCATCGCCGG    39180

TGATGCCGTA GGTGGCCAGG ATCCGGGTCT CCCAGCTCGT AGAGCTGCGA GCCGTCCTGA    39240

ACTCTCGGTG ATGAGTAGCG CATCGTGGCC CTGGATACTT GGCGTCTCGC GTGAGCGGGA    39300

GCCCCTGTGC GACACAGTCT TTGCAAGGCT TCCGCTTGTG CTTACGGTTC TGCACCCGGT    39360

ACCCCGGAGA CCTCTTCGCC GCCCTCGGCA CGCGCGTCCT CCTCCCGGTT CTCCATCACC    39420

ATGCAGAACC ACGACAGCAG CCCTGCCAGG GAGATGTAGA AGGCCACCAG AACTTGGCCG    39480

CTCACTTCAC CATTCCTCGA ACCCACCAGC GAGACAGCGC CTTACGCCCT TGTCGAGCG    39540

GGGTCAGCTC GCGCTCATCG TCCTCACCGA AGTCGAACTC GATGCTGGCG ATCTCGTAGC    39600

CGAGGATCTT GAACGACACG TTCATAGGCG GTCTCCGAAG TTGATGACGG GAATGCCGGC    39660

CCTTTCGGCC TCTCGCATGC AGTGCCGGGT GCCGACTGAG TTGCCGAGGG GGAACGCCAG    39720

ACAGATGTCC GCACCGGCCC TGACCATCTC GATGTTGCGG AGGATGCCAG CCCGCTTGCC    39780

GTAGCGTTCC CAGTCGGCTC GGTGCAGCTC GGGGAGCACG TCCCATCCCT CCTGCTTCAT    39840

CCCCCAGGCC CAGCGGTCTG CGATGTCGTC AGCGCCGCGA GCGCCGCCGT GGACGACCGT    39900

GAGACCGGAG AAGGACCGGT GGTACTCAGT GGCCAACGCT TCCCAGACCG TGGTGCGGTC    39960

CTTCCAGATC CGAGATCCGG TGATCAGTAC TCGCCGCATC AGATCGCCTC CCACTGCAGG    40020

CCGTCGTGCG ACGTGACCAG CTCCGCTTCG TAGACGCCGT AGCGGGTGGC CAGGAACTGG    40080

ATCATCTGCG CCTGCTTGTA CCCGAAGGGA CATTCGTGGA CGCCGCTGAT CGGGTATCTG    40140

ACTCCGTATT TCACTTGATC CACCGCTTCG CGATTCGGTC GACGTTCTCC TCGGAGACGT    40200

TGCGGGCGAG GCCGGTGAAC TCCTGGCCGT GGACCTTGGT CTCGATCACG CGAGGCTTGC    40260

GGGGATCCGG GCTCTCCGGG TCGATCCGCT TGTGGGTCCA GACGGTCGGC TTCGTCTTGA    40320

TCAGAGCGCC CAGCACCTGC TGGCGCAGTG GGTTGGTCTT GCGGGCATA GCGTTTGGAG    40380

TGGTCATCTG GATCCTTTCC TCGGTGGCTG TCAAGTCGGT GTGCGTAGTG AAGCCCCCCC    40440

AGGCATGCGC GCCCCGCCTG GGGAGAGTTG ATCAGCGCAG TTCGATGTCG GGCAGGATCG    40500

CCTGCGGCTT GAAGTTGACC TGGTAGAAGT CGGTCGAGAC GTTTGCGCCA TCGACCTGCT    40560

CCATGAAGTA GGAGACGTTG TCCGACAGGC CCAGGAAGTG CTTCTTGATC CCGTCCTTGG    40620

TCTTGCAGGT CACGTCGAGC TTCTTCGACG CGGTGTCCGC GTTGATTGAG CACCGGCCCT    40680

GGATCTCGAG CAGGTACTTG TCCGTGATCC CGTTGAAGAA CACGATCCGG CGATTGATCT    40740

CGAAGTTGTC AGCGGCCTTG CTGACGTTCT CCGATGCGAC GTCGGCGTCG GAGGTACACG    40800

CGGAGAGGCC CAGGATCGCC GATCCGGCGA TGAGTGCGGT GGCGATGATC TTCTTCATGT    40860

TCGCTACTTT CTGTTTGGTG GATGTCAAGT TAGTGACCGA AGTCGTTGAT CTGCATAGTG    40920

TCTCCGACGA ACTCCAAGGA AGCGAAGTCT TGTCCCGACG GGTCCGACTT CCCCCCTCGG    40980

TTCTTGACCG TGGAGACGTT GAGCATGTCC GGGCCGAACC CGTCCGATAC TCGGTGGAGA    41040

GTGAGGATCA TCTCAGGAAC ACGCCCGATC TGACCTTTGA TGCCCGACAA CGGGATCGGC    41100

TTGTCGCCGT CGTTGTGCGG GCCGGTGACG TGGTGGAGCC CGACGACGCA TGAGCCTGTC    41160

TCACGGCCCA TCTCGTGTAG GTAGTCCATC AGCGACTCCA GACCCGAGAA CGGGTCGTCT    41220

CCCTCGCTTG AATCGGTGCG GACGTTGGTG ATGTTGTCCA CGACGATCAA CGCTGGGAAG    41280

TCCTCGTACA GCGCGTCATA CGCGGCCAGA GCGTTCTCGA TCTCGTCCAA CGACGGTGAT    41340

GCCTTGTAGT TGAACCGGAT CGGGATCTCG TCTAGTGAGT CAGCTACCGC GTCCTCGATG    41400
```

```
TTCTGCTCGC GAACAGCCCG CGTAGCTCGT TCGAGCGACC ATCCGCTGAG GATGGACACC    41460

GAACGGGAGA GCTGGGTGAA CGCATCAGAG TCGGCCGAGA AGTACAACGT CGGCACCTTC    41520

GACTTGAGCG CGTAGGCGAG GACGAACGCC GACTTCCCGG TGCCGGGGCC GGCGCAGACC    41580

AGGACTAGCT GGCCTCGTCG GAGATGTGTA CCTTTCTGGT CAAGCGCGGC CCAGACCGGG    41640

GGTAGCGGAT CCCCCGCCGA CCCTCGGATG TAGAGCGATT GTCTAGGTGT GTACACCTTC    41700

CTCCTCGTGG ATGTGATTGA CCAGGTCATA GATCTCGTCG CGAGAGACCA GCCGGCCCCA    41760

GGCGTCGATC CCCACGTGGA TCTGTCTCCG GTGGATGTGT CGGACAGGA  TCATCGGCGA    41820

ATGCGTGTGC CCGTGGATCA GGATCTTGCC ATCGTCACGG AGCCTCCACT GGGTGTGTCG    41880

GTCCTCGCTG GTGTGGTCCC CGACGTATGG GAAGTGGCTC AGCAGAACAT CTGTGTGCCC    41940

GCCAGCGTCC CCGTACAGCG GCACCCGGAT ACGAGCTGCC GTCGACACAT GCTCGAACAC    42000

CATCCAGTAC GCACCAACCA GCTTGTGAGC ATCGCGGTTC ATCGGGTGGG GCCCATCGTG    42060

GTTGCCCAGG ATCAGCCGTT TGCGGCCTGG CCGATCCGAG ATCCACCCGA GGGCATGTAT    42120

CTGCCCCTTG GTGGAGCCAG AGGAGATGTC ACCTAGGATC CAGACCGTGT CGTCCTTGCC    42180

GACGACCGAG TCCCACGCCT TCGCCAGGGT GGCGTCGTGC TCTTCGACAT CATCCGCCAG    42240

GTTGCGGATC TCCATCAGCC GCTTGTGTCC GATGTGTAGA TCGGACGTGA ACCAGGTGTT    42300

GCTCATGGCT TCCTTTCAGA ACGGCGGGCC GTACAGCTCG ATCACCAGCG CGTGCAGCTC    42360

CTCTGCCGCG TCGTCACGCT CGAATCCGCA GCAGGAATCG TGCCGGTCGA GGATTGCGAC    42420

GATCTGGTCG TAGAGGCTGG GCCTCACTTC ACCTTCTTCG GATCGATCAA GGCGTCGTGA    42480

ATCGGCCGAC CGGCGCGAGC CGCGTGCGTC TCGGCGTCCA AGGCTCGCTG CATCTGGTTC    42540

ATCAGCCGGG TGCCGCGCAG CTTGAGGATC TTCATGGTCG CCCGACCCTT GTATCCAGCG    42600

CGGTGCATCC GTAGGACGCA GGCTGTCTCG TGCGGGGCTA TAGGTGACCT CAGCGACGGG    42660

TGGTTTGGAT CCCAGTTCGT CATGTCTTCC TCTCGGTGGC TGTCAAGTTG GTCACAGACC    42720

GAACTCTTCC TGGTACTGCG GGATGAAGTG GCCGGCCGTT CATGTTCGGC TCGATACCTC    42780

TCGCGTCACG AACTCCTGCC CGTTCCATCT CCGACCGTCC TCGAACTCGA TCACGATCTC    42840

TCGTCCGGGA TGACGCACGG CCTCCGCTTG GGCAAACCTG CGTGCAGCCT CTGGGGTCGG    42900

GAACGGAAAC TTCTGCGAGG CGTACAGCTC CTGGTGCCAC TTCGGCTTGT CAGGAATCGG    42960

CCCCATTTCC ACGTACGTGT AACCCGCGTC GGGGTCGAGT TCGAGCGTTT TCTTGTATTC    43020

CTTCGTGCCT GCCTTAGAGG GAAGGTGAGT ATCGGTGGCT GTCAAGGTGA CCTCACTTAA    43080

AAACAGGGCA GCTGTAATTC ACATCACAGA AGCCGCATTT GTCAGGTTCA GGCAGAGGCT    43140

CGAAGTCACC AGCCTGGATC CGAGCCTCGA CCTCATGGAA CCTCTCGGTG ATCCGCTCCC    43200

GCGTCCAATC GGTCAGGTCG TAGGGCGCAG TGGGCTTCGC CTTGATGCCC TTCTTCCCCG    43260

CCATGAAGTA GTCGCCCGTC TTCGGAGCCT CCACGTCATA GGTCATCGCG ACCGCGAGCG    43320

CGTACACGCC GAGCTGGAAG TCGTCACCCG GCGAGTTGCC GGTCTTGTAG TCCCGGACTC    43380

GAAGCTCACC GTTGACCACG ACGACCGCGT CGATGAACCC TCGGACGCGG ATGCCGTCCA    43440

GCTCGATGTT GAACGGAAGC TCGATGGCCG GCTTGGGCTG TTCACACTCC TTGCAGTTGG    43500

TGTCTTTCCA CGCCTCCGTA GAGCAGATCC CTCGCCCAGG GGTAGTCCAG ATCTGCTGGC    43560

CCTTGTCCTT CCGCCACGCG ATGAACTTCT CTACCTGCTC CAGTCCAAGG TGGAACCGGC    43620

GCTCGATGTC ACGCTCACCG TTGTACGGCC CGGACCAAAA CCACCACTCG AAGTTCGGGG    43680

TTTCGTCGCA CAGTGCTCCG ATGTCCTTGG CGTACTCCTC GCGGAAGATC TCTTGTGCCC    43740

GTTCGAGGCT CATCTCGCGG CCCTCGGCCA GAGCCTTCTC GTAGACCTCA GCGACGGTGT    43800
```

```
GAAACGCGGT GCCCTGCGGC AACCACGCCG CAGGACGAGC CCATACCTTG TCGATGCGAG    43860

CCAGCTTGTA CGCCTGCGGG CAACGTGTGT ATTGGTTCAA CTGGCTGACG CTTCGCAGCG    43920

GCAGCAATGT CTTGGTGTCT GTCACGCAGC GGCCATCCTT CCCTTGCCTA TCGTCTCGTT    43980

CAGCGCCCCG TCGACAGCGA CACTGAGCAG TTTTGCGACC TCCGACATGT CAATCGGATC    44040

CTTGGGGAAT TGGTCAGCCT GAGTCATCCT GAGCACCATC CACTCGGTGC CCTTGTCGCA    44100

GTGGATCATG GTCGGATCCT TAATTAAGAT CCTTTAGTGA GGGTTAATTG CGGCCGCGAA    44160

TTCTTGAAGA CGAAAGGGCC TCGTGATACG CCTATTTTTA TAGGTTAATG TCATGATAAT    44220

AATGGTTTCT TAGACGTCAG GTGGCACTTT TCGGGGAAAT GTGCGCGGAA CCCCTATTTG    44280

TTTATTTTTC TAAATACATT CAAATATGTA TCCGCTCATG AGACAATAAC CCTGATAAAT    44340

GCTTCAATAA TATTGAAAAA GGAAGAGTAT GAGTATTCAA CATTTCCGTG TCGCCCTTAT    44400

TCCCTTTTTT GCGGCATTTT GCCTTCCTGT TTTTGCTCAC CCAGAAACGC TGGTGAAAGT    44460

AAAAGATGCT GAAGATCAGT TGGGTGCACG AGTGGGTTAC ATCGAACTGG ATCTCAACAG    44520

CGGTAAGATC CTTGAGAGTT TTCGCCCCGA AGAACGTTTT CCAATGATGA GCACTTTTAA    44580

AGTTCTGCTA TGTGGCGCGG TATTATCCCG TGTTGACGCC GGGCAAGAGC AACTCGGTCG    44640

CCGCATACAC TATTCTCAGA ATGACTTGGT TGAGTACTCA CCAGTCACAG AAAAGCATCT    44700

TACGGATGGC ATGACAGTAA GAGAATTATG CAGTGCTGCC ATAACCATGA GTGATAACAC    44760

TGCGGCCAAC TTACTTCTGA CAACGATCGG AGGACCGAAG GAGCTAACCG CTTTTTTGCA    44820

CAACATGGGG GATCATGTAA CTCGCCTTGA TCGTTGGGAA CCGGAGCTGA ATGAAGCCAT    44880

ACCAAACGAC GAGCGTGACA CCACGATGCC TGCAGCAATG GCAACAACGT TGCGCAAACT    44940

ATTAACTGGC GAACTACTTA CTCTAGCTTC CCGGCAACAA TTAATAGACT GGATGGAGGC    45000

GGATAAAGTT GCAGGACCAC TTCTGCGCTC GGCCCTTCCG GCTGGCTGGT TTATTGCTGA    45060

TAAATCTGGA GCCGGTGAGC GTGGGTCTCG CGGTATCATT GCAGCACTGG GGCCAGATGG    45120

TAAGCCCTCC CGTATCGTAG TTATCTACAC GACGGGGAGT CAGGCAACTA TGGATGAACG    45180

AAATAGACAG ATCGCTGAGA TAGGTGCCTC ACTGATTAAG CATTGGTAAC TGTCAGACCA    45240

AGTTTACTCA TATATACTTT AGATTGATTT AAAACTTCAT TTTTAATTTA AAAGGATCTA    45300

GGTGAAGATC CTTTTTGATA ATCTCATGAC CAAAATCCCT TAACGTGAGT TTTCGTTCCA    45360

CTGAGCGTCA GACCCCTTAA TAAGATGATC TTCTTGAGAT CGTTTTGGTC TGCGCGTAAT    45420

CTCTTGCTCT GAAAACGAAA AAACCGCCTT GCAGGGCGGT TTTTCGAAGG TTCTCTGAGC    45480

TACCAACTCT TTGAACCGAG GTAACTGGCT TGGAGGAGCG CAGTCACCAA AACTTGTCCT    45540

TTCAGTTTAG CCTTAACCGG CGCATGACTT CAAGACTAAC TCCTCTAAAT CAATTACCAG    45600

TGGCTGCTGC CAGTGGTGCT TTTGCATGTC TTTCCGGGTT GGACTCAAGA CGATAGTTAC    45660

CGGATAAGGC GCAGCGGTCG GACTGAACGG GGGGTTCGTG CATACAGTCC AGCTTGGAGC    45720

GAACTGCCTA CCCGGAACTG AGTGTCAGGC GTGGAATGAG ACAAACGCGG CCATAACAGC    45780

GGAATGACAC CGGTAAACCG AAAGGCAGGA ACAGGAGAGC GCACGAGGGA GCCGCCAGGG    45840

GGAAACGCCT GGTATCTTTA TAGTCCTGTC GGGTTTCGCC ACCACTGATT TGAGCGTCAG    45900

ATTTCGTGAT GCTTGTCAGG GGGCGGAGC CTATGGAAAA ACGGCTTTGC CGCGGCCCTC    45960

TCACTTCCCT GTTAAGTATC TTCCTGGCAT CTTCCAGGAA ATCTCCGCCC CGTTCGTAAG    46020

CCATTTCCGC TCGCCGCAGT CGAACGACCG AGCGTAGCGA GTCAGTGAGC GAGGAAGCGG    46080

AATATATCCT GTATCACATA TTCTGCTGAC GCACCGGTGC AGCCTTTTTT CTCCTGCCAC    46140

ATGAAGCACT TCACTGACAC CCTCATCAGT GCCAACATAG TAAGCCAGTA TACACTCCGC    46200
```

```
TAGCGCTGAG GTCTGCCTCG TGAAGAAGGT GTTGCTGACT CATACCAGGC CTGAATCGCC   46260

CCATCATCCA GCCAGAAAGT GAGGGAGCCA CGGTTGATGA GAGCTTTGTT GTAGGTGGAC   46320

CAGTTGGTGA TTTTGAACTT TTGCTTTGCC ACGGAACGGT CTGCGTTGTC GGGAAGATGC   46380

GTGATCTGAT CCTTCAACTC AGCAAAAGTT CGATTTATTC AACAAAGCCA CCGAACGCCA   46440

GCAAGACGTA GCCCAGCGCG TCGGCCGCCA TGCCGGCGAT AATGGCCTGC TTCTCGCCGA   46500

AACGTTTGGT GGCGGGACCA GTGACGAAGG CTTGAGCGAG GGCGTGGAAG ATTCCGAATA   46560

CCGCAAGCGA CAGGCCGATC ATCGTCGCGC TCCAGCGAAA GGGGTCCTCG CCGAAAATGA   46620

CCCAGAGCGC TGCCGGCACC TGTCCTACGA GTTGCATGAT AAAGAAGACA GTCATAAGTG   46680

CGGCGACGAT AGTCATGCCC CGCGCCCACC GGAAGGAGCC GACTGGGTTG AAGGCTCTCA   46740

AGGGCATCGG TCGAGGAACT TTCGGCGGCT TTGCTGTGCG ACAGGCTCAC GTCTAAAAGG   46800

AAATAAATCA TGGGTCATAA AAATTATCAC GTTGTCGGCG CGGCGACGGA TGTTCTGTAT   46860

GCGCTGTTTT CCGTTGGCCG TTGCTGTCTG GTGATCTGCC TTCTAAATCT GCACAGCCGA   46920

ATTGCGCGAG CTTGGTTTTG CTGAAACCGA CACACAGCAA CTGAATACCA GAAAGAAAAT   46980

CACTTTGCCT TTCTGACATC AGAAGGGCAG AAATTTGCCG TTGAACACCT GGTCAATACG   47040

CGTTTTGGTG AGCAGCAATA TTGCGCTTCG ATGAGCCTTG GCGTTGAGAT TGATACCTCT   47100

GCTGCACAAA AGGCAATCGA CCGAGCTGGA CCAGCGCATT CGTGACACCG TCTCCTTCGA   47160

ACTTATTCGC AATGGAGTGT CATTCATCAA GGACNGCCTG ATCGCAAATG GTGCTATCCA   47220

CGCAGCGGCA ATCGAAAACC CTCAGCCGGT GACCAATATC TACAACATCA GCCTTGGTAT   47280

CCTGCGTGAT GAGCCAGCGC AGAACAAGGT AACCGTCAGT GCCGATAAGT TCAAAGTTAA   47340

ACCTGGTGTT GATACCAACA TTGAAACGTT GATCGAAAAC GCGCTGAAAA ACGCTGCTGA   47400

ATGTGCGGCG CTGGATGTCA CAAAGCAAAT GGCAGCAGAC AAGAAAGCGA TGGATGAACT   47460

GGCTTCCTAT GTCCGCACGG CCATCATGAT GGAATGTTTC CCCGGTGGTG TTATCTGGCA   47520

GCAGTGCCGT CGATAGTATG CAATTGATAA TTATTATCAT TTGCGGGTCC TTTCCGGCGA   47580

TCCGCCTTGT TACGGGGCGG CGACCTCGCG GGTTTTCGCT ATTTATGAAA ATTTTCCGGT   47640

TTAAGGCGTT TCCGTTCTTC TTCGTCATAA CTTAATGTTT TTATTTAAAA TACCCTCTGA   47700

AAAGAAAGGA AACGACAGGT GCTGAAAGCG AGCTTTTTGG CCTCTGTCGT TTCCTTTCTC   47760

TGTTTTTGTC CGTGGAATGA ACAATGGAAG TCAACAAAAA GCAGAGCTTA TCGATGATAA   47820

GCGGTCAAAC ATGAGAATTC GCGGCCGCAT AATACGACTC ACTATAGGGA TCTTAATTAA   47880

GGCGCCTGAT CAGGATCAGG TCGATGGCTT TGTTGTTCTC CGGGCAGCGC ACCGCCGTCG   47940

GAAACTCGGC CTTGCCTTTG GCGAACGTGG TGTCGACGTA GGCGATGTTG ATGCCCTTGT   48000

CTTCCAAGAA GCGCGCCACG TCGATGTTGT CCGGGTCTGC GCTGAAGTAC AGCGCCAGGT   48060

TGTCGAGCCT CTGCGAGTGC AGGTAGACAG CCGCCGTCTG AACCCTTGTG TAGGCCCAGA   48120

ACTGGACATC CGGGTTGTCG CGGATGACTC GACCCCAAGC GGCCACATAG GTGGGGCTGA   48180

AGAAGTCTCC ATCCCAGTGG ATGCGGAACA GCTTCGGAGC CTTGCGACGG TCGCAATCCT   48240

TGACGAACTC GGCGACCATC TCGGACAGCA GCGTCACGGT GTCTGTCAAG TCAGCGTCAC   48300

GCAACAGTTC CCAGTTGTGC AGCAGGACCG AGCTGACAGC CTTGCGAACT TTCTCCAGCT   48360

TGCCGGCGTA GCACACCTTG GCACAGAAGG CCGTCGCGTC CGGGCAGGAG AAGCCTTGAC   48420

CGGAGGGCAG GCCGATGCTG TTGGCGATAC CTACGGTGGC GTTGCCGCCC TTGGTGACGT   48480

GGACGTAGTT GGTGACCTTG CGGTCGTTCG AACGCTTCAG CTTGGCCATA CCTAGCCTTC   48540

CTTCGGTGGC TGTCAAGTTG TTGGATACAA AGCGCCCCGA GAGGGAGTCG AACCCTCACA   48600
```

-continued

```
CCGCGAACCG TCGCGGGGCC ACCGTGCCTA GTCGATAGAG GTCACTCGAC TCTCGTGGAC   48660

GTAGACCACG GTGTTGCCTA CGTTCACCGC GTAGTACAGG CCATCGGCAC CTCGTAGCTT   48720

GTGCCGAACC GTGCCCGACG TGGCCGTCAT GTCTTCGCCC CAGTCGGCGT TAGGTGCCCA   48780

GGTGACTCGC ATGGTGATCC CTTCAGTAGT CGGTGGCTGT CAAGTCAGCG GATACGGACG   48840

TACCCGTTGC CTCGAGCGAC GTAGATCTTG CCGTCGATGT AAACGCGCTG CTGCTGGTTC   48900

ATAATCCTAT TCCTTTCGGT GGCTGTCAAG TCTCAGGCCC AGCGACGAGT CGTCGGCCGG   48960

GGGCGGCGCA CCTTGGGCGC GTTGGCTCGC GGTGCCTTAC GGATGGCGGT GCCTACCGTG   49020

ATCTCTTCCA ACTGGCGTTC AGCCAGGCCG ACAGGCCGGG CGTCACCGGG CAGTTCGATC   49080

TTGTAATCGA AGTCAGTCCA CCCCTTCAGA CCCTTCTCCA GCTCGCGATC CAACAGACGC   49140

GGAGCCGACA GCTCAGGCGC AACAAACGGT GTCTTGACGC TCTCGCGGGC AGTAACCCGA   49200

ACCTCACGGT GCTCAGCGAA GACTGGCATA GTTCACCCCT TTGGTGGATG TCAAGCCTGA   49260

GCACCAAAGC TCAGGCGTAG TGGGTAGTCG GGAATCGAAC CCGATAGCTT CATAGCCACG   49320

TTCTACGGCT CAGCCATAGC TCAGCGATCA TTCCATCGCG CCAAGAGCTA CCCTCCCGAA   49380

TGCCGAACCA AAGCTCAGCA TTCGTAAGTG TGTATTCTCC CCGTGGCTCA GACAGTATCT   49440

ATCAGAACCT AACCACAGGT CTACATTTAG TTATCCGCAG TGCTCGCACT TTAACGGCAT   49500

CGAGCTTCCG CCGACCCTCA GTCCTCTGGC AGCGAACTAA AGGTTTGAGT CGGGCTGCGG   49560

CCCTTCTCGG TCTTGCGTGA TTCTCACTCT ACCGGATGTT TCGGTGGCTG TCAAGCGGGC   49620

CGTTTTGGTG TTGCAACGAT GCCCTCGTTT AGCGCCGCTG GCGTAATGCG CTACCCGCCT   49680

GATCTCACCG GTCCAAGTTG GTGATGCTTG CAGCTTACCC GATAACCGGG TGGCTGTCAA   49740

ACCGGAGAAT CTTGCCGCCG GATTTTCACC GGCACCGGCA CGATCCTCTC GGATCCGCCT   49800

ACCGCCTTGC TGCTGCGGTG ACACAAGAAT GCACTACTGG CCGGGTGGCT GTCAAGCCCT   49860

AATCGCAAAT TGGTGCCCTA GCTGCAGATA TGGCGCGTTC TCGGTGGCTG TAAAGGGCAC   49920

TACGTGCCGC TATCCGCTGG TCACGCTGGA CAGTCCCGGC AGCCCGTGCC GCGCATAGGC   49980

TGCTCACTAC GTGCCCGGTA TCGGCGTTGT CGTGCCGCTG TCGTGGTCGT CGCCCCGTCG   50040

CTGTCGCTGG TCTCGGTGGC ATCGCTTGAC AGTCGCCCCG CTATCCCCCG TTGCCGCTGG   50100

TCAGACGCTA ATCCGCTTAT TTCGCATAGG CTGCTCACTA TCGCATCGGT ATGCGTATGC   50160

GCTGGTCACA TATGCGTGTG GTGGTGGTGT GGTGTGCGTG TGTTTGCGCT GGTCAGCCGT   50220

GTGCGTACCG TATCCGCACA CTGTGCTTGT GCGTTTGCTG TGTGTCGAGG CCGGCTCTCG   50280

CATCGTCGCA TGTCAGCGCG GGTATGGGCG TGTATCGCAC GCTTTGCTAG CCGCGTGCCG   50340

C                                                                  50341
```

Figure 3:
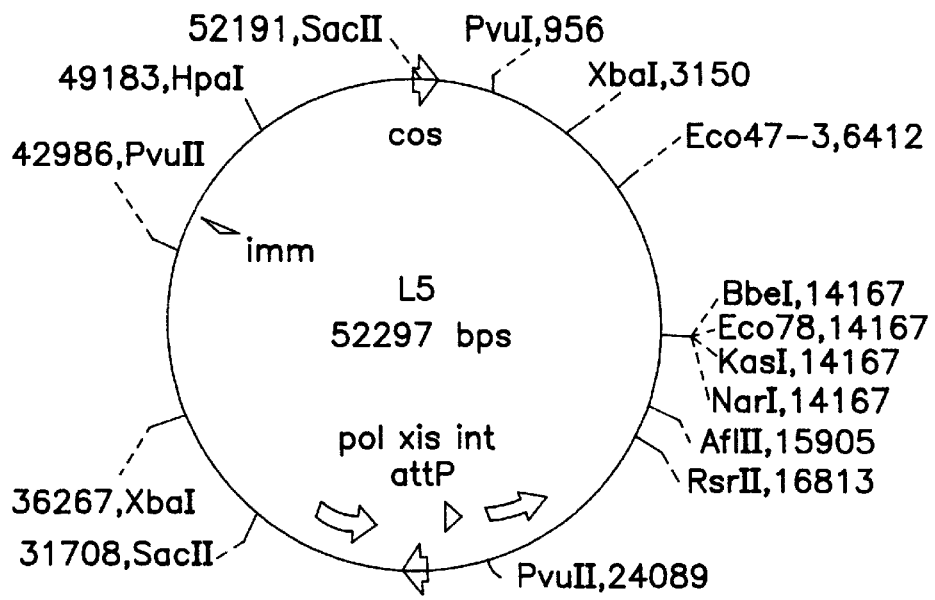
FIG. 3 represents a schematic diagram of the L5 genome highlighting the L5 cohesive (cos) and the integration regions, immunity regions, and DNA polymerase regions.

We claim:

1. A method of generating a mycobacterial mutation comprising:
   (a) obtaining an L5 shuttle phasmid comprising mycobacteriophage L5 with an *E. coli*-bacteriophage lambda cosmid and a transposon inserted in a non-essential region between the PvuII restriction site at nucleotide 42,986 and the SacII restriction site at nucleotide 52,191 of the mycobacteriophage L5 genome as shown in FIG. 3; and
   (b) infecting a mycobacterium with said L5 shuttle phasmid so as to cause delivery of the transposon from the L5 shuttle phasmid to the chromosome of the mycobacterium, thereby causing a mutation in a gene of the mycobacterium to occur.

2. The method of claim 1 wherein the cosmid is pYUB328.

3. The method of claim 1 wherein the cosmid is pYUB435.

4. The method of claim 1 wherein the transposon is IS1096.

5. The method of claim 1 wherein the L5 shuttle phasmid is selected from the group consisting of phAE46 and phAE47, deposited with the American Type Culture Collection, 10801 University Blvd., Manassas, Va. 20110-2209, and catalogued as ATCC Nos. 69629 and 69630, respectively.

6. The method of claim 1 wherein the mycobacterium is selected from the group consisting of *M. tuberculosis, M. smegmatis, M. bovis* and *M. avium*.

7. A method of producing a mycobacterial vaccine comprising:
   (a) obtaining an L5 shuttle phasmid comprising mycobacteriophage L5 with an *E. coli*-bacteriophage lambda cosmid and a transposon inserted in a non-essential region between the PvuII restriction site at nucleotide 42,986 and the SacII restriction site at nucleotide 52,191 of the mycobacteriophage L5 genome as shown in FIG. 3;
   (b) infecting a mycobacterium with said L5 shuttle phasmid so as to cause delivery of the transposon from the L5 shuttle phasmid to the chromosome of the mycobacterium, thereby causing a mutation in a gene of the mycobacterium to occur;
   (c) selecting for a marker gene present in the transposon so as to identify a mycobacterial mutant in which the transposon has been delivered into the mycobacterium; and
   (d) screening for an avirulent mutant, said avirulent mutant being useful as a mycobacterial vaccine.

8. The method of claim 7 wherein the marker gene is selected from the group consisting of a kanamycin resistance gene, a hydromycin resistance gene and an L5 immunity gene.

9. The method of claim 7 wherein the avirulent mutant is a leucine auxotroph.

* * * * *